United States Patent
Hagel et al.

(10) Patent No.: US 11,931,338 B2
(45) Date of Patent: Mar. 19, 2024

(54) NITRILATED PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 17/946,508

(22) Filed: Sep. 16, 2022

(65) Prior Publication Data

US 2023/0051548 A1 Feb. 16, 2023

Related U.S. Application Data

(63) Continuation of application No. PCT/CA2021/051647, filed on Nov. 19, 2021.

(60) Provisional application No. 63/115,991, filed on Nov. 19, 2020.

(51) Int. Cl.
| | |
|---|---|
| *A61K 31/4045* | (2006.01) |
| *A61P 25/00* | (2006.01) |
| *C07D 209/16* | (2006.01) |
| *C12N 9/10* | (2006.01) |
| *C12N 9/88* | (2006.01) |
| *C12N 15/52* | (2006.01) |
| *C12P 17/10* | (2006.01) |

(52) U.S. Cl.
CPC .......... *A61K 31/4045* (2013.01); *A61P 25/00* (2018.01); *C07D 209/16* (2013.01); *C12N 9/1007* (2013.01); *C12N 9/1029* (2013.01); *C12N 9/88* (2013.01); *C12N 15/52* (2013.01); *C12P 17/10* (2013.01); *C12Y 203/01087* (2013.01); *C12Y 401/01028* (2013.01); *C12Y 402/0102* (2013.01)

(58) Field of Classification Search
CPC ................................................ A61K 31/4045
See application file for complete search history.

(56) References Cited

U.S. PATENT DOCUMENTS 4,252,803 A * 2/1981 Webb ...................... A61P 25/04
540/602

FOREIGN PATENT DOCUMENTS

WO WO2011047156 A1 5/2011

OTHER PUBLICATIONS

Daniel, J. et al. Clinical potential of psilocybin as a treatment for mental health conditions. Mental Health Clin/, 2017;7 (1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Devereux et al., A comprehensive set of sequence analysis programs for the VAX. Nucleic Acids Res., 1984, 12: 387.
Altschul et al., Basic local alignment search tool. J Mol Biol. Oct. 5, 1990;215(3):403-10.
Thompson, J D, Higgines, D G and Gibson T J. Clustal W: improving the sensitivity of progressive multiple sequence alignment through sequence weighting, position-specific gap penalties and weight matrix choice. 1994, Nucleic Acid Res 22(22): 4673-4680.
Needleman and Wunsch. A general method applicable to the search for similarities in the amino acid sequence of two proteins J. Mol. Biol., 1970, 48: 443.
Smith and Waterman. Adv. Appl. Math., 1981, 2: 482.
Carillo and Lipton. SIAM J. Applied Math., 1988, 48:1073.
Vinograd et al. '126.Substituted Nitrotryptamines', Khimiya Geterotsiklicheskikh Soedinenii, 1984, vol. 9, pp. 1206-1210.
Menéndez-Perdomo et al. Benzylisoquinoline alkaloid analysis using high-resolution Orbitrap LC-MS n2021, Mass Spectrom 56: 34683.
S. Kawai et al., Transformation of *Saccharomyces cerevisiae* and other fungi: methods and possible underlying mechanism. Bioeng Bugs. Nov.-Dec. 2010;1(6):395-403.
Henikoff S & Henikoff, J G, Amino acid substitution matrices from protein blocks. Proc Natl Acad Sci U S A. Nov. 15, 1992;89(22):10915-9.
Jones et al. ePathOptimize: A Combinatorial Approach for Transcriptional Balancing of Metabolic Pathways. 2015, Sci Rep. 5: 11301.
Inserra et al., Psychedelics in Psychiatry: Neuroplastic, Immunomodulatory, and Neurotransmitter Mechanisms. 2020, Pharmacol Rev 73: 202.
Kim K. et al., Structure of a Hallucinogen-Activated Gq-Coupled 5-HT 2A Serotonin Receptor. 2020, Cell 182: 1574-1588.
Cregg et al., Recombinant protein expression in Pichia pastoris. Mol Biotechnol. (2000) 16(1): 23-52.
Maguire et al.,Radioligand binding assays and their analysis. 2012, Methods Mol Biol 897: 31.
Pyrgiotakis G. et al., Cell death discrimination with Raman spectroscopy and support vector machines. 2009, Ann. Biomed. Eng. 37: 1464-1473.
Schnepel C. et al. Enzymatic Halogenation: A Timely Strategy for Regioselective C-H Activation. Chemistry. Sep. 7, 2017;23(50):12064-12086.
Durak L.J. et al. Late-Stage Diversification of Biologically Active Molecules via Chemoenzymatic C-H Functionalization ACS Catal. Mar. 4, 2016; 6(3): 1451-1454.

(Continued)

*Primary Examiner* — Yong S. Chong
(74) *Attorney, Agent, or Firm* — BERESKIN & PARR LLP/S.E.N.C.R.L., s.r.l.; Michael Fenwick

(57) ABSTRACT

Disclosed are novel nitrilated psilocybin derivative compounds and pharmaceutical and recreational drug formulations containing the same. The compounds may be produced by reacting a reactant psilocybin derivative with a nitrile-group containing compound.

23 Claims, 41 Drawing Sheets

Specification includes a Sequence Listing.

(56) References Cited

OTHER PUBLICATIONS

Núñez et al., Target-drug interactions: first principles and their application to drug discovery. 2012, Drug Disc Today 17: 10.
Corr M.J. et al. Sonogashira diversification of unprotected halotryptophans, halotryptophan containing tripeptides; and generation of a new to nature bromo-natural product and its diversification in water Chem Sci. Mar. 1, 2017;8(3):2039-2046.
Chang et al., Isolation and Characterization of O-methyltransferases Involved in the Biosynthesis of Glaucine in Glaucium flavum. 2015, Plant Physiol. 169: 1127-1140.
Palangsuntikul, R. et al. Holographic Quantitative Structure-Activity Relationships of Tryptamine Derivatives at NMDA, 6HT1A and 5HT2A Receptors. Molecules 2013, 18, 8799-8811.
Berger, M.L. et al. Screening of 64 Tryptamines at NMDA, 5-HT1A, and 5-HT2A Receptors: A Comparative Binding and Modeling Study. Current Medicinal Chemistry, 2012, 19, 3044-3057.
Terrasso et al., Human neuron-astrocyte 3D co-culture-based assay for evaluation of neuroprotective compounds. 2017, J Pharmacol Toxicol Methods 83: 72.
Weaver et al., Test systems in drug discovery for hazard identification and risk assessment of human drug-induced liver injury. 2017, Expert Opin Drug Metab Toxicol 13: 767.
Donato et al., Culture and Functional Characterization of Human Hepatoma HepG2 Cells. 2015, Methods Mol Biol 1250: 77.
Roy A.D. et al. Development of fluorescent aryltryptophans by Pd mediated cross-coupling of unprotected halotryptophans in water. Chem Commun (Camb). Oct. 21, 2008;(39):4831-3.
Tarafder et al. The role of ion-pairing in peak deformations in overloaded reversed-phase chromatography of peptides. 2010, J Chromatogr A 1217:7065-7073.
Servillo L. et al., Benzylisoquinoline alkaloid analysis using high-resolution Orbitrap LC-MS n J. Agric. Food Chem 61: 5156-5162, 2013.
Petrunin et al. '130.Synthesis of Disubstituted Tryptamines by Nitration of 5-Methoxy-N-Phthalyltryptamine', Khimiya Geterotsiklicheskikh Soedinenii, Aug. 1987, vol. 8, pp. 839-842.
Ding et al., Synthesis of Nitriles from Primary Amides or Aldoximes under Conditions of a Catalytic Swern Oxidation. J. Org. Chem., 2018, 83, 12939-12944.
Shipilovskikh, et al., Dehydration of Amides to Nitriles under Conditions of a Catalytic Appel Reaction. Org. Lett. 2018, 20, 3, 728-731.
N. Uludag, Russ. J. Org. Chem. 56(9), 1640-1645, 2020.
A. Leggio, E. L. Belsito, S. Gallo, A. Liguori, Tetrahedron Lett., 58(15), 1512-1514, 2017.
Okamoto, et al, Practical synthesis of aromatic nitriles via gallium-catalysed electrophilic cyanation of aromatic C-H bonds. Chem. Commun., 2012, 48, 3127-3129.
Romanos et al., Foreign gene expression in yeast: a review. Yeast. Jun. 1992;8(6):423-88.
Finnin, B. and Morgan, T.M., Transdermal penetration enhancers: applications, limitations, and potential J Pharm Sci. Oct. 1999;88(10):955-8.
Mattanovich et al., Recombinant protein production in yeasts. Methods Mol. Biol., 2012, 824:329-58.
Runguphan W. et al. Diversification of monoterpene indole alkaloid analogs through cross-coupling. Org Lett. Jun. 7, 2013;15(11):2850-3.

\* cited by examiner

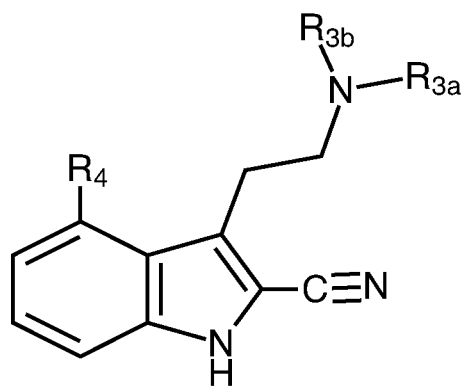
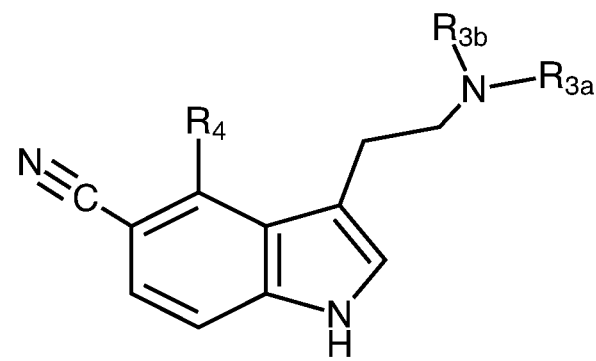
FIG. 3A  FIG. 3B
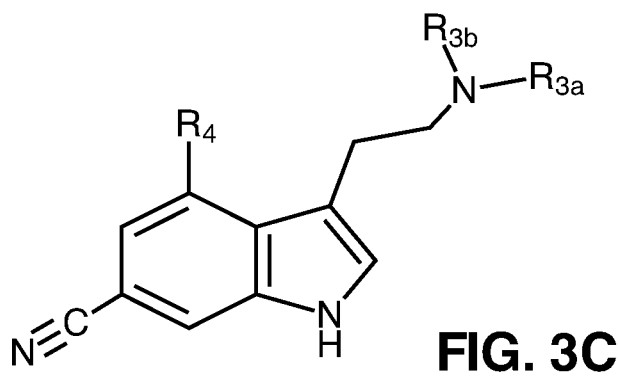
FIG. 3C
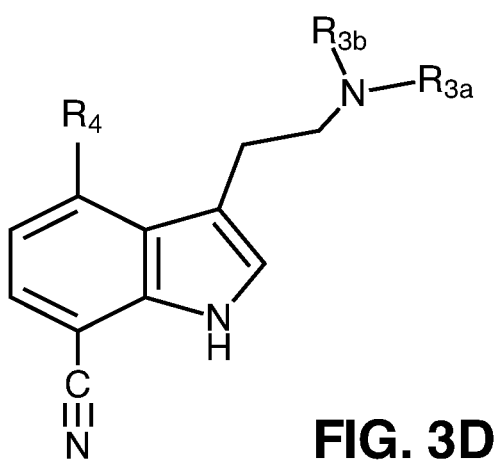
FIG. 3D

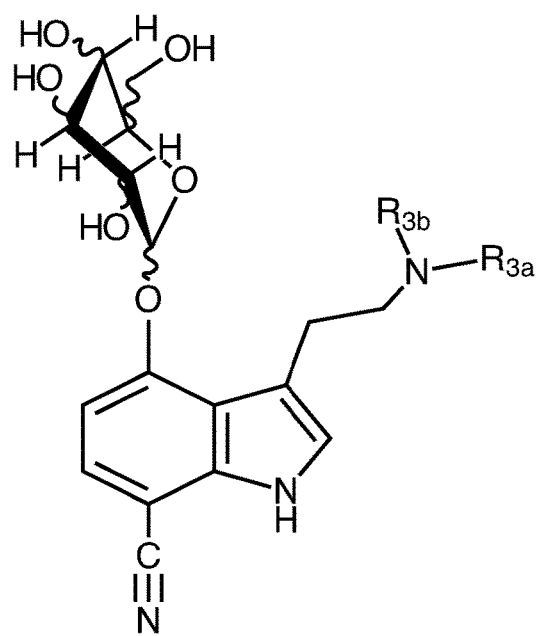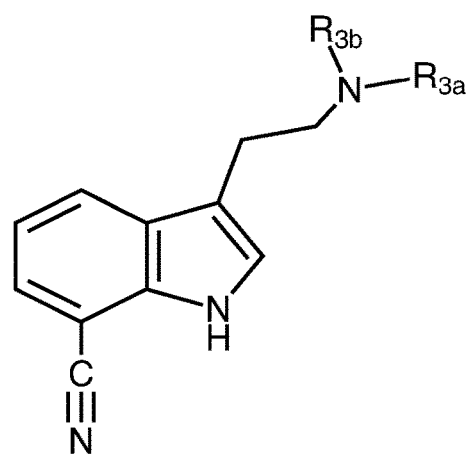
FIG. 6G                    FIG. 6H

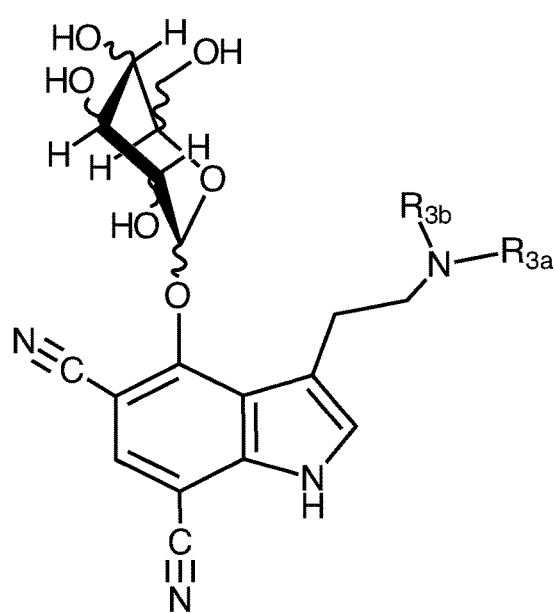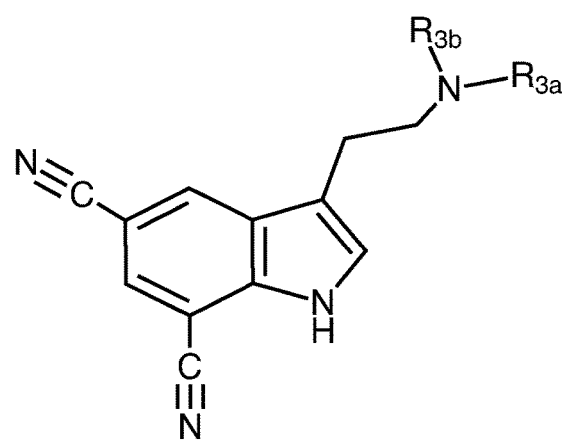
FIG. 7G　　　　　　　FIG. 7H

NITRILATED PSILOCYBIN DERIVATIVES AND METHODS OF USING

RELATED APPLICATION

This application is a continuation of PCT Application No. PCT/CA2021/051647 filed Nov. 19, 2021, which claims the benefit of U.S. Provisional Application No. 63/115,991 filed Nov. 19, 2020; the entire contents of Patent Application Nos. PCT/CA2021/051647 and 63/115,991 are hereby incorporated by reference.

INCORPORATION OF SEQUENCE LISTING

A computer readable form of the Sequence Listing "29664-P63274US01_SequenceListing.xml" (26,819 bytes), submitted via EFS-WEB and created on Sep. 15, 2022, is herein incorporated by reference.

FIELD OF THE DISCLOSURE

The compositions and methods disclosed herein relate to a chemical compound known as psilocybin. Furthermore, the compositions and methods disclosed herein relate in particular to nitrilated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al., Mental Health Clin/, 2017; 7(1): 24-28), including to treat anxiety in terminal cancer patients (Grob, C. et al., Arch. Gen. Psychiatry, 2011, 68(1) 71-78) and to alleviate symptoms of treatment-resistant depression (Cathart-Haris, R. L. et al., Lancet Psychiatry, 2016, 3: 619-627).

Although the toxicity of psilocybin is low, adverse side effects, including, for example, panic attacks, paranoia and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to nitrilated psilocybin derivative compounds and methods of making and using these compounds.

Accordingly, in one aspect, the present disclosure provides, in at least one embodiment, in accordance with the teachings herein, a chemical compound having the formula (I):

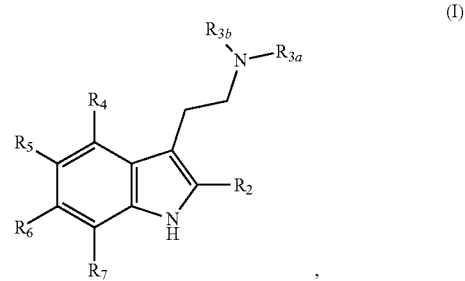

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be a hydrogen atom.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be an O-alkyl group.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be an O-acyl group.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be a phosphate group.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be a glycosyloxy group.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be a hydroxy group.

In at least one embodiment, in an aspect, at least one of $R_5$, $R_6$ or $R_7$ can be a nitrile group, and each non-nitrilated $R_5$, $R_6$ or $R_7$ can be a hydrogen atom or an alkyl group, $R_2$ can be a hydrogen atom or an alkyl group, and $R_4$ can be a hydrogen atom.

In at least one embodiment, each non-nitrilated $R_5$, $R_6$ or $R_7$ can be a hydrogen atom or a methyl group.

In at least one embodiment, of each non-nitrilated $R_5$, $R_6$ or $R_7$ at least one of $R_5$, $R_6$ or $R_7$ can be a methyl group.

In at least one embodiment, of each non-nitrilated $R_5$, $R_6$ or $R_7$ one, two or three of $R_5$, $R_6$ or $R_7$ can be a hydrogen atom.

In at least one embodiment, in an aspect, at least two of $R_2$, $R_5$, $R_6$, or $R_7$ can be a nitrile group.

In at least one embodiment, in an aspect, at least three of $R_2$, $R_5$, $R_6$, or $R_7$ can be a nitrile group.

In at least one embodiment, in an aspect, all four of $R_2$, $R_5$, $R_6$, or $R_7$ can be a nitrile group.

In at least one embodiment, in an aspect, the chemical compound can be selected from the group of compounds having formulas (III), (IV), (V), (VI), (VII), (VIII), (IX), (X) and (XI):

In another aspect, the present disclosure relates to pharmaceutical and recreational drug formulations comprising nitrilated psilocybin derivatives. Accordingly, in one aspect, the present disclosure provides, in at least one embodiment, a pharmaceutical or recreational drug formulation comprising an effective amount of a chemical compound having the formula (I):

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group, together with a pharmaceutically acceptable excipient, diluent or carrier.

In another aspect, the present disclosure relates to methods of treatment of psychiatric disorders. Accordingly, the present disclosure further provides, in one embodiment a method for treating a psychiatric disorder, the method comprising administering to a subject in need thereof a pharmaceutical formulation comprising a chemical compound having the formula (I):

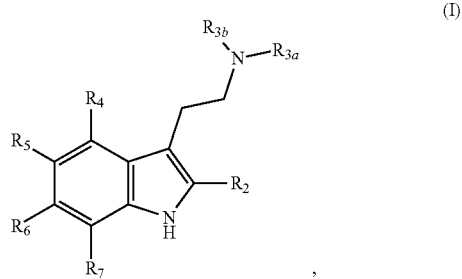

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group, wherein the pharmaceutical formulation is administered in an effective amount to treat the psychiatric disorder in the subject.

In at least one embodiment, in an aspect, the disorder can be a 5-HT$_{2A}$ receptor mediated disorder or a 5-HT$_{1A}$ receptor mediated disorder.

In at least one embodiment, in an aspect, a dose can be administered of about 0.001 mg to about 5,000 mg.

In another aspect, the present disclosure relates to methods of making nitrilated psilocybin derivatives. Accordingly, in one aspect, the present disclosure provides, in at least one embodiment, a method of making a nitrilated psilocybin derivative, the method comprising reacting a reactant psilocybin derivative compound with a nitrogen containing compound under conditions sufficient to form a nitrilated psilocybin derivative.

In at least one embodiment, in an aspect, the reactant psilocybin derivative can be a chemical compound having the formula (II):

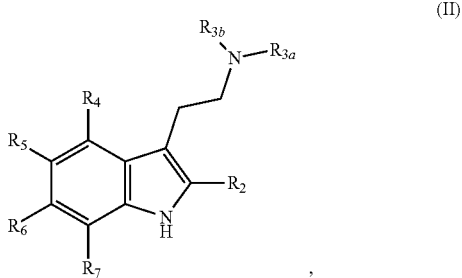

(II)

wherein, at least one of $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group.

In at least one embodiment, in an aspect, at least one of $R_2$, $R_5$, $R_6$, and $R_7$ in compound (II) can be a carboxyl group, a formyl group or an amino group, wherein each non-carboxylated, non-formylated, or non-aminated $R_2$, $R_5$, $R_6$ or $R_7$ is a hydrogen atom, an alkyl group or O-alkyl group, and wherein in the formed nitrilated psilocybin derivative the at least one carboxyl group, formyl group or amino group is substituted by a nitrile group.

In at least one embodiment, each carboxyl group, formyl group or amino group present on the compound of formula (II) can be substituted with a nitrile group.

In at least one embodiment, in an aspect, at least one of $R_2$, $R_5$, $R_6$, and $R_7$ in compound (II) can be a carboxy group, wherein each non-carboxylated, $R_2$, $R_5$, $R_6$, or $R_7$ is a hydrogen atom, an alkyl or O-alkyl group, wherein an intermediate psilocybin derivative compound comprising one or more primary amide groups is formed in a reaction of one or more of the carboxy groups with ammonia or ammonium chloride, wherein the primary amide group is then dehydrated, and wherein in the formed nitrilated psilocybin derivative the one or more carboxy groups are substituted by a nitrile group.

In at least one embodiment, in an aspect, at least one of $R_2$, $R_5$, $R_6$, and $R_7$ in compound (II) can be a formyl group, wherein each non-formylated, $R_2$, $R_5$, $R_6$, or $R_7$ is a hydrogen atom, an alkyl group or O-alkyl group, wherein an intermediate psilocybin derivative compound comprising an oxime group is formed in a reaction of one or more of the formyl groups with hydroxyamine hydrochloride salt, wherein the one or more oxime groups are then dehydrated to form the nitrilated psilocybin derivative, and wherein in the formed nitrilated psilocybin derivative the one or more formyl groups are substituted by a nitrile group.

In at least one embodiment, in an aspect, at least one of $R_2$, $R_5$, $R_6$, and $R_7$ in compound (II) can be an amino group, wherein each non-aminated, $R_2$, $R_5$, $R_6$, or $R_7$ is a hydrogen atom, an alkyl group or O-alkyl group, wherein an intermediate diazonium salt psilocybin derivative is formed in a reaction of one or more of the amino groups with a nitrite salt, wherein the diazonium salt is then reacted with copper cyanide, and wherein in the formed nitrilated psilocybin derivative the one or more amino groups are substituted by a nitrile group.

In at least one embodiment, in an aspect, all four of $R_2$, $R_5$, $R_6$, and $R_7$ can be a hydrogen atom and the compound (II) can be reacted with cyanogen bromide to form the nitrilated psilocybin derivative.

In at least one embodiment, in an aspect, in the formed nitrilated psilocybin derivative (compound of formula (I)), at least one of $R_5$ or $R_7$ can be a nitrile group, and wherein $R_5$, or $R_7$ which are not a nitrile group, and $R_2$ and $R_6$ are each a hydrogen atom.

In at least one embodiment, in an aspect, in the formed nitrilated psilocybin derivative (compound of formula (I)), $R_5$ and $R_7$ can be a nitrile group, and $R_2$ and $R_6$ are a hydrogen atom.

In at least one embodiment, in an aspect, in the chemical compound having formula (II), $R_4$ can be an O-alkyl group, and in the formed nitrilated psilocybin derivative (compound of formula (I)), at least one of $R_5$ or $R_7$ can be a nitrile group, and wherein $R_5$ or $R_7$ which are not a nitrile group, and $R_2$ and $R_6$ are each a hydrogen atom, and $R_4$ is an O-alkyl group.

In at least one embodiment, in an aspect, in the chemical compound having formula (II), $R_4$ can be an O-acyl group, and in the formed nitrilated psilocybin derivative (compound of formula (I)), at least one of $R_5$ or $R_7$ can be a nitrile group, and wherein $R_5$ or $R_7$ which are not a nitrile group and $R_2$ and $R_6$ are each a hydrogen atom, and $R_4$ is an O-acyl group.

In at least one embodiment, in an aspect, in the chemical compound having formula (II), $R_4$ can be a hydroxy group, and in the formed nitrilated psilocybin derivative (compound of formula (I)), at least one of $R_5$ or $R_7$ can be a nitrile group, and wherein $R_5$ or $R_7$ which are not a nitrile group, and $R_2$ and $R_6$ are each a hydrogen atom, and $R_4$ is a hydroxy group.

In at least one embodiment, in an aspect, in the chemical compound having formula (II), $R_4$ can be a phosphate group, and in the formed nitrilated psilocybin derivative (compound of formula (I)), at least one of $R_5$ or $R_7$ can be a nitrile group, and wherein $R_5$ or $R_7$ which are not a nitrile group and $R_2$ and $R_6$ are each a hydrogen atom, wherein $R_4$ is a phosphate group.

In at least one embodiment, in an aspect, in the chemical compound having formula (II) $R_4$ can be a glycosyloxy group, and the formed nitrilated psilocybin derivative (compound of formula (I)), at least one of $R_5$ or $R_7$ can be a nitrile group, and wherein $R_5$, or $R_7$ which are not a nitrile group and $R_2$ and $R_6$ are each a hydrogen atom, and $R_4$ is a glycosyloxy group.

In at least one embodiment, in an aspect, in the chemical compound having formula (II), $R_4$ can be a hydrogen atom, and in the formed nitrilated psilocybin derivative (compound of formula (I)) at least one of $R_5$ or $R_7$ can be a nitrile group, and wherein $R_5$, or $R_7$ which are not a nitrile group and $R_2$ and $R_6$ are each a hydrogen atom, and $R_4$ is a hydrogen atom.

In at least one embodiment, in an aspect, in the chemical compound having formula (II), $R_4$ can be an O-alkyl group, and in the formed nitrilated psilocybin derivative (compound of formula (I)), $R_5$ and $R_7$ can be a nitrile group, and $R_2$ and $R_6$ are a hydrogen atom, and $R_4$ is an O-alkyl group.

In at least one embodiment, in an aspect, in the chemical compound having formula (II), $R_4$ can be an O-acyl group, and in the formed nitrilated psilocybin derivative (compound of formula (I)), $R_5$ and $R_7$ can be a nitrile group, and $R_2$ and $R_6$ are a hydrogen atom, and $R_4$ is an O-acyl group.

In at least one embodiment, in an aspect, in the chemical compound having formula (II), $R_4$ can be a hydroxy group, and in the formed nitrilated psilocybin derivative (compound of formula (I)), at $R_5$ and $R_7$ can be a nitrile group, and $R_2$ and $R_6$ are a hydrogen atom, and $R_4$ is a hydroxy group.

In at least one embodiment, in an aspect, in the chemical compound having formula (II), $R_4$ can be a phosphate group, and in the formed nitrilated psilocybin derivative (compound of formula (I)), at $R_5$ and $R_7$ can be a nitrile group, and $R_2$ and $R_6$ are a hydrogen atom, and $R_4$ is a phosphate group.

In at least one embodiment, in an aspect, in the chemical compound having formula (II), $R_4$ can be a glycosyloxy group, and in the formed nitrilated psilocybin derivative (compound of formula (I)), at $R_5$ and $R_7$ can be a nitrile group, and $R_2$ and $R_6$ are a hydrogen atom, and $R_4$ is a glycosyloxy group.

In at least one embodiment, in an aspect, in the chemical compound having formula (II), $R_4$ can be a hydrogen atom, and in the formed nitrilated psilocybin derivative (compound of formula (I)), at $R_5$ and $R_7$ can be a nitrile group, and $R_2$ and $R_6$ are a hydrogen atom, and $R_4$ is a hydrogen atom.

In at least one embodiment, in an aspect, the formed chemical compound can be selected from the group of compounds having formulas (III), (IV), (V), (VI), (VII), (VIII), (IX), (X) and (XI):

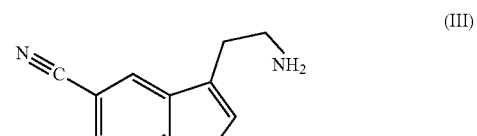
(III)

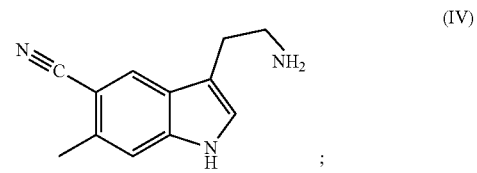
(IV)

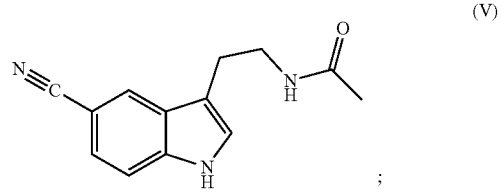
(V)

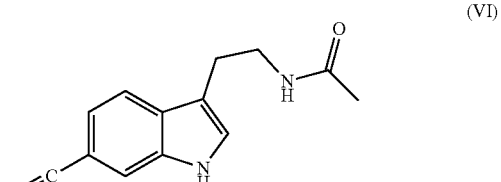
(VI)

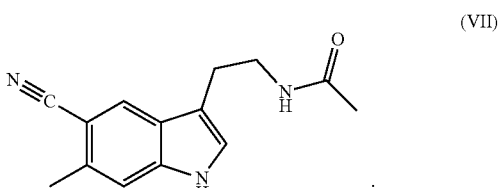
(VII)

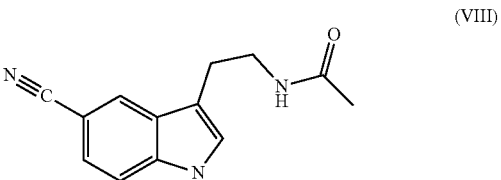
(VIII)

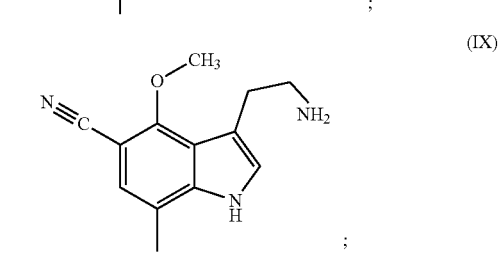
(IX)

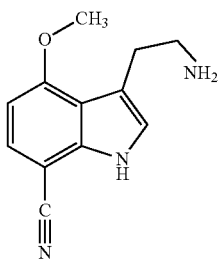

(X)

; and

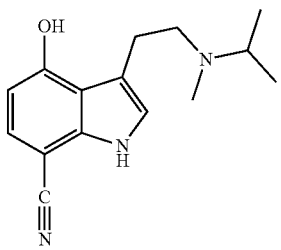

(XI)

In another aspect the present disclosure provides, in at least one embodiment, a use of a chemical compound having the formula (I):

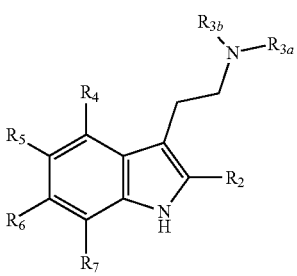

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group, in the manufacture of a pharmaceutical or recreational drug formulation.

In at least one embodiment, the manufacture can comprise formulating the chemical compound with an excipient, diluent, or carrier.

In another aspect, the present disclosure relates to further methods of making nitrilated psilocybin derivatives. Accordingly, in one aspect, the present disclosure provides in at least one aspect, a method of making a nitrilated psilocybin derivative the method comprising:

(a) contacting a nitrilated psilocybin precursor compound with a host cell comprising a psilocybin biosynthetic enzyme complement; and (b) growing the host cell to produce a nitrilated psilocybin derivative or salts thereof having the formula (I):

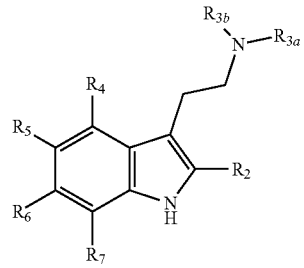

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group.

In at least one embodiment, in an aspect, the psilocybin biosynthetic enzyme complement can comprise at least one enzyme selected from a nucleic acid selected from:

(a) SEQ.ID NO: 4, SEQ.ID NO: 8, and SEQ.ID NO: 11;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ.ID NO: 5, SEQ.ID NO: 9 or SEQ.ID NO: 12;

(f) a nucleic acid sequence that encodes a functional variant of any one of the amino acid sequences set forth in SEQ.ID NO: 5, SEQ.ID NO:7 or SEQ.ID NO: 12; and (g) a nucleic acid sequence that hybridizes under stringent conditions to any one of the nucleic acid sequences set forth in (a), (b), (c), (d), (e) or (f).

In at least one embodiment, in an aspect, the nitrilated psilocybin precursor compound can be a compound, having the formula (XIII):

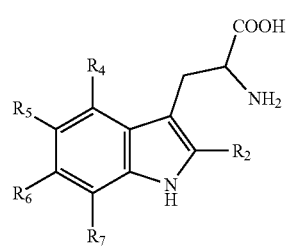

(XIII)

wherein at least one of $R_2$, $R_4$, $R_5$, $R_6$ and $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group;

wherein the psilocybin biosynthetic enzyme complement can comprise: a tryptophan decarboxylase encoded by a nucleic acid sequence selected from:
(a) SEQ.ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ.ID NO: 12;
(f) a nucleic acid sequence that encodes a functional variant of the amino acid sequence set forth in SEQ.ID NO: 12; and
(g) a nucleic acid sequence that hybridizes under stringent conditions to any one of the nucleic acid sequences set forth in (a), (b), (c), (d), (e) or (f); and the formed nitrilated psilocybin derivative can be a compound having formula (XIV):

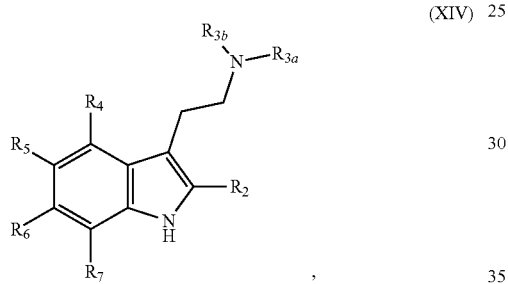

(XIV)

wherein at least one of $R_2$, $R_4$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group.

In at least one embodiment, in an aspect, the nitrile psilocybin precursor compound can be a nitrilated indole compound having the formula (XV):

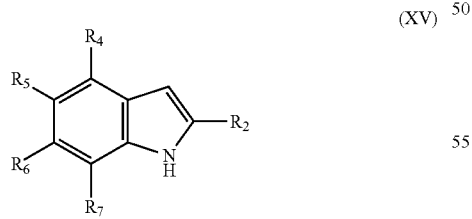

(XV)

wherein at least one of $R_2$, $R_4$, $R_5$, $R_6$ and $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom;
wherein the psilocybin biosynthetic enzyme complement can comprise:

(i) a tryptophan synthase subunit B polypeptide encoded by a nucleic acid selected from:
(a) SEQ.ID NO: 8;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ.ID NO: 9;
(f) a nucleic acid sequence that encodes a functional variant of the amino acid sequence set forth in SEQ.ID NO: 9; and
(g) a nucleic acid sequence that hybridizes under stringent conditions to any one of the nucleic acid sequences set forth in (a), (b), (c), (d), (e) or (f); and
(ii) a tryptophan decarboxylase encoded by a nucleic acid sequence selected from:
(a) SEQ.ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ.ID NO: 12;
(f) a nucleic acid sequence that encodes a functional variant of the amino acid sequence set forth in SEQ.ID NO: 12; and
(g) a nucleic acid sequence that hybridizes under stringent conditions to any one of the nucleic acid sequences set forth in (a), (b), (c), (d), (e) or (f);
and wherein the formed nitrilated psilocybin derivative can be a compound having formula (XIV):

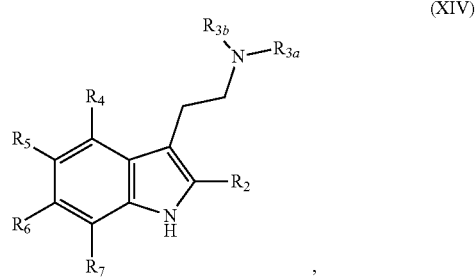

(XIV)

wherein at least one of $R_2$, $R_4$, $R_5$, $R_6$, or $R_7$ is a nitrile group, and group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group.

In at least one embodiment, in an aspect, $R_{3A}$ and $R_{3B}$ in formula (XIV) can each be a hydrogen atom.

In at least one embodiment, in an aspect, the psilocybin biosynthetic enzyme complement can further comprise an N-acetyl transferase.

In at least one embodiment, in an aspect, the N-acetyl transferase can be an enzyme encoded by a nucleic acid sequence selected from:

(a) SEQ.ID NO: 4;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ.ID NO: 5;
(f) a nucleic acid sequence that encodes a functional variant of the amino acid sequence set forth in SEQ.ID NO: 5; and
(g) a nucleic acid sequence that hybridizes under stringent conditions to any one of the nucleic acid sequences set forth in (a), (b), (c), (d), (e) or (f).

In at least one embodiment, in an aspect, the formed nitrilated psilocybin compound can have the formula (XVI):

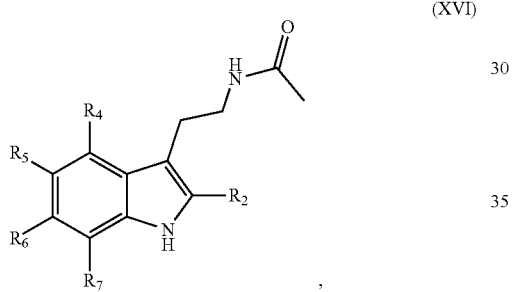

(XVI)

wherein, at least one of $R_2$, $R_4$, $R_5$, $R_6$ or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom.

In at least one embodiment, in an aspect, the nitrilated psilocybin derivative compound having formula (I) can be selected from the group consisting of compounds having formulas

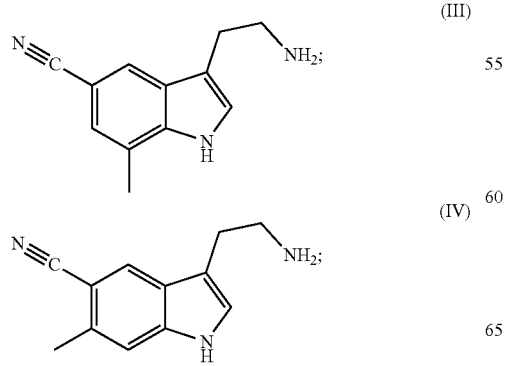

(III)

(IV)

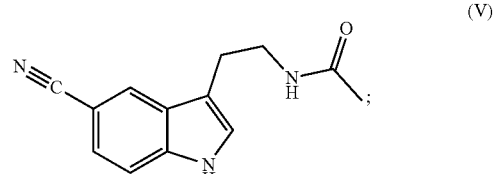

(V)

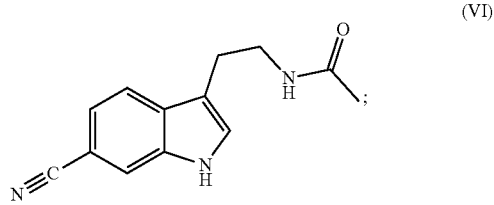

(VI)

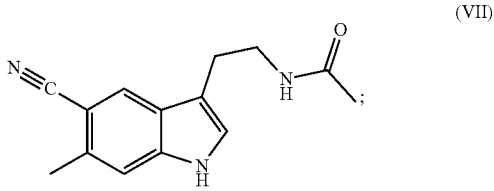

(VII)

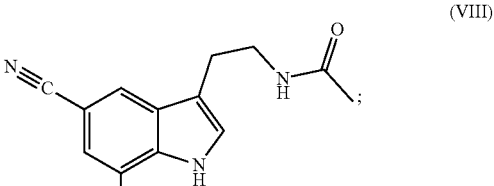

(VIII)

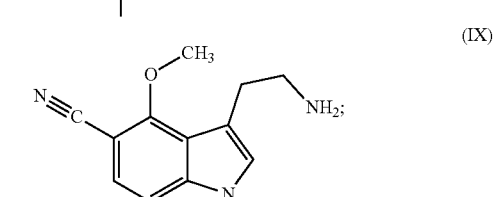

(IX)

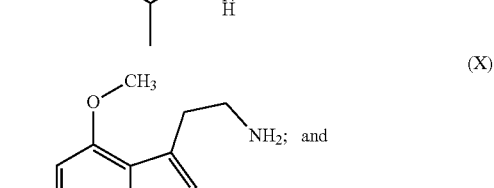

(X) and

(XI)

In at least one embodiment, in an aspect, the nitrilated psilocybin precursor compound can be contacted with the host cell by including the nitrilated psilocybin precursor compound in a growth medium for the host cell.

In at least one embodiment, in an aspect, the method can further include a step comprising isolating the nitrilated psilocybin derivative.

In at least one embodiment, in an aspect, the host cell can be a microbial cell.

In at least one embodiment, in an aspect, the host cell can be a bacterial cell or a yeast cell.

In another aspect, the present disclosure provides, in at least one embodiment, a method for modulating a 5-HT$_{2A}$ receptor or 5-HT$_{1A}$ receptor, the method comprising contacting a 5-HT$_{2A}$ receptor or a 5-HT$_{1A}$ receptor with a chemical compound or salt thereof having formula (I):

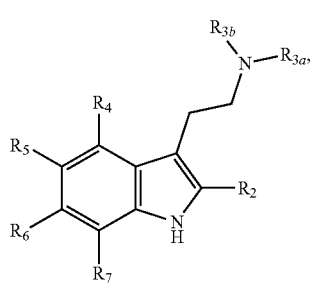

(I)

wherein, at least one of R$_2$, R$_5$, R$_6$, or R$_7$ is a nitrile group, and wherein each non-nitrilated R$_2$, R$_5$, R$_6$, or R$_7$ is a hydrogen atom, an alkyl group, or O-alkyl group, wherein R$_4$ is an O-alkyl group, an O-acyl group, a hydroxy group, a phosphate group, a glycosyloxy group, or a hydrogen atom and wherein R$_{3A}$ and R$_{3B}$ are independently a hydrogen atom, an alkyl group, acyl group or an aryl group, or an acyl group under reaction conditions sufficient to thereby modulate receptor activity.

In some embodiments, in an aspect, the reaction conditions can be in vitro reaction conditions.

In some embodiments, in an aspect, the reaction conditions can be in vivo reaction conditions.

In another aspect the present disclosure provides, in at least one embodiment, a use of a chemical compound having the formula (I):

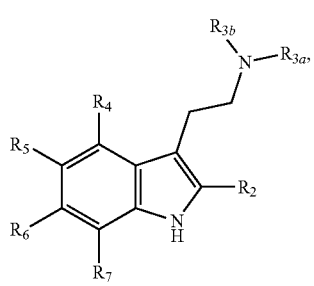

(I)

wherein, at least one of R$_2$, R$_5$, R$_6$, or R$_7$ is a nitrile group, and wherein each non-nitrilated R$_2$, R$_5$, R$_6$, or R$_7$ is a hydrogen atom, an alkyl group, or O-alkyl group, wherein R$_4$ is an O-alkyl group, an O-acyl group, a hydroxy group, a phosphate group, a glycosyloxy group, or a hydrogen atom and wherein R$_{3A}$ and R$_{3B}$ are independently a hydrogen atom, an alkyl group, acyl group or an aryl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIGS. 3A, 3B, 3C, and 3D, depict the chemical structures of certain example nitrilated psilocybin derivatives, notably a 2-nitrile-psilocybin derivative (FIG. 3A), a 5-nitrile-psilocybin derivative (FIG. 3B), a 6-nitrile-psilocybin derivative (FIG. 3C), and a 7-nitrile-psilocybin derivative (FIG. 3D).

FIGS. 6A, 6B, 6C, 6D, 6E, 6F, 6G and 6H depict the chemical structures of certain example nitrilated psilocybin derivatives, notably O-alkylated nitrilated psilocybin derivatives, notably a 4-O-methyl-7-nitrile-psilocybin derivative (FIG. 6A), a 4-O-ethyl-7-nitrile-psilocybin derivative (FIG. 6B), O-acylated nitrilated psilocybin derivatives, notably a 4-acetyl-7-nitrile-psilocybin derivative (FIG. 6C), a 4-propanoyl-7-nitrile-psilocybin derivative (FIG. 6D), a 4-hydroxy-7-nitrile-psilocybin derivative (FIG. 5E), a 4-phospho-7-nitrile-psilocybin derivative (FIG. 6F), a 4-glycosyl-7-nitrile-psilocybin derivative (FIG. 6G), and a 7-nitrile-psilocybin derivative (FIG. 6H).

FIGS. 7A, 7B, 7C, 7D, 7E, 7F, 7G and 7H depict the chemical structures of certain example nitrilated psilocybin derivatives, notably O-alkylated nitrilated psilocybin derivatives, notably a 4-O-methyl-5,7-di-nitrile-psilocybin derivative (FIG. 7A), a 4-O-ethyl-5,7-di-nitrile-psilocybin derivative (FIG. 7B), O-acylated nitrilated psilocybin derivatives, notably a 4-acetyl-5,7-di-nitrile-psilocybin derivative (FIG. 7C), a 4-propanoyl-5,7-di-nitrile-psilocybin derivative (FIG. 7D), a 4-hydroxy-5,7-di-nitrile-psilocybin derivative (FIG. 7E), a 4-phospho-5,7-di-nitrile-psilocybin derivative (FIG. 7F), a 4-glycosyl-5,7-di-nitrile-psilocybin derivative (FIG. 7G), and a 5,7-di-nitrile-psilocybin derivative (FIG. 7H).

DETAILED DESCRIPTION

Figure 1:
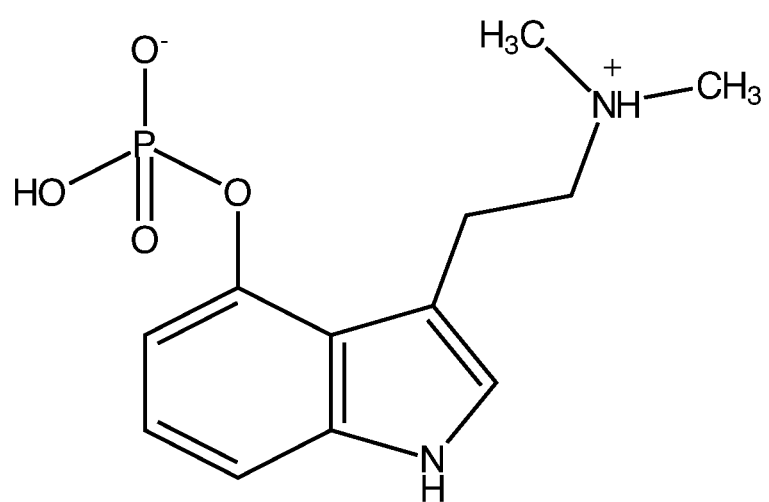
FIG. 1 depicts the chemical structure of psilocybin.

The figures together with the following detailed description make apparent to those skilled in the art how the disclosure may be implemented in practice.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore, any range of values described herein is intended to specifically include the limiting values of the range, and any intermediate value or sub-range within the given range, and all such intermediate values and sub-ranges are individually and specifically disclosed (e.g., a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent, or patent application was specifically and individually indicated to be incorporated by reference in its entirety.

Terms and Definitions

The term "psilocybin", refers to a chemical compound having the structure set forth in FIG. 1.

Figure 2:
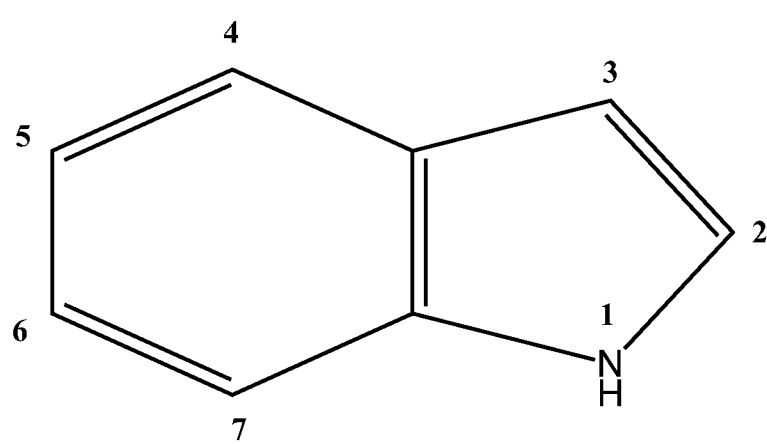
FIG. 2 depicts a certain prototype structure of psilocybin and psilocybin derivative compounds, namely an indole. Certain carbon and nitrogen atoms may be referred to herein by reference to their position within the indole structure, i.e., N$_1$, C$_2$, C$_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example, $R_4$ and $R_6$ reference chemical groups attached to the $C_4$ and $C_6$ atom, respectively. In addition, $R_{3A}$ and $R_{3B}$, in this respect, reference chemical groups extending from the ethyl-amino group extending in turn from the $C_3$ atom of the prototype indole structure.

The term "nitrilated psilocybin derivative" refers to a psilocybin derivative compound to which a nitrile group (C≡N) has been bonded to psilocybin or a psilocybin derivative. Reference may be made to specific carbon atoms which may be nitrilated. For example, a 5-nitrile-psilocybin derivative refers to a psilocybin derivative in which carbon atom number 5 (as identified in the indole prototype structure) possesses a nitrile group, or, similarly, 7-nitrile-psilocybin derivative refers to a psilocybin derivative in which carbon atom number 7 (as identified in the indole prototype structure) possess a nitrile group. Thus, for example, nitrilated psilocybin derivatives include, single nitrile derivatives, 2-nitrile, 4-nitrile, 5-nitrile, 6-nitrile, and 7-nitrile psilocybin derivatives, for example, and multiple nitrile derivatives, such as, for example, 5,7-di-nitrile psilocybin derivatives, and 2,5,7-ti-nitrile psilocybin derivatives. The term nitrilated psilocybin derivatives further includes chemical compounds having the chemical formula (I):

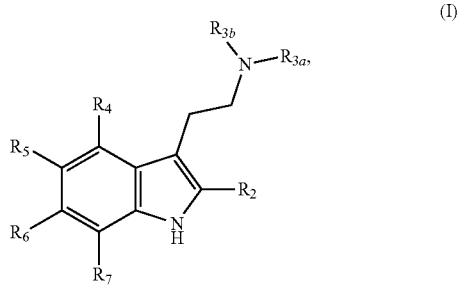

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are independently a hydrogen atom, an alkyl group, acyl group or an aryl group. Furthermore, it is noted that when $R_4$ is a phosphate group, the term nitrilated psilocybin derivatives includes compounds having the formula (XII):

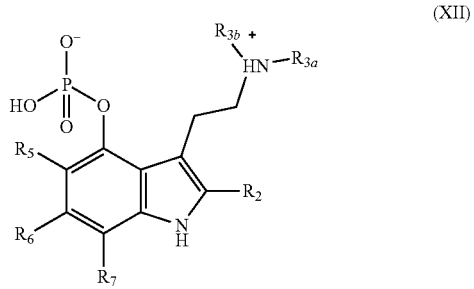

(XII)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, and wherein $R_{3A}$ and $R_{3B}$ are independently a hydrogen atom, an alkyl group, acyl group or an aryl group. The term further includes salts of nitrilated psilocybins, such as a sodium salt, a potassium salt etc.

The term "phosphate group" or "phospho", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein refers to a molecule containing one atom of oxygen bonded to one atom of hydrogen, and having the formula —OH. A hydroxy group through its oxygen atom may be chemically bonded to another entity.

The term "nitrile group" and "nitrile", as used herein, refer to a molecule containing one atom of carbon bonded to a nitrogen atom and having the formula —C≡N. It is to be understood that a nitrile group through its carbon atom may be chemically bonded to another entity. Furthermore, it is noted that an entity attached to a nitrile group may be referred to herein as a "nitrilated" entity, e.g., a nitrilated psilocybin derivative is a psilocybin derivative possessing a nitrile group.

The terms "glycosylated" or "glycosyl", as used herein, refer to a saccharide group, such as a mono-, di-, tri- oligo- or a poly-saccharide group, which can be or has been bonded from its anomeric carbon either in the pyranose or furanose form, either in the α or the β conformation. When bonded through its anomeric carbon via an oxygen atom to another entity, the bonded saccharide group, inclusive of the oxygen atom, may be referred to herein as a "glycosyloxy" group. Example monosaccharide groups include, but are not limited to, a pentosyl, a hexosyl, or a heptosyl group. The glycosyloxy group may also be substituted with various groups. Such substitutions may include lower alkyl, lower alkoxy, acyl, carboxy, carboxyamino, amino, acetamido, halo, thio, nitro, keto, and phosphatyl groups, wherein the substitution may be at one or more positions on the saccharide. Included in the term glycosyl are further stereoisomers, optical isomers, anomers, and epimers of the glycosyloxy group. Thus, a hexose group, for example, can be either an aldose or a ketose group, can be of D- or L-configuration, can assume either an α or β conformation, and can be a dextro- or levo-rotatory with respect to plane-polarized light. Example glycosyloxy groups further include, without limitation, glucosyl groups, glucuronic acid groups, galactosyl groups, fucosyl groups, xylose groups, arabinose groups, and rhamnose groups.

The term "alkyl group" refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl, and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$C_2H_5$), propyl groups (—$C_3H_7$), and butyl groups (—$C_4H_9$).

The term "O-alkyl group", refers to a hydrocarbon group arranged in a chain having the formula —O—$C_nH_{2n+1}$. Alkyl groups include, without limitation, O-methyl groups (—O—$CH_3$), O-ethyl groups (—O—$C_2H_5$), O-propyl groups (—O—$C_3H_7$) and O-butyl groups (—O—$C_4H^9$).

The term "acyl group" refers to a carbon atom double bonded to an oxygen and single bonded to an "alkyl" group. The carbon atom further can be bonded to another entity. An acyl group can be described by the chemical formula: —C(=O)—$C_nH_{2n+1}$.

The term "O-acyl group" refers to an acyl group in which the carbon atom is single bonded to an additional oxygen atom. The additional oxygen atom can be bonded to another entity. An O-acyl group (—O—C(=O)-alkyl) can be described by the chemical formula: —O—C(=O)—$C_nH_{2n+1}$. Furthermore, depending on the carbon chain, length specific O-acyl groups may be termed an acetyl group (n=1), a propanoyl group (n=2), propoxycarbonyl group (n=3), a butoxycarbonyl group (n=4) etc.

The term "5-$HT_{2A}$ receptor", as used herein, refers to a subclass of a family of receptors for the neurotransmitter and peripheral signal mediator serotonin. 5-$HT_{2A}$ receptors can mediate a plurality of central and peripheral physiologic functions of serotonin. Central nervous system effects can include mediation of hallucinogenic effects of hallucinogenic compounds.

The term "modulating 5-$HT_{2A}$ receptors", as used herein, refers to the ability of a compound disclosed herein to alter the function of 5-$HT_{2A}$ receptors. A 5-$HT_{2A}$ receptor modulator may activate the activity of a $5\text{-}HT_{2A}$ receptor, may activate or inhibit the activity of a $5\text{-}HT_{2A}$ receptor depending on the concentration of the compound exposed to the $5\text{-}HT_{2A}$ receptor, or may inhibit the activity of a $5\text{-}HT_{2A}$ receptor. Such activation or inhibition may be contingent on the occurrence of a specific event, such as activation of a signal transduction pathway, and/or maybe manifest only in particular cell types. The term "modulating $5\text{-}HT_{2A}$ receptors," also refers to altering the function of a $5\text{-}HT_{2A}$ receptor by increasing or decreasing the probability that a complex forms between a $5\text{-}HT_{2A}$ receptor and a natural binding partner to form a multimer. A $5\text{-}HT_{2A}$ receptor modulator may increase the probability that such a complex forms between the $5\text{-}HT_{2A}$ receptor and the natural binding partner, may increase or decrease the probability that a complex forms between the $5\text{-}HT_{2A}$ receptor and the natural binding partner depending on the concentration of the compound exposed to the $5\text{-}HT_{2A}$ receptor, and or may decrease the probability that a complex forms between the $5\text{-}HT_{2A}$ receptor and the natural binding partner.

The term "$5\text{-}HT_{2A}$ receptor-mediated disorder", as used herein, refers to a disorder that is characterized by abnormal $5\text{-}HT_{2A}$ receptor activity. A $5\text{-}HT_{2A}$ receptor-mediated disorder may be completely or partially mediated by modulating $5\text{-}HT_{2A}$ receptors. In particular, a $5\text{-}HT_{2A}$ receptor-mediated disorder is one in which modulation of $5\text{-}HT_{2A}$ receptors results in some effect on the underlying disorder e.g., administration of a $5\text{-}HT_{2A}$ receptor modulator results in some improvement in at least some of the subjects being treated.

The term "$5\text{-}HT_{2A}$ receptor-mediated disorder", as used herein, refers to a disorder that is characterized by abnormal $5\text{-}HT_{2A}$ receptor activity. A $5\text{-}HT_{2A}$ receptor-mediated disorder may be completely or partially mediated by modulating $5\text{-}HT_{2A}$ receptors. In particular, a $5\text{-}HT_{2A}$ receptor-mediated disorder is one in which modulation of $5\text{-}HT_{2A}$ receptors results in some effect on the underlying disorder e.g., administration of a $5\text{-}HT_{2A}$ receptor modulator results in some improvement in at least some of the subjects being treated.

The term "$5\text{-}HT_{1A}$ receptor", as used herein, refers to a subclass of a family of receptors for the neurotransmitter and peripheral signal mediator serotonin. $5\text{-}HT_{1A}$ receptors can mediate a plurality of central and peripheral physiologic functions of serotonin. Ligand activity at $5\text{-}HT_{1A}$ is generally not associated with hallucination, although many hallucinogenic compounds are known to modulate $5\text{-}HT_{1A}$ receptors to impart complex physiological responses (Inserra et al., 2020, Pharmacol Rev 73: 202).

The term "modulating $5\text{-}HT_{1A}$ receptors", as used herein, refers to the ability of a compound disclosed herein to alter the function of $5\text{-}HT_{1A}$ receptors. A $5\text{-}HT_{1A}$ receptor modulator may activate the activity of a $5\text{-}HT_{1A}$ receptor, may activate or inhibit the activity of a $5\text{-}HT_{1A}$ receptor depending on the concentration of the compound exposed to the $5\text{-}HT_{1A}$ receptor, or may inhibit the activity of a $5\text{-}HT_{1A}$ receptor. Such activation or inhibition may be contingent on the occurrence of a specific event, such as activation of a signal transduction pathway, and/or maybe manifest only in particular cell types. The term "modulating $5\text{-}HT_{1A}$ receptors," also refers to altering the function of a $5\text{-}HT_{1A}$ receptor by increasing or decreasing the probability that a complex forms between a $5\text{-}HT_{1A}$ receptor and a natural binding partner to form a multimer. A $5\text{-}HT_{1A}$ receptor modulator may increase the probability that such a complex forms between the $5\text{-}HT_{1A}$ receptor and the natural binding partner, may increase or decrease the probability that a complex forms between the $5\text{-}HT_{1A}$ receptor and the natural binding partner depending on the concentration of the compound exposed to the $5\text{-}HT_{1A}$ receptor, and or may decrease the probability that a complex forms between the $5\text{-}HT_{1A}$ receptor and the natural binding partner.

The term "$5\text{-}HT_{1A}$ receptor-mediated disorder", as used herein, refers to a disorder that is characterized by abnormal $5\text{-}HT_{1A}$ receptor activity. A $5\text{-}HT_{1A}$ receptor-mediated disorder may be completely or partially mediated by modulating $5\text{-}HT_{1A}$ receptors. In particular, a $5\text{-}HT_{1A}$ receptor-mediated disorder is one in which modulation of $5\text{-}HT_{1A}$ receptors results in some effect on the underlying disorder e.g., administration of a $5\text{-}HT_{1A}$ receptor modulator results in some improvement in at least some of the subjects being treated.

The term "$5\text{-}HT_{1A}$ receptor-mediated disorder", as used herein, refers to a disorder that is characterized by abnormal $5\text{-}HT_{1A}$ receptor activity. A $5\text{-}HT_{1A}$ receptor-mediated disorder may be completely or partially mediated by modulating $5\text{-}HT_{1A}$ receptors. In particular, a $5\text{-}HT_{1A}$ receptor-mediated disorder is one in which modulation of $5\text{-}HT_{1A}$ receptors results in some effect on the underlying disorder e.g., administration of a $5\text{-}HT_{1A}$ receptor modulator results in some improvement in at least some of the subjects being treated.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may include an altered state of consciousness, satisfaction, pleasure, euphoria, perceptual distortion, or hallucination.

The term "effective amount", as used herein, refers to an amount of an active agent, pharmaceutical formulation, or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "psilocybin biosynthetic enzyme complement", as used herein, refers to one or more polypeptides which alone or together are capable of facilitating the chemical conversion of a psilocybin precursor compound and form another psilocybin precursor compound, or a nitrilated psilocybin derivative compound. A psilocybin biosynthetic enzyme complement can include, for example, a tryptophan synthase subunit B polypeptide, a tryptophan decarboxylase and/or a N-acetyl transferase.

The term "tryptophan synthase subunit B polypeptide" as used herein, refers to any and all enzymes comprising a sequence of amino acid residues which is (i) substantially identical to the amino acid sequences constituting any tryptophan synthase subunit B polypeptide set forth herein, including, for example, SEQ.ID NO: 9, or (ii) encoded by a nucleic acid sequence capable of hybridizing under at least moderately stringent conditions to any nucleic acid sequence encoding any tryptophan synthase subunit B polypeptide set forth herein, but for the use of synonymous codons.

The term "tryptophan decarboxylase" as used herein, refers to any and all enzymes comprising a sequence of amino acid residues which is (i) substantially identical to the amino acid sequences constituting any tryptophan decarboxylase polypeptide set forth herein, including, for example, SEQ.ID NO: 12, or (ii) encoded by a nucleic acid sequence capable of hybridizing under at least moderately stringent conditions to any nucleic acid sequence encoding any tryptophan decarboxylase set forth herein, but for the use of synonymous codons.

The term "N-acetyl transferase" as used herein, refers to any and all enzymes comprising a sequence of amino acid residues which is (i) substantially identical to the amino acid sequences constituting any N-acetyl transferase polypeptide set forth herein, including, for example, SEQ.ID NO: 5, or (ii) encoded by a nucleic acid sequence capable of hybridizing under at least moderately stringent conditions to any nucleic acid sequence encoding any N-acetyl transferase set forth herein, but for the use of synonymous codons.

The terms "nucleic acid sequence encoding tryptophan synthase subunit B polypeptide", as may be used interchangeably herein, refer to any and all nucleic acid sequences encoding a tryptophan synthase subunit B polypeptide, including, for example, SEQ.ID NO: 8. Nucleic acid sequences encoding a tryptophan synthase subunit B polypeptide further include any and all nucleic acid sequences which (i) encode polypeptides that are substantially identical to the tryptophan synthase subunit B polypeptide sequences set forth herein; or (ii) hybridize to any tryptophan synthase subunit B polypeptide nucleic acid sequences set forth herein under at least moderately stringent hybridization conditions or which would hybridize thereto under at least moderately stringent conditions but for the use of synonymous codons.

The terms "nucleic acid sequence encoding tryptophan decarboxylase", and "nucleic acid sequence encoding a tryptophan decarboxylase polypeptide", as may be used interchangeably herein, refer to any and all nucleic acid sequences encoding a tryptophan decarboxylase, including, for example, SEQ.ID NO: 11. Nucleic acid sequences encoding a tryptophan decarboxylase polypeptide further include any and all nucleic acid sequences which (i) encode polypeptides that are substantially identical to the tryptophan decarboxylase polypeptide sequences set forth herein; or (ii) hybridize to any tryptophan decarboxylase nucleic acid sequences set forth herein under at least moderately stringent hybridization conditions or which would hybridize thereto under at least moderately stringent conditions but for the use of synonymous codons.

The terms "nucleic acid sequence encoding N-acetyl transferase", and "nucleic acid sequence encoding an N-acetyl transferase polypeptide", as may be used interchangeably herein, refer to any and all nucleic acid sequences encoding an N-acetyl transferase, including, for example, SEQ.ID NO: 4. Nucleic acid sequences encoding an N-acetyl transferase polypeptide further include any and all nucleic acid sequences which (i) encode polypeptides that are substantially identical to the N-acetyl transferase polypeptide sequences set forth herein; or (ii) hybridize to any N-acetyl transferase nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence or a nucleoside sequence.

The term "polypeptide", as used herein in conjunction with a reference SEQ.ID NO, refers to any and all polypeptides comprising a sequence of amino acid residues which is (i) substantially identical to the amino acid sequence constituting the polypeptide having such reference SEQ.ID NO, or (ii) encoded by a nucleic acid sequence capable of hybridizing under at least moderately stringent conditions to any nucleic acid sequence encoding the polypeptide having such reference SEQ.ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ.ID NO, refers to any and all nucleic acid sequences encoding a polypeptide having such reference SEQ.ID NO. Nucleic acid sequences encoding a polypeptide, in conjunction with a reference SEQ.ID NO, further include any and all nucleic acid sequences which (i) encode polypeptides that are substantially identical to the polypeptide having such reference SEQ.ID NO; or (ii) hybridize to any nucleic acid sequences encoding polypeptides having such reference SEQ.ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5×sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ.ID NO: 2, refers to a polypeptide capable of performing the same function as the polypeptide set forth in SEQ.ID NO: 2. Functional variants include modified a polypeptide wherein, relative to a noted reference polypeptide, the modification includes a substitution, deletion or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine and valine, (iv) asparagine and glutamine, and (v) tryptophan, tyrosine and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The terms "substantially pure" and "isolated", as may be used interchangeably herein describe a compound, e.g., a psilocybin derivative, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., by chromatography, gel electrophoresis or HPLC analysis.

The term "recovered" as used herein in association with a chemical compound, refers to a more or less pure form of the chemical compound.

General Implementation

As hereinbefore mentioned, the present disclosure relates to psilocybin derivatives. In particular, the present disclosure provides novel nitrilated psilocybin derivatives. In general, the herein provided compositions exhibit functional properties which deviate from the functional properties of psilocybin. Thus, for example, the nitrilated psilocybin derivatives, can exhibit pharmacological properties which deviate from psilocybin. Furthermore, the nitrilated derivatives may psilocybin derivatives may exhibit physicochemical properties which differ from psilocybin. Thus, for example, nitrilated psilocybin derivatives may exhibit superior solubility in a solvent, for example, an aqueous solvent. The nitrilated psilocybin derivatives in this respect are useful in the formulation of pharmaceutical and recreational drug formulations. In one embodiment, the nitrilated psilocybin derivatives of the present disclosure can conveniently be chemically and/or biosynthetically produced. The practice of this method avoids the extraction of psilocybin from mushrooms and the performance of subsequent chemical reactions to achieve nitrilated derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of nitrilated psilocybin derivatives.

In what follows selected embodiments are described with reference to the drawings.

Initially example nitrilated psilocybin derivatives will be described. Thereafter example methods of using and making the nitrilated psilocybin derivatives will be described.

Accordingly, in one aspect the present disclosure provides derivatives of a compound known as psilocybin of which the chemical structure is shown in FIG. 1. The derivatives herein provided are, in particular, derivatives nitrilated derivatives including psilocybin derivatives possessing a nitrile group.

Thus, in one aspect, the present disclosure provides, in accordance with the teachings herein, in at least one embodiment, a chemical compound having the formula (I):

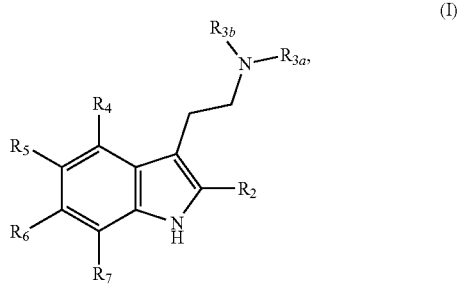

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group.

Thus, referring to the chemical compound having the formula (I), initially it is noted that, in an aspect hereof, at least one of $R_2$, $R_5$, $R_6$, or $R_7$ is a nitrile group.

In a further aspect, $R_2$, $R_5$, $R_6$, or $R_7$ can be a nitrile group wherein two, or at least two, hydrogen atoms are substituted by a nitrile group.

In a further aspect hereof, $R_{3A}$ and $R_{3B}$ can independently be a hydrogen atom, an alkyl group, an acyl group, or an aryl group. Thus, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can be each be an acyl group, or $R_{3A}$ and $R_{3B}$ can be each be an aryl group. Furthermore, one of $R_{3A}$ and $R_{3B}$ can be a hydrogen atom, and one of $R_{3A}$ and $R_{3B}$ can be an alkyl group. One of $R_{3A}$ and $R_{3B}$ can be a hydrogen atom, and one of $R_{3A}$ and $R_{3B}$ can be an acyl group. One of $R_{3A}$ and $R_{3B}$ can be a hydrogen atom, and one of $R_{3A}$ and $R_{3B}$ can be an aryl group. One of $R_{3A}$ and $R_{3B}$ can be an alkyl group, and one of $R_{3A}$ and $R_{3B}$ can be an aryl group. One of $R_{3A}$ and $R_{3B}$ can be an alkyl group, and one of $R_{3A}$ and $R_{3B}$ can be an acyl group. One of $R_{3A}$ and $R_{3B}$ can be an acyl group, and one of $R_{3A}$ and $R_{3B}$ can be an aryl group.

In a further aspect hereof, $R_4$ can be an O-alkyl group, an O-acyl group, a hydroxy group, a phosphate group, a glycosyloxy group, or a hydrogen atom.

In a further aspect hereof, the non-nitrilated groups $R_2$, $R_5$, $R_6$, or $R_7$ can be a hydrogen atom. Referring now to FIGS. 3A-3D, examples of nitrilated psilocybin derivatives in accordance herewith, wherein one of $R_2$, $R_5$, $R_6$, or $R_7$ are nitrilated, and the non-nitrilated groups $R_2$, $R_5$, $R_6$, or $R_7$ are hydrogen atoms are: the 2-nitrile-psilocybin derivative compound depicted in FIG. 3A, the 5-nitrile-psilocybin derivative depicted in FIG. 3B, the 6-nitrile-psilocybin derivative depicted in FIG. 3C, and the 7-nitrile-psilocybin derivative depicted in FIG. 3D.

Figure 4A:
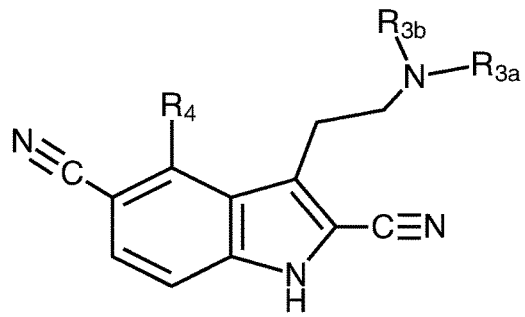
FIGS. 4A, 4B, 4C, 4D, 4E, 4F, 4G, 4H, 4I, 4J, and 4K depict the chemical structures of certain example nitrilated psilocybin derivatives, notably a 2,5-di-nitrile-psilocybin derivative (FIG. 4A), a 2,6-di-nitrile-psilocybin derivative (FIG. 4B), a 2,7-di-nitrile-psilocybin derivative (FIG. 4C), a 5,6-di-nitrile-psilocybin derivative (FIG. 4D), a 5,7-di-nitrile-psilocybin derivative (FIG. 4E), a 6,7-di-nitrile-psilocybin derivative (FIG. 4F), a 2,5,6-tri-nitrile-psilocybin derivative (FIG. 4G), a 2,5,7-tri-nitrile-psilocybin derivative (FIG. 4H), a 2,6,7-tri-nitrile-psilocybin derivative (FIG. 4I) a 5,6,7-tri-nitrile-psilocybin derivative (FIG. 4J), and a 2,5,6,7-tetra-nitrile-psilocybin derivative (FIG. 4K).
Figure 4B:
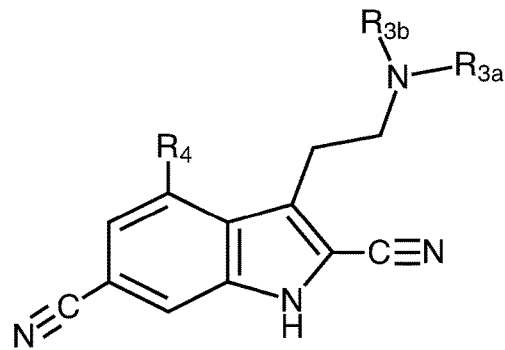
Figure 4C:
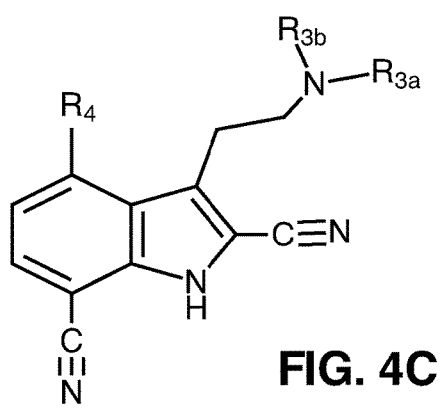
Figure 4D:
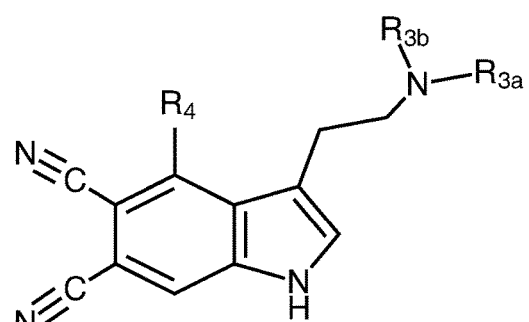
Figure 4E:
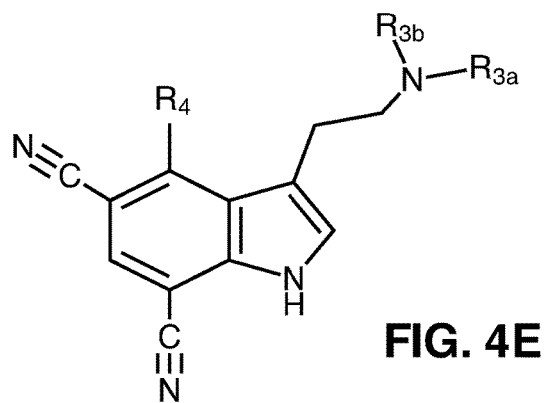
Figure 4F:
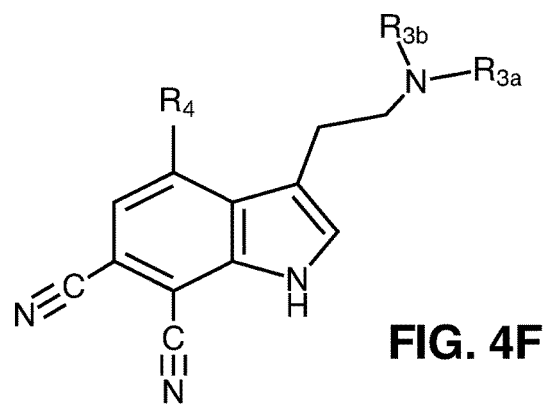

Referring now to FIGS. 4A-4F, examples of nitrilated psilocybin derivatives in accordance herewith, wherein two of $R_2$, $R_5$, $R_6$, or $R_7$ are nitrilated, and the non-nitrilated groups $R_2$, $R_5$, $R_6$, or $R_7$ are hydrogen atoms are: the 2,5-di-nitrile-psilocybin derivative compound depicted in FIG. 4A, the 2,6-di-nitrile-psilocybin derivative depicted in FIG. 4B, the 2,7-di-nitrile-psilocybin derivative depicted in FIG. 4C, the 5,6-di-nitrile-psilocybin derivative depicted in FIG. 4D, the 5,7-di-nitrile-psilocybin derivative depicted in FIG. 4E, and the 6,7-di-nitrile-psilocybin derivative depicted in FIG. 4F.

Figure 4G:
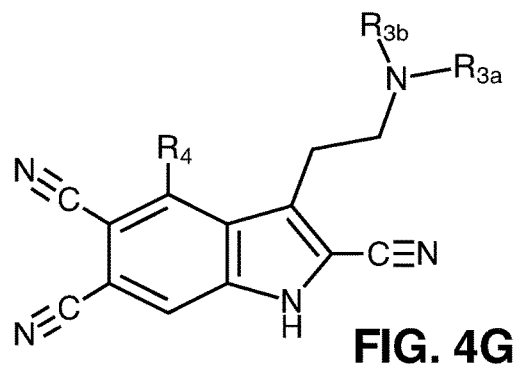
Figure 4H:
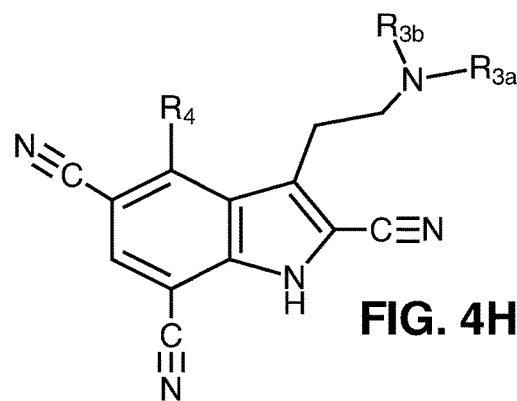
Figure 4I:
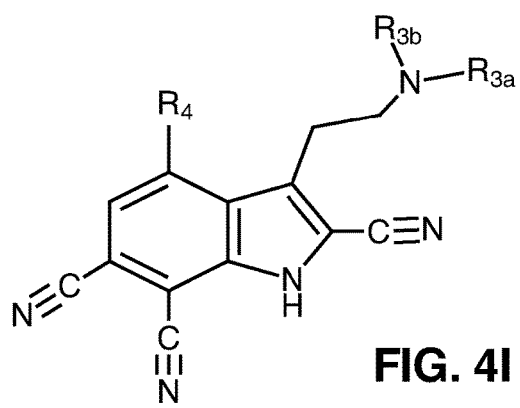
Figure 4J:
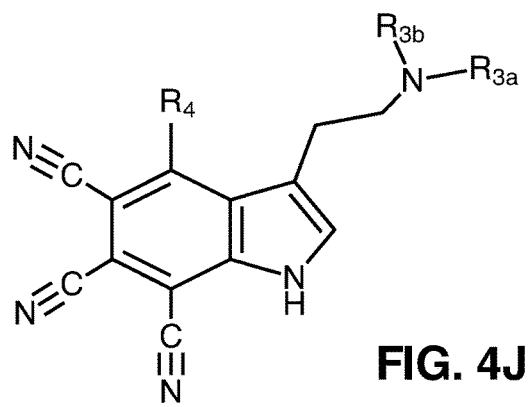

Referring now to FIGS. 4G-4J, examples of nitrilated psilocybin derivatives in accordance herewith, wherein three of $R_2$, $R_5$, $R_6$, or $R_7$ are nitrilated, and the non-nitrilated groups $R_2$, $R_5$, $R_6$, or $R_7$ are hydrogen atoms are: the 2,5,6-tri-nitrile-psilocybin derivative compound depicted in FIG. 4G, the 2,5,7-tri-nitrile-psilocybin derivative depicted in FIG. 4H, the 2,6,7-tri-nitrile-psilocybin derivative depicted in FIG. 4I, and the 5,6,7-tri-nitrile-psilocybin derivative depicted in FIG. 4J.

Figure 4K:
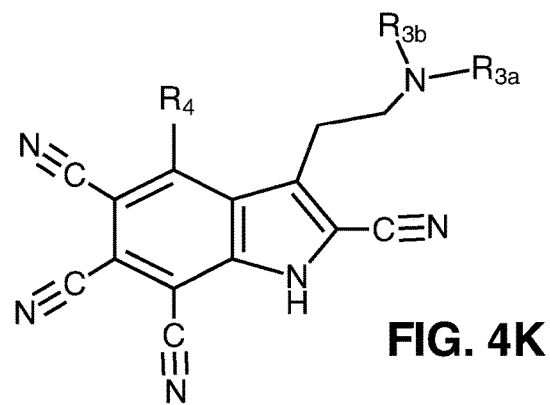

Referring now to FIG. 4K, an example of a nitrilated psilocybin derivative in accordance herewith, wherein all four of $R_2$, $R_5$, $R_6$, or $R_7$ are nitrilated is the 2,5,6,7-tetra-nitrile-psilocybin derivative depicted in FIG. 4K.

In a further aspect, $R_4$, can be an O-alkyl group. Referring now to FIGS. 5A, 5B, 6A, 6B, 7A, and 7B, examples of nitrilated psilocybin derivatives in accordance herewith, wherein $R_5$, and/or $R_7$ are nitrile groups and $R_4$ is an O-alkyl group are: the 4-O-methyl-5-nitrile-psilocybin derivative depicted in FIG. 5A, the 4-O-ethyl-5-nitrile-psilocybin derivative depicted in FIG. 5B, the 4-O-methyl-7-nitrile-psilocybin derivative depicted in FIG. 6A, the 4-O-ethyl-7-nitrile-psilocybin derivative depicted in FIG. 6B, the 4-O-methyl-5,7-di-nitrile-psilocybin derivative depicted in FIG. 7A, and the 4-O-ethyl-5,7-di-nitrile-psilocybin derivative depicted in FIG. 7B. It is noted that in these specific examples only 5-nitrile, 7-nitrile, and 5,7-di-nitrile-4-O-alkyl psilocybin derivatives are shown. Further examples of O-alkyl psilocybin derivatives included herein are any and all O-alkyl psilocybin derivatives which may be selected by referring to the chemical formulas shown in FIGS. 3A-3D and FIGS. 4A-4K, wherein $R_4$ is an O-alkyl group. It will thus be clearly understood that FIGS. 5A, 5B, 6A, 6B, 7A, and 7B represent examples only of nitrilated psilocybin derivatives having chemical formula (I) wherein non-nitrilated groups R$_2$, R$_5$, R$_6$, or R$_7$ are a hydrogen atom. Other nitrilated psilocybin derivatives wherein non-nitrilated groups R$_2$, R$_5$, R$_6$, or R$_7$ are a hydrogen atom can readily be selected, and thus are included in the O-alkylated nitrilated psilocybin derivatives compounds of the present disclosure.

In a further aspect, R$_4$, can be an O-acyl group. Referring now to FIGS. 5C, 5D, 6C, 6D, 7C, and 7D, examples of nitrilated psilocybin derivatives in accordance herewith, wherein R$_5$, and/or R$_7$ are nitrile groups and R$_4$ is an O-acyl group are: the 4-acetyl-5-nitrile-psilocybin derivative depicted in FIG. 5C, the 4-propanoyl-5-nitrile-psilocybin derivative depicted in FIG. 5D, the 4-acetyl-7-nitrile-psilocybin derivative depicted in FIG. 6C, the 4-propanoyl-7-nitrile-psilocybin derivative depicted in FIG. 6D, the 4-acetyl-5,7-di-nitrile-psilocybin derivative depicted in FIG. 7C, and the 4-propanoyl-5,7-di-nitrile-psilocybin derivative depicted in FIG. 7D. It is noted that in these specific examples only 5-nitrile, 7-nitrile, and 5,7-di-O-acyl psilocybin derivatives are shown. Further examples of O-acyl psilocybin derivatives included herein are any and all O-acyl psilocybin derivatives which may be selected by referring to the chemical formulas shown in FIGS. 3A-3D and FIGS. 4A-4K, wherein R$_4$ is an O-acyl group. It will thus be clearly understood that FIGS. 5C, 5D, 6C, 6D, 7C, and 7D represent examples only of O-acylated psilocybin derivatives having chemical formula (I) wherein non-nitrilated groups R$_2$, R$_5$, R$_6$, or R$_7$ are a hydrogen atom. Other nitrilated psilocybin derivatives wherein non-nitrilated groups R$_2$, R$_5$, R$_6$, or R$_7$ are a hydrogen atom can readily be selected, and thus are included in the nitrilated O-acylated psilocybin derivatives compounds of the present disclosure.

Figure 5E:
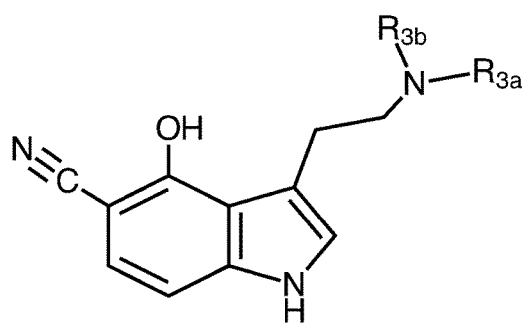

In a further aspect, R$_4$ can be a hydroxy group. Referring now to FIGS. 5E, 6E, and 7E, examples of nitrilated psilocybin derivatives in accordance herewith, wherein R$_5$, and/or R$_7$ are nitrile groups and are R$_4$ is a hydroxy group are: the 4-hydroxy-5-nitrile-psilocybin derivative depicted in FIG. 5E, the 4-hydroxy-7-nitrile-psilocybin derivative depicted in FIG. 6E, and the 4-hydroxy-5,7-di-nitrile-psilocybin derivative depicted in FIG. 7E. It is noted that in these specific examples only 5-nitrile, 7-nitrile, and 5,7-di-nitrile-psilocybin derivatives are shown. Further examples of hydroxy-psilocybin derivatives included herein are any and all hydroxy-psilocybin derivatives which may be selected by referring to the chemical formulas shown in FIGS. 3A-3D and FIGS. 4A-4K, wherein R$_4$ is a hydroxy group. It will thus be clearly understood that FIGS. 5E, 6E, and 7E represent examples only of hydroxy psilocybin derivatives having chemical formula (I) wherein non-nitrilated groups R$_2$, R$_5$, R$_6$, or R$_7$ are a hydrogen atom. Other nitrilated psilocybin derivatives wherein non-nitrilated groups R$_2$, R$_5$, R$_6$, or R$_7$ are a hydrogen atom can readily be selected, and thus are included in the nitrilated hydroxy psilocybin derivatives compounds of the present disclosure.

Figure 5F:
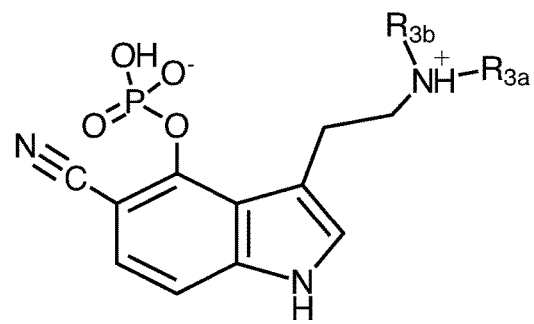

In a further aspect, R$_4$ can be a phosphate group. Referring now to FIGS. 5F, 6F, and 7F, examples of nitrilated psilocybin derivatives in accordance herewith, wherein R$_5$, and/or R$_7$ are nitrile groups and are R$_4$ is a phosphate group are: the 4-phospho-5-nitrile-psilocybin derivative depicted in FIG. 5F, the 4-phospho-7-nitrile-psilocybin derivative depicted in FIG. 6F, and the 4-phospho-5,7-di-nitrile-psilocybin derivative depicted in FIG. 7F. It is noted that in these specific examples only 5-nitrile, 7-nitrile, and 5,7-di-nitrile-psilocybin derivatives are shown. Further examples of phospho-psilocybin derivatives included herein are any and all phospho-psilocybin derivatives which may be selected by referring to the chemical formulas shown in FIGS. 3A-3D and FIGS. 4A-4K, wherein R$_4$ is a phosphate group. It will thus be clearly understood that FIGS. 5F, 6F, and 7F represent examples only of phospho psilocybin derivatives having chemical formula (I) wherein non-nitrilated groups R$_2$, R$_5$, R$_6$, or R$_7$ are a hydrogen atom. Other nitrilated psilocybin derivatives wherein non-nitrilated groups R$_2$, R$_5$, R$_6$ or R$_7$ are a hydrogen atom can readily be selected, and thus are included in the nitrilated phosphate psilocybin derivatives compounds of the present disclosure.

In a further aspect, R$_4$ can be a glycosyloxy group. Referring now to FIGS. 5G, 6G, and 7G, examples of nitrilated psilocybin derivatives in accordance herewith, wherein R$_5$, and/or R$_7$ are nitrile groups and are R$_4$ is a glycosyloxy group are: the 4-O-glycosyl-5-nitrile-psilocybin derivative depicted in FIG. 5G, the 4-O-glycosyl-7-nitrile-psilocybin derivative depicted in FIG. 6G, and the 4-O-glycosyl-5,7-di-nitrile-psilocybin derivative depicted in FIG. 7G. It is noted that in these specific examples only 5-nitrile, 7-nitrile, and 5,7-di-nitrile-psilocybin derivatives are shown. Further examples of glycosyl-psilocybin derivatives included herein are any and all glycosyl-psilocybin derivatives which may be selected by referring to the chemical formulas shown in FIGS. 3A-3D and FIGS. 4A-4K, wherein R$_4$ is a glycosyloxy group. It will thus be clearly understood that FIGS. 5G, 6G, and 7G represent examples only of glycosyloxy psilocybin derivatives having chemical formula (I) wherein non-nitrilated groups R$_2$, R$_5$, R$_6$, or R$_7$ are a hydrogen atom. Other nitrilated psilocybin derivatives wherein non-nitrilated groups R$_2$, R$_5$, R$_6$ or R$_7$ are a hydrogen atom can readily be selected, and thus are included in the nitrilated glycosyloxy psilocybin derivatives compounds of the present disclosure.

In a further aspect, R$_4$, can be a hydrogen atom. Referring now to FIGS. 5H, 6H, and 7H, examples of nitrilated psilocybin derivatives in accordance herewith, wherein R$_5$, and/or R$_7$ are nitrile groups and are R$_4$ is a hydrogen atom are: the 5-nitrile-psilocybin derivative depicted in FIG. 5H, the 7-nitrile-psilocybin derivative depicted in FIG. 6H, and the 5,7-di-nitrile-psilocybin derivative depicted in FIG. 7H. It is noted that in these specific examples only 5-nitrile, 7-nitrile, and 5,7-di-nitrile-hydro-psilocybin derivatives are shown. Further examples of hydro-psilocybin derivatives included herein are any and all psilocybin derivatives which may be selected by referring to the chemical formulas shown in FIGS. 3A-3D and FIGS. 4A-4K, wherein R$_4$ is a hydrogen atom. It will thus be clearly understood that FIGS. 5H, 6H, and 7H represent examples only of hydro psilocybin derivatives having chemical formula (I) wherein non-nitrilated groups R$_2$, R$_5$, R$_6$, or R$_7$ are a hydrogen atom. Other nitrilated psilocybin derivatives wherein non-nitrilated groups R$_2$, R$_5$, R$_6$, or R$_7$ are a hydrogen atom can readily be selected, and thus are included in the nitrilated hydro psilocybin derivatives compounds of the present disclosure.

Furthermore, in one embodiment, an aminated psilocybin derivative according to the present disclosure can be a chemical compound having the formulas (III), (IV), (V), (VI), (VII), (VIII), (IX), (X) or (XI):

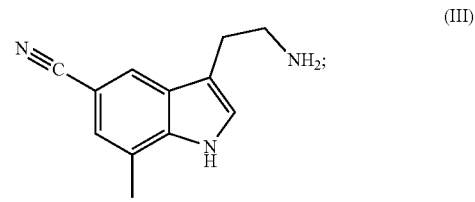

(III)

-continued

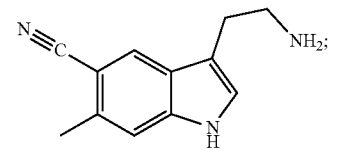
(IV)

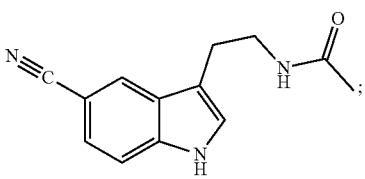
(V)

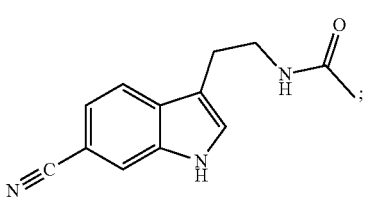
(VI)

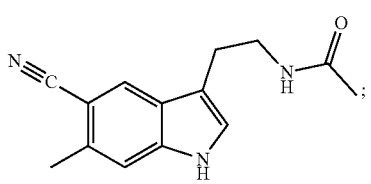
(VII)

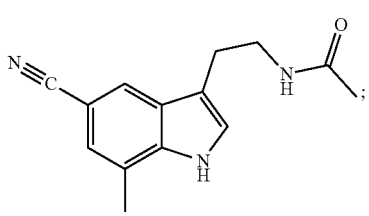
(VIII)

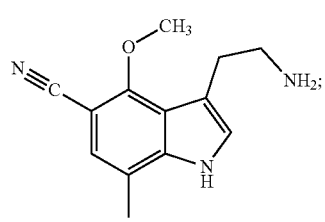
(IX)

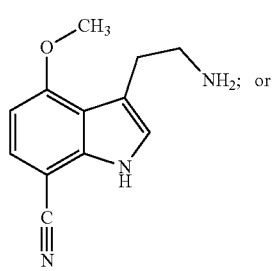
(X)

-continued

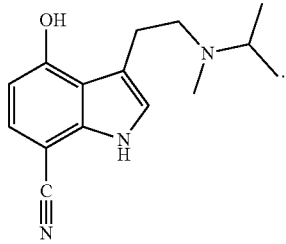
(XI)

In one embodiment, the alkyl groups (including O-alkyl, acyl and O-acyl) in any of the definitions of the Formulas of the disclosure is $C_1$-$C_{20}$-alkyl. In another embodiment, the alkyl group is $C_1$-$C_{10}$-alkyl. In another embodiment, the alkyl group is $C_1$-$C_6$-alkyl. In another embodiment, the alkyl group is methyl, ethyl, propyl, butyl or pentyl.

In one embodiment, the aryl groups in any of the definitions of the Formulas of the disclosure is optionally substituted $C_6$-$C_{14}$-aryl. In another embodiment, the aryl group is optionally substituted $C_6$-$C_{10}$-aryl, or phenyl. In another embodiment, the aryl group is phenyl, naphthyl, tetrahydronaphthyl, phenanthrenyl, biphenylenyl, indanyl, or indenyl and the like.

Furthermore, it is noted that the nitrilated psilocybin derivatives of the present disclosure include salts thereof, including pharmaceutically acceptable salts. Thus, the nitrogen atom of the ethyl-amino group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term nitrilated psilocybin derivative also includes compounds having the formula (XII):

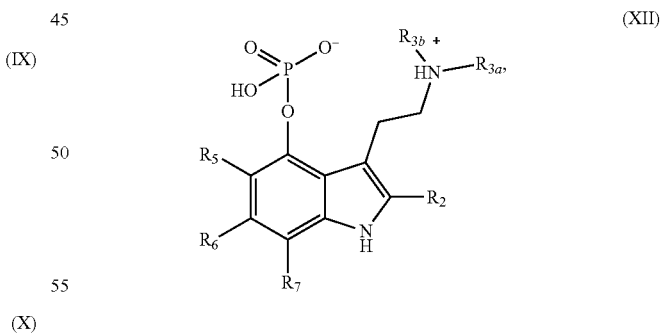
(XII)

wherein at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, and wherein $R_{3A}$ and $R_{3B}$ are a hydrogen atom, an alkyl group, acyl group or an aryl group. Further included are salts of nitrilated psilocybins having the formula (XII), such as a sodium salt, a potassium salt etc.

Thus, to briefly recap, the present disclosure provides nitrilated psilocybin derivatives. The disclosure provides, in particular, a chemical compound having the formula (I):

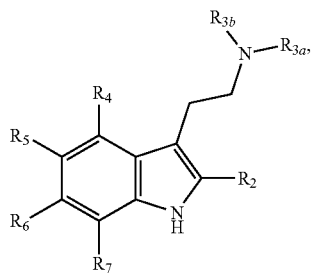

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group.

In one embodiment, at least one of $R_2$, $R_4$, $R_5$, $R_6$, or $R_7$ is a nitrile group, and wherein each non-nitrilated $R_2$, $R_5$, $R_6$, or $R_7$ is a hydrogen atom or a $(C_1$-$C_{20})$-alkyl group or $(C_1$-$C_{20})$—O-alkyl group. In another embodiment, each non-nitrilated $R_2$, $R_5$, $R_6$, or $R_7$ is a hydrogen atom, a methyl group, ethyl group, a propyl group, an O-methyl group, an O-ethyl group, or an O-propyl group.

In another embodiment, each non-nitrilated $R_2$, $R_5$, $R_6$, or $R_7$ is a hydrogen atom or a $(C_1$-$C_{10})$-alkyl group or $(C_1$-$C_{10})$—O-alkyl group. In another embodiment, each non-nitrilated $R_2$, $R_5$, $R_6$, or $R_7$ is a hydrogen atom, a methyl group, ethyl group, a propyl group, an O-methyl group, an O-ethyl group, or an O-propyl group.

In another embodiment, when $R_4$ is not nitrilated, $R_4$ is a hydrogen atom, a $(C_1$-$C_{20})$-alkyl group or $(C_1$-$C_{20})$—O-alkyl group, a hydroxy group, a glycosyloxy group, or a phosphate group. In another embodiment, when $R_4$ is not nitrilated, $R_4$ is a hydrogen atom, a $(C_1$-$C_{10})$-alkyl group or $(C_1$-$C_{10})$—O-alkyl group, a hydroxy group, a glycosyloxy group, or a phosphate group. In another embodiment, when $R_4$ is not nitrilated, $R_4$ is a hydrogen atom, a $(C_1$-$C_6)$-alkyl group or $(C_1$-$C_6)$—O-alkyl group, a hydroxy group, a glycosyloxy group, or a phosphate group. In another embodiment, when $R_4$ is not nitrilated, $R_4$ is a hydrogen atom, a methyl group, an ethyl group, a propyl group, a glycosyloxy group, a phosphate group, an O-methyl group, an O-ethyl group, or an O-propyl group.

In another embodiment, $R_{3A}$ and $R_{3B}$ are a hydrogen atom, a $(C_1$-$C_{20})$-alkyl group, a $(C_6$-$C_{14})$-aryl group, or a —C(=O)$(C_1$-$C_{20})$-alkyl group. In another embodiment, $R_{3A}$ and $R_{3B}$ are a hydrogen atom, a $(C_1$-$C_{10})$-alkyl group, a $(C_6$-$C_{10})$-aryl group, or a —C(=O)$(C_1$-$C_{10})$-alkyl group. In another embodiment, $R_{3A}$ and $R_{3B}$ are a hydrogen atom, a $(C_1$-$C_5)$-alkyl group, a phenyl group, or a —C(=O)$(C_1$-$C_6)$-alkyl group. In another embodiment, $R_{3A}$ and $R_{3B}$ are a hydrogen atom, a methyl group, an ethyl group, a propyl group, a phenyl group, —C(=O)—CH$_3$, —C(=O)—CH$_2$CH$_3$, or —C(=O)—CH$_2$CH$_2$CH$_3$.

In one embodiment of the disclosure, a chemical compound or salt thereof having formula (I) is included:

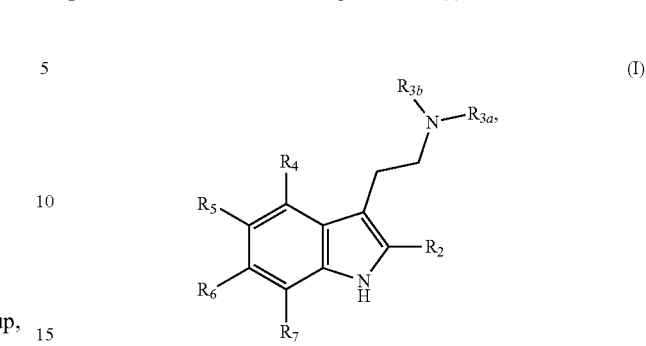

(I)

wherein $R_2$, $R_5$, $R_6$, and $R_7$ are independently or simultaneously H, an alkyl group, or O-alkyl group or a nitrile group, $R_{3A}$ and $R_{3B}$ are a hydrogen atom, an alkyl group, an aryl group, or an acyl group; and $R_4$ is hydrogen atom, alkyl group or O-alkyl group, a nitrile group, a hydroxy group, a glycosyloxy group, or a phosphate group; wherein at least one of $R_2$, $R_4$, $R_5$, $R_6$, and $R_7$ is a nitrile group.

In one embodiment, $R_2$, $R_5$, $R_6$, and $R_7$ are independently or simultaneously H, $(C_1$-$C_{20})$-alkyl group or $(C_1$-$C_{20})$—O-alkyl group or a nitrile group. In one embodiment, $R_2$, $R_5$, $R_6$, and $R_7$ are independently or simultaneously H, $(C_1$-$C_{10})$-alkyl group or $(C_1$-$C_{10})$—O-alkyl group or a nitrile group. In one embodiment, $R_2$, $R_5$, $R_6$, and $R_7$ are independently or simultaneously H, $(C_1$-$C_6)$-alkyl group or $(C_1$-$C_6)$—O-alkyl group or a nitrile group. In one embodiment, $R_2$, $R_5$, $R_6$, and $R_7$ are independently or simultaneously H, methyl, ethyl, propyl, O-methyl, O-ethyl, O-propyl, or a nitrile group.

In one embodiment, $R_4$ is H, $(C_1$-$C_{20})$-alkyl group or $(C_1$-$C_{20})$—O-alkyl group, a nitrile group, a glycosyloxy group, or a phosphate group. In one embodiment, $R_4$ is H, $(C_1$-$C_{10})$-alkyl group or $(C_1$-$C_{10})$—O-alkyl group, a nitrile group, a glycosyloxy group, or a phosphate group. In one embodiment, $R_4$ is H, $(C_1$-$C_6)$-alkyl group or $(C_1$-$C_6)$—O-alkyl group, a glycosyloxy group, a hydroxy group, or a phosphate group. In one embodiment, $R_4$ is H, methyl, ethyl, propyl, O-methyl, O-ethyl, O-propyl, a nitrile group, a glycosyloxy group, a hydroxy group, or a phosphate group.

In another embodiment, $R_{3A}$ and $R_{3B}$ are a hydrogen atom, a $(C_1$-$C_{20})$-alkyl group, a $(C_6$-$C_{14})$-aryl group, or a —C(=O)$(C_1$-$C_{20})$-alkyl group. In another embodiment, $R_{3A}$ and $R_{3B}$ are a hydrogen atom, a $(C_1$-$C_{10})$-alkyl group, a $(C_6$-$C_{10})$-aryl group, or a —C(=O)$(C_1$-$C_{10})$-alkyl group or O-alkyl group. In another embodiment, $R_{3A}$ and $R_{3B}$ are a hydrogen atom, a $(C_1$-$C_6)$-alkyl group, a phenyl group, or a —C(=O)$(C_1$-$C_6)$-alkyl group. In another embodiment, $R_{3A}$ and $R_{3B}$ are a hydrogen atom, a methyl group, an ethyl group, a propyl group, a phenyl group, —C(=O)—CH$_3$, —C(=O)—CH$_2$CH3, or —C(=O)—CH$_2$CH$_2$CH$_3$.

The nitrilated psilocybin derivatives of the present disclosure may be used to prepare a pharmaceutical or recreational drug formulation. Thus, in one embodiment, the present disclosure further provides, in another aspect, pharmaceutical and recreational drug formulations comprising nitrilated psilocybin derivatives. Accordingly, in one aspect, the present disclosure provides in a further embodiment a pharmaceutical or recreational drug formulation comprising a chemical compound having the formula (I):

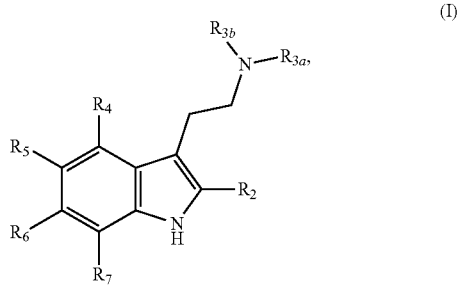

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group, together with a diluent, carrier, or excipient.

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patients physician or care giver it may be necessary to deviate upward or downward from the doses described herein.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the nitrilated psilocybin compound together with an excipient. The term "excipient" as used herein means any ingredient other than the chemical compound of the disclosure. As will readily be appreciated by those of skill in art, the selection of excipient may depend on factors such as the particular mode of administration, effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The pharmaceutical and drug formulations comprising the nitrilated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the nitrilated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90%

(w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the nitrilated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the nitrilated psilocybin derivatives of the present disclosure for parenteral administration may be formulated to be immediate and/or modified release. Modified release formulations include delayed-, sustained-, pulsed-, controlled-, targeted and programmed release. Thus, the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e., dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

In further embodiments, in which the nitrilated psilocybin derivative compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

Thus, it will be clear that the nitrilated psilocybin derivative compounds may be used as a pharmaceutical or recreational drug. Accordingly, in another aspect the present disclosure provides, in at least one embodiment, a use of a chemical compound having the formula (I):

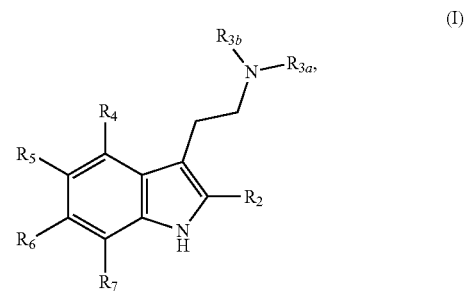

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group, together with a diluent, carrier, or excipient as a pharmaceutical or recreational drug formulation.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound having the formula (I):

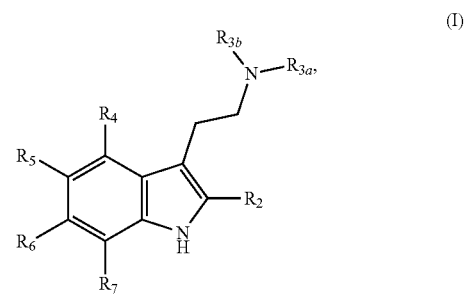

(I)

wherein, at least one of $R_2$, $R_5$, $R_6$, or $R_7$ is a nitrile group, and wherein each non-nitrilated $R_2$, $R_5$, $R_6$, or $R_7$ is a hydrogen atom or an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group, together with a diluent, carrier or excipient.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a $5\text{-HT}_{2A}$ receptor to thereby modulate the $5\text{-HT}_{2A}$ receptor. Such contacting includes bringing a compound of the present disclosure and $5\text{-HT}_{2A}$ receptor together under in vitro conditions, for example, by introducing the compounds in a sample containing a $5\text{-HT}_{2A}$ receptor, for example, a sample containing purified $5\text{-HT}_{2A}$ receptors, or a sample containing cells comprising $5\text{-HT}_{2A}$ receptors. In vitro conditions further include the conditions described in Example 1 hereof. Contacting further includes bringing a compound of the present disclosure and $5\text{-HT}_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent or excipient, as hereinbefore described, to thereby treat the subject. Upon having contacted the $5\text{-HT}_{2A}$ receptor, the compound may activate the $5\text{-HT}_{2A}$ receptor or inhibit the $5\text{-HT}_{2A}$ receptor.

In an aspect, the compounds of the present disclosure may be used to be contacted with a $5\text{-HT}_{1A}$ receptor to thereby modulate the $5\text{-HT}_{1A}$ receptor. Such contacting includes bringing a compound of the present disclosure and $5\text{-HT}_{1A}$ receptor together under in vitro conditions, for example, by introducing the compounds in a sample containing a $5\text{-HT}_{1A}$ receptor, for example, a sample containing purified $5\text{-HT}_{1A}$ receptors, or a sample containing cells comprising $5\text{-HT}_{1A}$ receptors. In vitro conditions further include the conditions described in Example 1 hereof. Contacting further includes bringing a compound of the present disclosure and $5\text{-HT}_{1A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent, or excipient, as hereinbefore described, to thereby treat the subject. Upon having contacted the $5\text{-HT}_{2A}$ receptor, the compound may activate the $5\text{-HT}_{1A}$ receptor or inhibit the $5\text{-HT}_{1A}$ receptor.

Thus, in a further aspect, the condition that may be treated in accordance herewith can be any $5\text{-HT}_{2A}$ receptor mediated disorder. Such disorders include, but are not limited to schizophrenia, psychotic disorder, attention deficit hyperactivity disorder, autism, and bipolar disorder.

Thus, in a further aspect, the condition that may be treated in accordance herewith can be any $5\text{-HT}_{1A}$ receptor mediated disorder. Such disorders include, but are not limited to schizophrenia, psychotic disorder, attention deficit hyperactivity disorder, autism, and bipolar disorder.

Turning now to methods of making the nitrilated psilocybin derivatives of the present disclosure, it is initially noted that the nitrilated psilocybin derivatives of the present disclosure may be prepared in any suitable manner, including by any organic chemical synthesis methods, biosynthetic methods, or a combination thereof.

One suitable method of making the nitrilated psilocybin derivatives of the present disclosure initially involves selecting and obtaining or preparing a reactant psilocybin derivative compound that can be converted into the nitrilated psilocybin derivatives of the present disclosure.

In some embodiments, the reactant psilocybin derivative may include a nitrogen containing group such as a primary amide, an oxime or a diazonium, which is dehydrated to form a nitrile.

In some embodiments, the reactant psilocybin derivative may be reacted with a nitrogen containing compound, such as ammonium, ammonia or hydroxyamine, for example.

In some embodiments, the reactant psilocybin derivative may be reacted with a nitrile containing compound, such as cyanogen bromide, or cyanogen chloride, for example.

Suitable reactant psilocybin derivative compounds include compounds comprising an indole prototype structure (see: FIG. 2), including, for example, a chemical compound having formula (II)

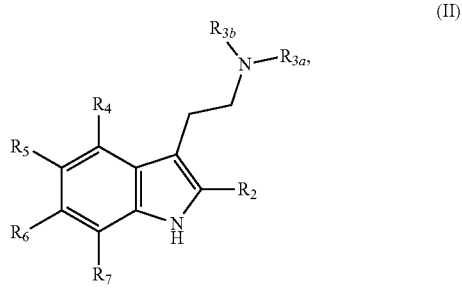

(II)

wherein, at least one of $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group. Reactant psilocybin derivative compound (II) comprises a plurality of compounds, some examples of which will next be described.

Figure 8A:
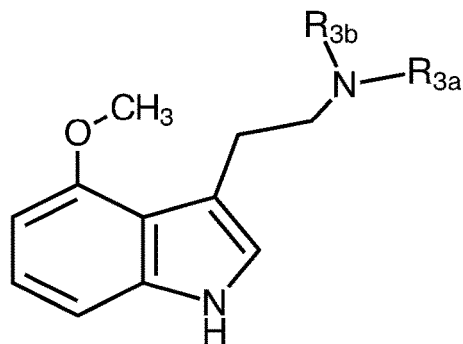
FIGS. 8A, 8B, 8C, 8D, 8E, 8F, 8G and 8H depict the chemical structures of certain example psilocybin derivatives, notably O-alkylated psilocybin derivatives, notably a 4-O-methyl-psilocybin derivative (FIG. 8A), a 4-O-ethyl-psilocybin derivative (FIG. 8B), a 4-acetyl-psilocybin derivative (FIG. 8C), a 4-propanoyl-psilocybin derivative (FIG. 8D), a 4-hydroxy-psilocybin derivative, a chemical compound also known as psilocin when $R_{3A}$ and $R_{3B}$ each are each a methyl group (FIG. 8E), a 4-phospho-psilocybin derivative (FIG. 8F), a 4-glycosyl-psilocybin derivative (FIG. 8G), and a psilocybin derivative (FIG. 8H).
Figure 8B:
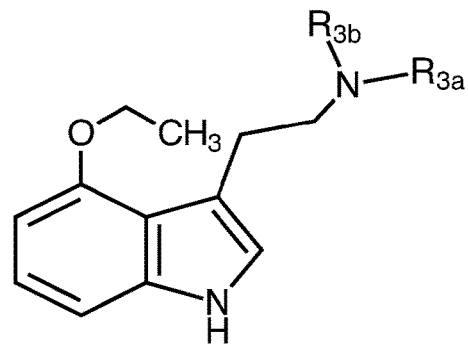

In one example embodiment, the reactant psilocybin derivative can be selected to be a chemical compound wherein $R_4$ is an O-alkyl group, $R_2$, $R_5$, $R_6$, and $R_7$ are a hydrogen atom, and $R_{3A}$ and $R_{3B}$ are a hydrogen atom, an alkyl group, an acyl group or an aryl group, such as, for example, the reactant psilocybin derivative shown in FIGS. 8A and 8B.

Figure 8C:
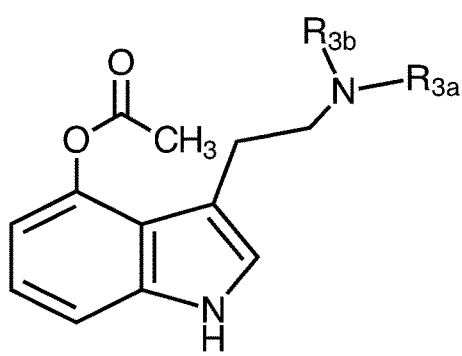
Figure 8D:
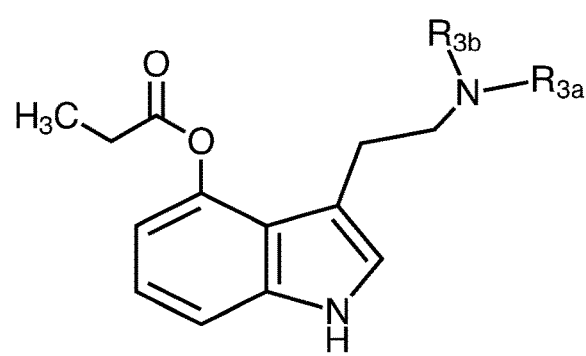

In one example embodiment, the reactant psilocybin derivative can be selected to be a chemical compound wherein $R_4$ is an O-acyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIGS. 8C and 8D.

Figure 8E:
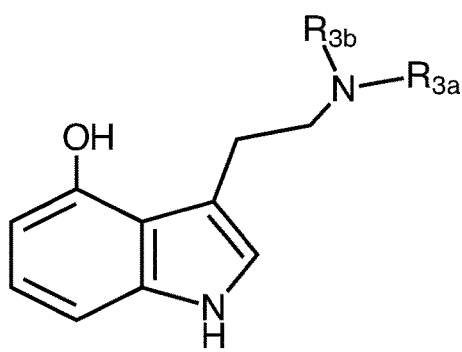

In one example embodiment, the reactant psilocybin derivative can be selected to be a chemical compound wherein $R_4$ is a hydroxyl group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 8E.

Figure 8F:
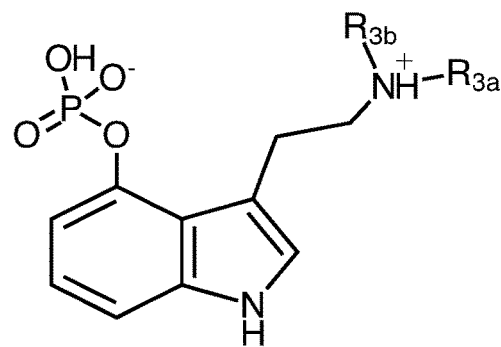

In one example embodiment, the reactant psilocybin derivative can be selected to be a chemical compound wherein $R_4$ is a phosphate group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 8F.

Figure 8G:
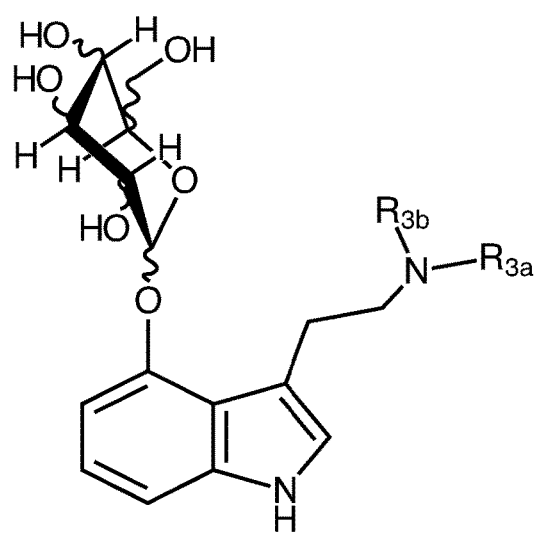

In one example embodiment, the reactant psilocybin derivative can be selected to be a chemical compound wherein $R_4$ is a glycosyloxy group, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 8G.

Figure 8H:
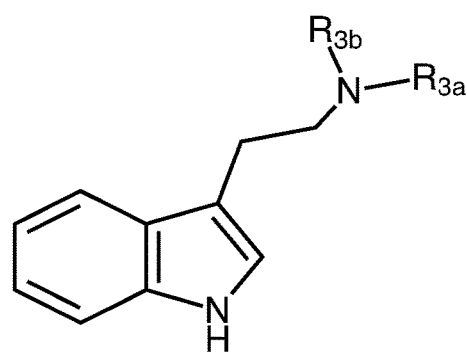

In one example embodiment, the reactant psilocybin derivative can be selected to be a chemical compound wherein $R_4$ is a hydrogen atom, $R_2$, $R_5$, $R_6$, and $R_7$ are a hydrogen atom, and $R_{3A}$ and $R_{3B}$ are a hydrogen atom, an alkyl group, an acyl group, or an aryl group, such as, for example, the reactant psilocybin derivative shown in FIG. 8H.

The reactant psilocybin derivative compounds may be provided in a more or less chemically pure form, for example, in the form of a psilocybin derivative preparation having a purity of at least about 95%, at least about 96%, at least about 97%, at least about 98%, at least about 99%, or at least 99.9%. The psilocybin derivative may be chemically synthesized, or obtained from a fine chemical manufacturer.

A nitrile group containing compound may be provided in a more or less chemically pure form, for example, having a purity of at least about 95%, at least about 96%, at least about 97%, at least about 98%, at least about 99%, or at least 99.9%. The nitrile containing compound may be synthesized or purified, or can be conveniently obtained from a fine chemical manufacturer.

Thus, initially, in an aspect hereof, a reactant psilocybin derivative is provided, and the reactant psilocybin derivative is employed to react in a chemical reaction resulting in the formation of a nitrilated psilocybin derivatives.

Figure 9A:
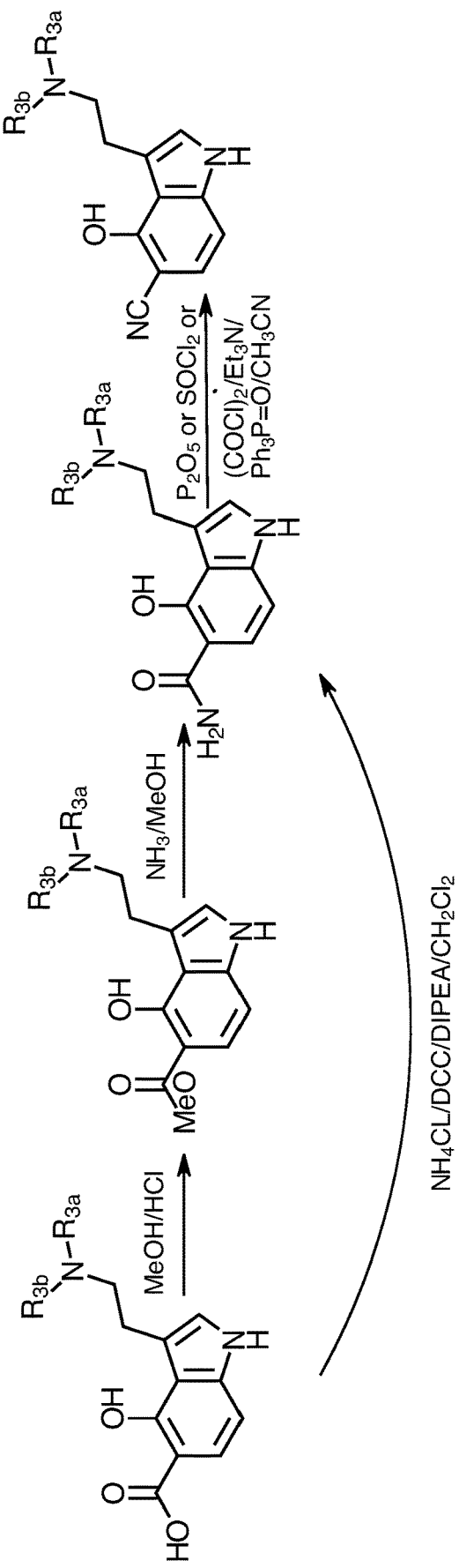
FIGS. 9A, 9B, 9C, 9D and 9E depict examples of chemical reactions showing the formation of nitrilated psilocybin derivatives, notably the formation of a 5-nitrile psilocybin derivative using a 5-carboxy-4-hydroxy-psilocybin derivative as a reactant (FIG. 9A), the formation of a 7-nitrile psilocybin derivative using a 7-formyl-4-hydroxy-psilocybin derivative as a reactant (FIG. 9B), the formation of a 5-nitrile psilocybin derivative using a 5-amino-4-hydroxy-psilocybin derivative as a reactant (FIG. 9C), the formation of a 5,7-nitrile psilocybin derivative using a 5,7-carboxy-4-hydroxy-psilocybin derivative as a reactant (FIG. 9D), and the formation of 5-nitrile psilocybin derivative using a 4-hydroxy psilocybin as a reactant (FIG. 9E).
Figure 9B:
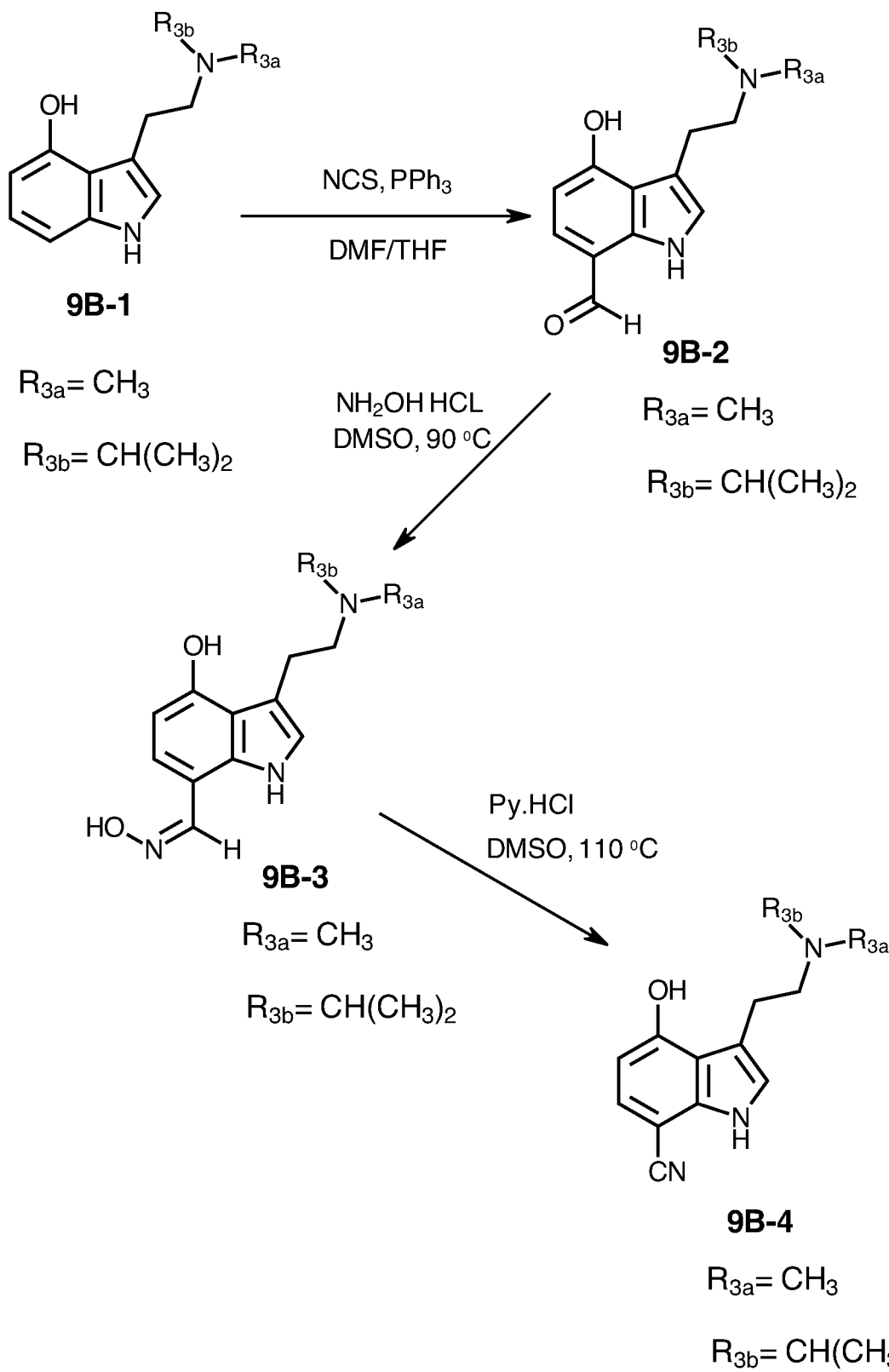
Figure 9C:
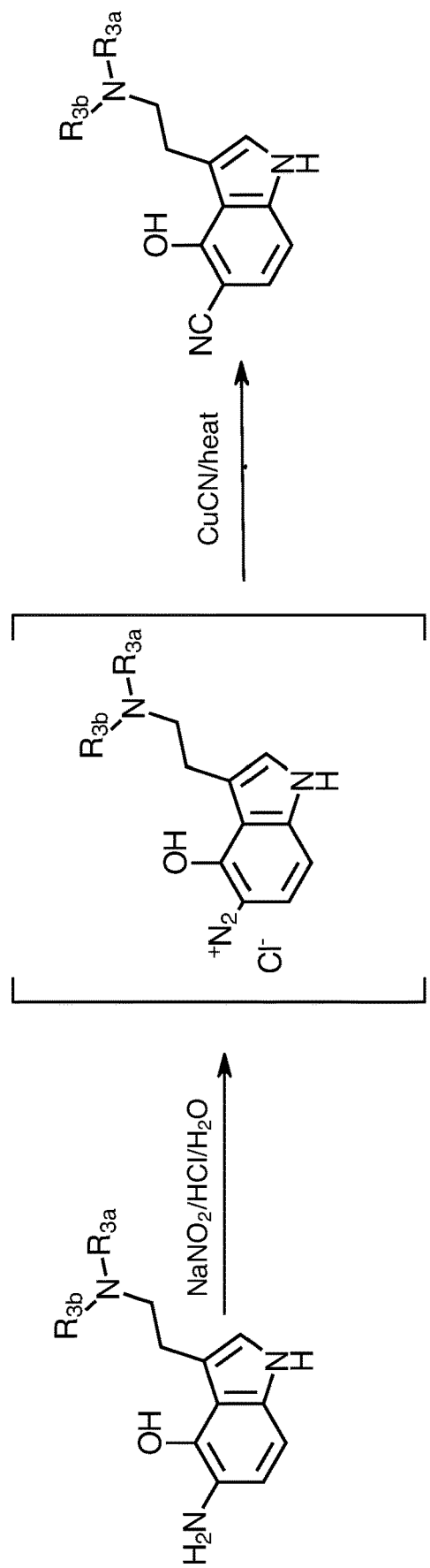

Referring now to FIGS. 9A-9C, shown therein are example syntheses to a 5-mononitrilated psilocybin derivative. In particular, FIGS. 9A and 9C show an example chemical reactions wherein a 5-nitrile-4-hydroxy-psilocybin derivative (FIG. 5E) is formed, using either a 5-carboxy-4-hydroxy-psilocybin derivative (FIG. 9A) or a 5-amino-4-hydroxy-psilocybin derivative (FIG. 9C) as a reactant. FIG. 9B shows an example of multistep synthesis of 7-nitrile-4-hydroxy-psilocybin derivative (9B-4, $R_{3a}$=$CH_3$, $R_{3b}$=$CH(CH_3)_2$) using a 4-hydroxy-psilocybin derivative (9B-1, $R_{3a}$=$CH_3$, $R_{3b}$=$CH(CH_3)_2$) as a starting material. The synthesis can be started with a regioselective formylation at 7-position of 4-hydroxy-psilocybin derivative (9B-1, $R_{3a}$=$CH_3$, $R_{3b}$=$CH(CH_3)_2$) using N-chlorosuccinimide-triphenylphosphine-N,N-dimethyl formamide (DMF) as a reagent, to provide the corresponding 7-formyl-4-hydroxy-psilocybin derivative (9B-2, $R_{3a}$=$CH_3$, $R_{3b}$=$CH(CH_3)_2$). The 7-formyl group can subsequently be converted to the desired 7-nitrile group via the condensation of the 7-formyl group with hydroxyamine hydrochloride salt to first obtain the 7-oxime-functionalized intermediate (9B-3, $R_{3a}$=$CH_3$, $R_{3b}$=$CH(CH_3)_2$); a further dehydration of the 7-oxime-functionality in dimethylsulfoxide (DMSO) at 110° C. under the catalysis of pyridinium chloride can then furnish the desired 7-nitrile-4-hydroxy-psilocybin derivative (9B-4, $R_{3a}$=$CH_3$, $R_{3b}$=$CH(CH_3)_2$) (See: S. T. Chill and R. C. Mebane, Syn. Commun., 39, 3601-3606, 2009).

Referring to FIG. 9A, for example, using 5-carboxy-4-hydroxy-psilocybin derivative as a starting reactant, the corresponding 5-primary amide can be directly formed via the reaction with ammonium chloride with the help of N,N'-dicyclohexylcarbodiimide (DCC) in the presence of N,N-diisopropylethylamine (DIPEA) (see: W. Wang, J. S. McMurray, Tetrahedr. Lett., 1999, 40, 2501-2504). Alternatively, the same primary amide can be synthesized from the 5-carboxy group psilocybin derivative compound via a first esterification in an alcohol (such as methanol) under acidic conditions followed by an aminolysis. Thereafter, the 5-primary amide psilocybin derivative can be transformed to the desired cyanide (FIG. 5E) via a dehydration step under various conditions, for example using phosphorus pentoxide ($P_2O_5$) orthionyl chloride ($SOCl_2$) as a dehydrating reagent. Yet further alternative conditions, such as a combination of oxalyl chloride ($COCl_2$)-triphenylphosphine oxide ($Ph_3P$=O)-triethylamine ($Et_3N$) (see: R. Ding et al, J. Org. Chem., 2018, 83, 12939-12944) can also be selected to achieve dehydration.

Referring to FIG. 9B, using 5-formyl-4-hydroxy-psilocybin derivative as a reactant, an intermediate oxime can be formed after a condensation with hydroxyamine, and the formed oxime can be dehydrated with the help of reagents such as oxalyl chloride-dimethyl sulfoxide-triethylamine (see: S. A. Shipilovskikh, et al, Org. Lett. 2018, 20, 3, 728-731) or trifluoroacetic anhydride (see: N. Uludag, Russ. J. Org. Chem. 56(9), 1640-1645, 2020) or titanium tetrachloride (see: A. Leggio, E. L. Belsito, S. Gallo, A. Liguori, Tetrahedron Lett., 58(15), 1512-1514, 2017).

Referring to FIG. 9C, another method that may be used involves using 5-amino-4-hydroxy-psilocybin derivative as a starting reactant. The 5-amino group can be converted to an intermediate 5-diazonium salt via an N-nitrosation, using a nitrite salt, for example, sodium nitrite or potassium nitrite, and subsequently substituting the formed 5-diazonium salt with a salt of cyanide as a reagent, such as copper cyanide.

Figure 9D:
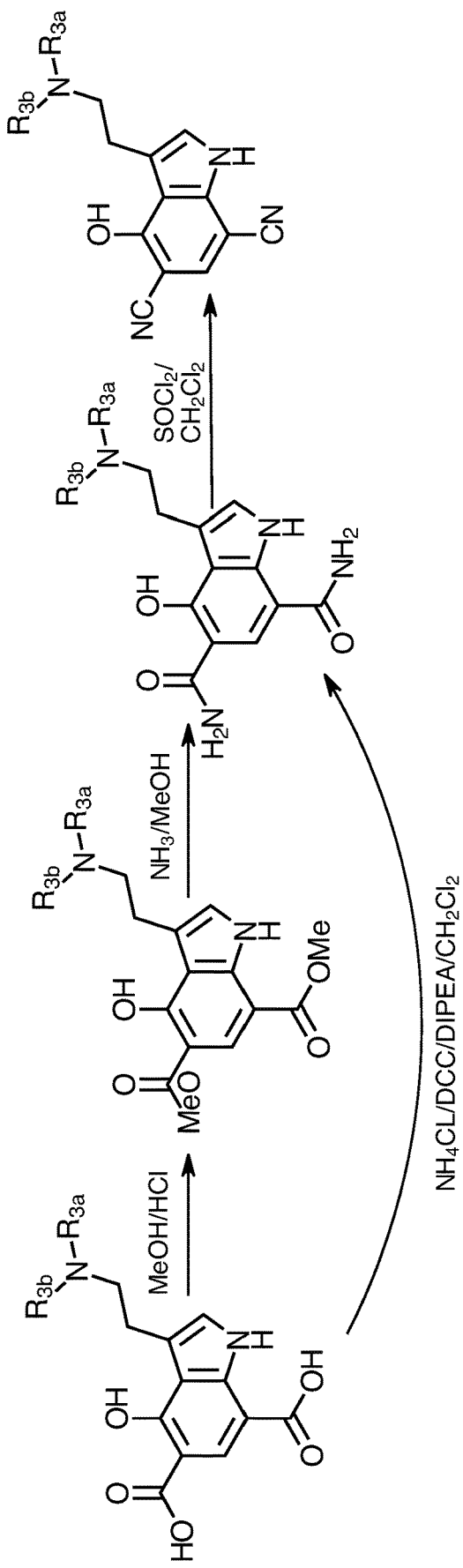

FIG. 9D depicts an example of synthesis of psilocybin derivatives containing two nitrile groups at both the $C_5$ and $C_7$ carbon atoms (FIG. 7E). For example, using a 5,7-dicarboxy-4-hydroxy-psilocybin derivative as a reactant, the corresponding 5,7-dinitrile-4-hydroxy-psilocybin derivative can be obtained via the direct method, analogous to the method described above with respect to the mononitrilated 5-nitrile-4-hydroxy derivative (see: FIG. 9A), using ammonium chloride/DCC/DIPEA or indirect method by first carrying out a diesterification in acidic methanol and subsequently an aminolysis on both ester sites to afford the 5,7-diamide. In a final step, the desired 5,7-dinitrile psilocybin derivative (FIG. 7E) can be synthesized via a dehydration step with the help of thionyl chloride, or other reagents as shown in FIG. 9D, and as further hereinbefore described with respect using a 5-carboxy-4-hydroxy-psilocybin to form the mononitrilated 5-nitrile-4-hydroxy derivative (see: FIG. 9A).

Figure 9E:
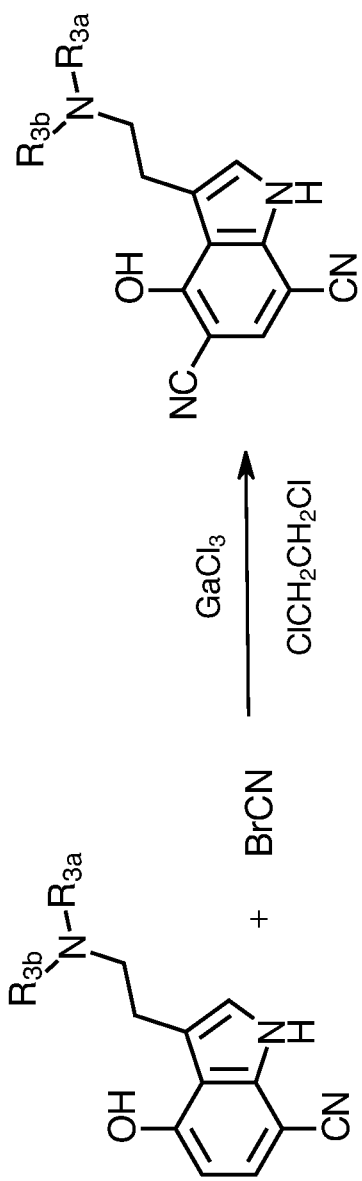

Referring now to FIG. 9E, other methods may involve direct cyanation of the aromatic C—H bonds of the psilocybin derivative, using a nitrile containing compound, such as cyanogen bromide. For example, a 4-hydroxy psilocybin derivative may be directly nitrilated using cyanogen bromide in a gallium catalyzed reaction in the presence of ethylene dichloride (see: K. Okamoto, et al, Chem. Commun., 2012, 48, 3127-3129).

Other methods may involve the use of psilocybin derivatives containing different functional groups such as halides, as reactive psilocybin compounds.

Thus, it will now be clear that, in an aspect hereof, the reactant psilocybin derivatives disclosed herein may be converted to nitrilated psilocybin derivatives using one of the methods described above. Thus, in addition to reactant psilocybin derivative shown in FIG. 8E, the example reactant psilocybin derivatives shown in FIGS. 8B-8H may also be converted to a nitrilated psilocybin derivative using one of the methods disclosed in the present disclosure. The 4-O-methyl-psilocybin derivative depicted an FIG. 8A may be reacted to form, for example, the 4-O-methyl-5-nitrile-psilocybin derivative depicted in FIG. 5A (as already noted), the 4-O-methyl-7-nitrile-psilocybin derivative depicted in FIG. 6A, or the 4-O-methyl-5,7-di-nitrile-psilocybin depicted in FIG. 7A.

Figure 5A:
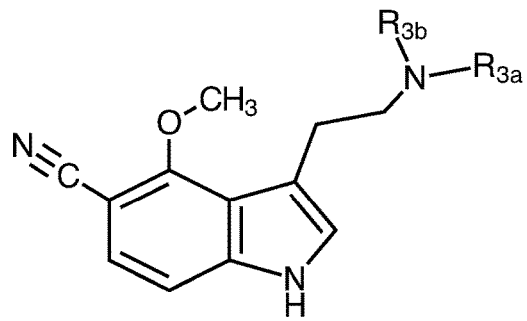
FIGS. 5A, 5B, 5C, 5D, 5E, 5F, 5G and 5H depict the chemical structures of certain example nitrilated psilocybin derivatives, notably O-alkylated nitrilated psilocybin derivatives, notably a 4-O-methyl-5-nitrile-psilocybin derivative (FIG. 5A), a 4-O-ethyl-5-nitrile-psilocybin derivative (FIG. 5B), O-acylated nitrilated psilocybin derivatives, notably a 4-acetyl-5-nitrile-psilocybin derivative (FIG. 5C), a 4-propanoyl-5-nitrile-psilocybin derivative (FIG. 5D), a 4-hydroxy-5-nitrile-psilocybin derivative (FIG. 5E), and a 4-phospho-5-nitrile-psilocybin derivative (FIG. 5F), a 4-glycosyl-5-nitrile-psilocybin derivative (FIG. 5G), and a 5-nitrile-psilocybin derivative (FIG. 5H).
Figure 5B:
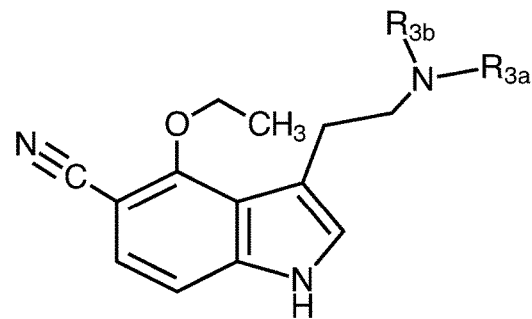
Figure 6A:
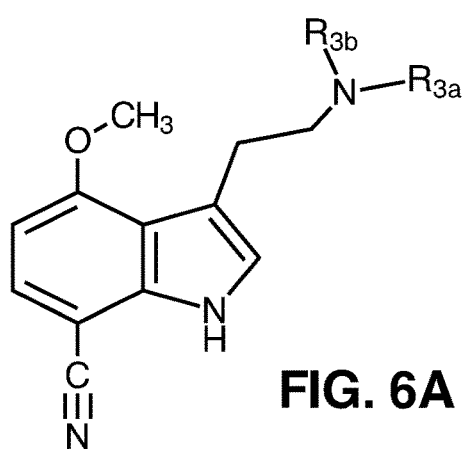
Figure 6B:
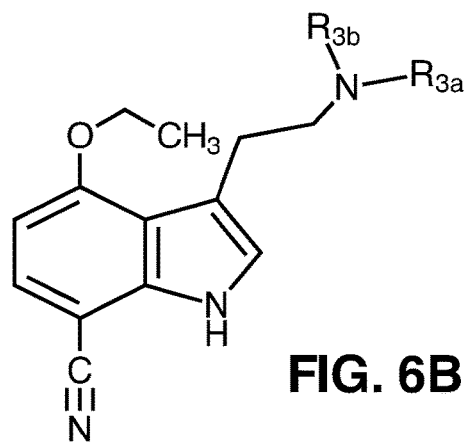
Figure 7A:
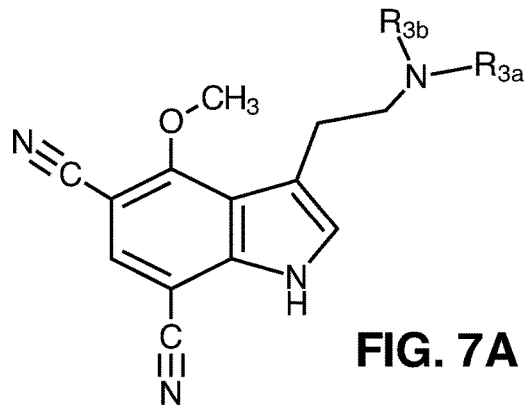
Figure 7B:
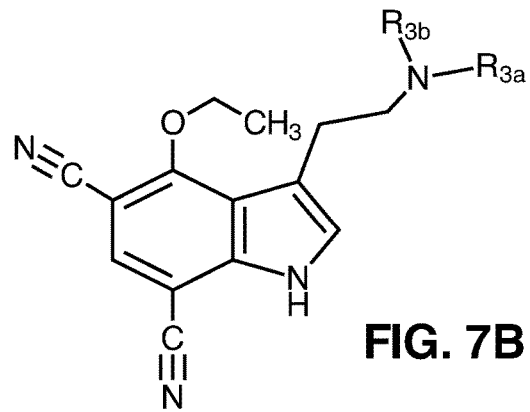

Similarly, the 4-O-ethyl-psilocybin derivative depicted an FIG. 8B may be reacted in similar reaction sequence to form, for example, the 4-O-ethyl-5-nitrile-psilocybin derivative depicted in FIG. 5B, the 4-O-ethyl-7-nitrile-psilocybin derivative depicted in FIG. 6B, or the 4-O-ethyl-5,7-di-nitrile-psilocybin depicted in FIG. 7B.

Figure 5C:
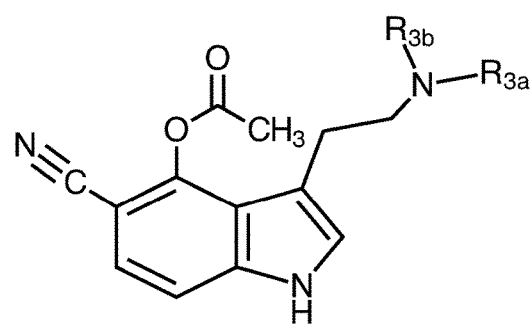
Figure 6C:
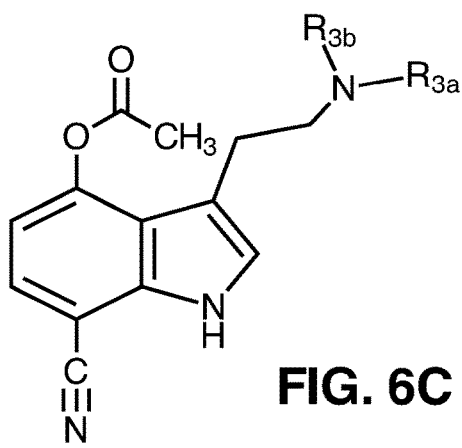
Figure 7C:
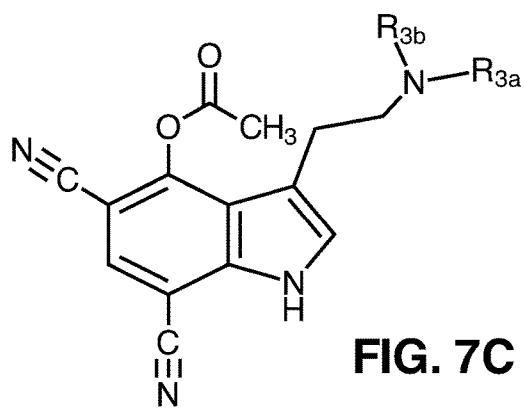

Similarly, the 4-acetyl-psilocybin derivative depicted an FIG. 8C may be reacted in similar reaction sequence to form, for example, the 4-O-acetyl-5-nitrile-psilocybin derivative depicted in FIG. 5C, the 4-O-acetyl-7-nitrile-psilocybin derivative depicted in FIG. 6C, or the 4-O-acetyl-5,7-di-nitrile-psilocybin depicted in FIG. 7C.

Figure 5D:
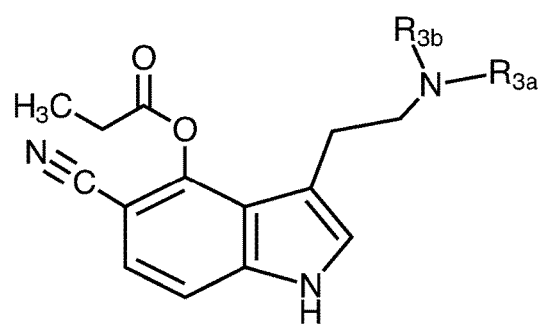
Figure 5G:
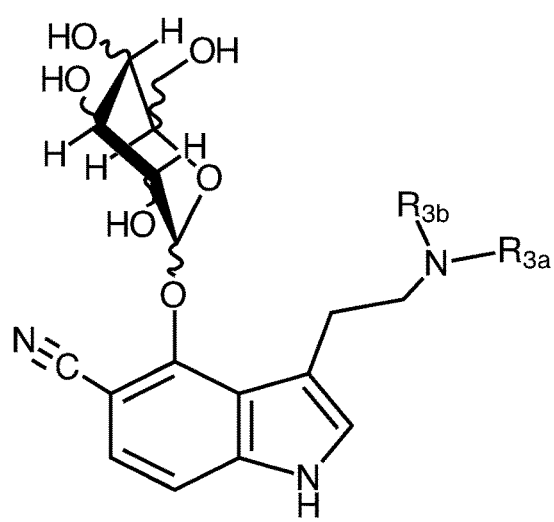
Figure 5H:
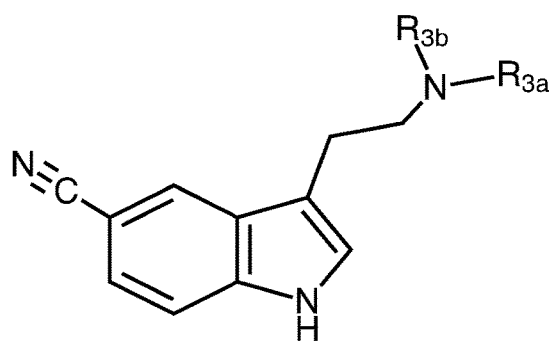
Figure 6D:
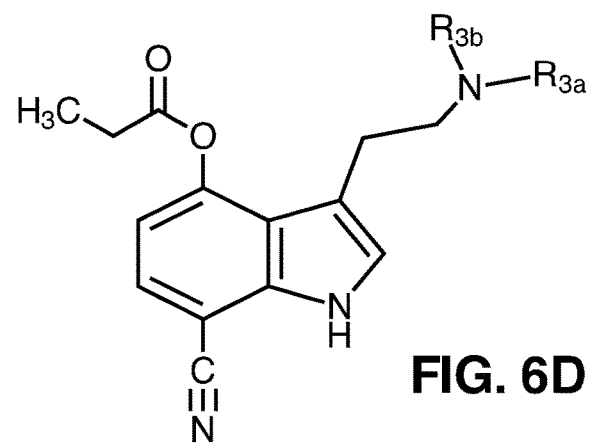
Figure 6E:
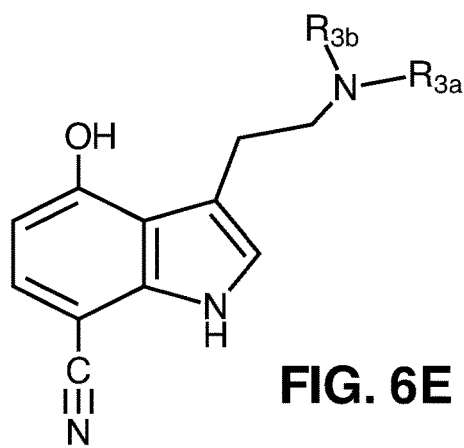
Figure 6F:
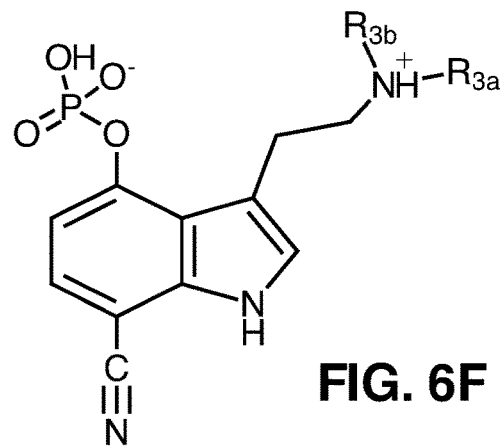
Figure 7D:
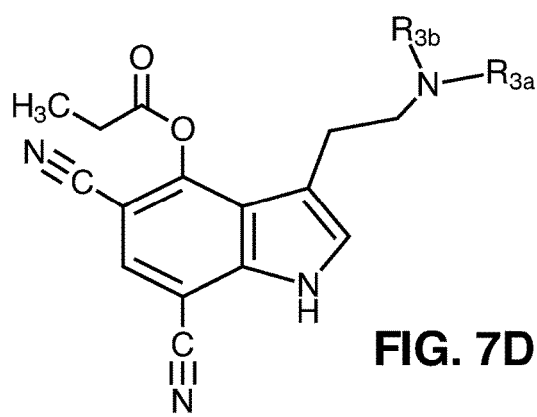
Figure 7E:
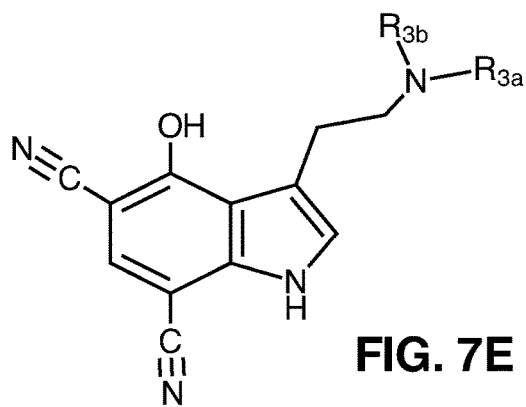
Figure 7F:
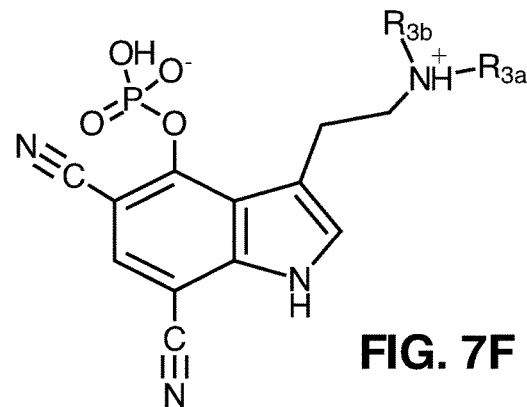

Similarly, the 4-propanoyl-psilocybin derivative depicted an FIG. 8D may be reacted in similar reaction sequence to form, for example, the 4-O-propanoyl-5-nitrile-psilocybin derivative depicted in FIG. 5D, the 4-O-propanoyl-7-nitrile-psilocybin derivative depicted in FIG. 6D, or the 4-O-propanoyl-5,7-di-nitrile-psilocybin depicted in FIG. 7D.

Similarly, the 4-hydroxy-psilocybin derivative depicted an FIG. 8E may be reacted in similar reaction sequence to form, for example, the 4-hydroxy-5-nitrile-psilocybin derivative depicted in FIG. 5E, the 4-hydroxy-7-nitrile-psilocybin derivative depicted in FIG. 6E, or the 4-hydroxy-5,7-di-nitrile-psilocybin depicted in FIG. 7E.

Similarly, the 4-phosphate-psilocybin derivative depicted an FIG. 8F may be reacted in similar reaction sequence to form, for example, the 4-phosphate-5-nitrile-psilocybin derivative depicted in FIG. 5F, the 4-phosphate-7-nitrile-psilocybin derivative depicted in FIG. 6F, or the 4-phosphate-5,7-di-nitrile-psilocybin depicted in FIG. 7F.

Similarly, the 4-O-glycosyl-psilocybin derivative depicted an FIG. 8G may be reacted in similar reaction sequence to form, for example, the 4-O-glycosyl-5-nitrile-psilocybin derivative depicted in FIG. 5G, the 4-O-glycosyl-7-nitrile-psilocybin derivative depicted in FIG. 6G, or the 4-O-glycosyl-5,7-di-nitrile-psilocybin depicted in FIG. 7G.

Similarly, the 4-hydro-psilocybin derivative depicted an FIG. 8H may be reacted to form, for example, the 4-hydro-5-nitrile-psilocybin derivative depicted in FIG. 5H, the 4-hydro-7-nitrile-psilocybin derivative depicted in FIG. 6H, or the 4-hydro-5,7-di-nitrile-psilocybin depicted in FIG. 8H, as well as other analogs.

Furthermore, it is noted that the performance of the reactions, in example different embodiments, may involve nitrilation of different carbon atoms, i.e., the $C_2$, $C_5$, $C_6$ and/or $C_7$ atom. In general, reaction conditions may be selected so that different carbon atoms or combinations thereof are nitrilated. The methods can be used to prepare any other mono-, di- or multi-nitrilated psilocybin derivatives, as hereinbefore noted.

The reactions, such as the example reaction shown in FIGS. 9A, 9B, 9C and 9D, may be conducted in any suitable reaction vessel (e.g., a tube, bottle). Suitable temperatures may range from, for example, e.g., from about 20° C. to about 100° C. Furthermore, reaction times may be varied. As will readily be appreciated by those of skill in the art, the reaction conditions may be optimized depending on the nature of substituents on the starting psilocybin derivative. Further general guidance regarding appropriate reaction conditions for performing nitrilation reactions may be found in: G. Yan; Y. Zhang, J. Wang, Adv. Synth. Catal, 2017, 359, 4068-4105.

In another aspect of the present disclosure, the nitrilated psilocybin compounds may be made biosynthetically. Accordingly, the present disclosure further includes, in one embodiment, a method of making a nitrilated psilocybin derivative the method comprising:

(a) contacting a nitrilated psilocybin precursor compound with a host cell comprising a psilocybin biosynthetic enzyme complement; and (b) growing the host cell to produce a nitrilated psilocybin derivative or salts thereof having the formula (I):

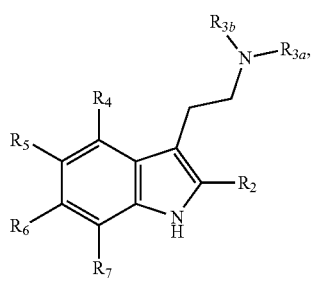

(I)

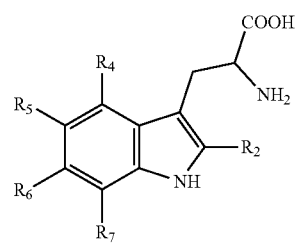

(XIII)

wherein at least one of $R_2$, $R_4$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group.

Implementation of the foregoing example embodiment initially involves providing nitrilated psilocybin precursor compounds and host cells having a psilocybin biosynthetic enzyme complement. Accordingly, next, example nitrilated psilocybin precursor compounds and example host cells that may be selected and used in accordance with the present disclosure will be described. Thereafter, example methodologies and techniques will be described to contact and use the nitrilated psilocybin precursor compounds and cells to produce example nitrilated psilocybin compounds.

A variety of nitrilated psilocybin precursor compounds may be selected, prepared and used. In general, nitrilated psilocybin precursor compounds are nitrilated compounds which biochemically or chemically may be converted into a nitrilated psilocybin derivative having formula (I). In some embodiments, for example, the nitrilated psilocybin precursor compound is a compound comprising a nitrilated indole prototype structure. Examples of such compounds are a nitrilated indole, e.g., 2-nitrile-indole, 4nitrile-indole, 5-nitrile-indole, 6-nitrile-indole, and 7-nitrile-indole; and nitrilated tryptophan derivatives, e.g., 2-nitrile-tryptophan, 4-nitrile-tryptophan, 5-nitrile-tryptophan, 6-nitrile-tryptophan, and 7-nitrile-tryptophan.

Further nitrile psilocybin precursor compounds that may be used include nitrilated indoles, having the formula (XV):

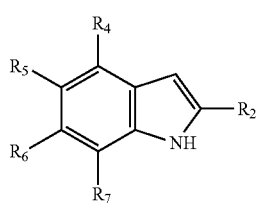

(XV)

wherein at least one of $R_2$, $R_4$, $R_5$, $R_6$ and $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom.

Further nitrilated psilocybin precursor compounds that may be used include compounds having the formula (XIII):

wherein at least one of $R_2$, $R_4$, $R_5$, $R_6$ and $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom.

Turning now to the host cells that can be used in accordance with the present disclosure, it is initially noted that a variety of host cells may be selected in accordance with the present disclosure, including microorganism host cells, plant host cells, and animal host cells.

In accordance herewith the host cell includes a psilocybin biosynthetic enzyme complement. Such cells can be obtained in at least two ways. First, in some embodiments, host cells may be selected in which a psilocybin biosynthetic enzyme complement is naturally present Generally cells naturally producing psilocybin for example, cells of fungal species belonging to the genus *psilocybe*, are suitable in this respect. Second, in some embodiments, a host cell that not naturally produces psilocybin may be modulated to produce a psilocybin biosynthetic enzyme complement. Thus, for example, a nucleic acid sequence encoding a psilocybin biosynthetic enzyme complement may be introduced into a host cell, and upon cell growth the host cells can make the psilocybin biosynthetic enzyme complement.

Typically a nucleic acid sequence encoding one or more enzymes constituting a psilocybin biosynthetic enzyme complement further includes one or more additional nucleic acid sequences, for example, a nucleic acid sequences controlling expression of the one or more enzymes, and these one or more additional nucleic acid sequences together with the nucleic acid sequence encoding the one or more enzymes can be said to form a chimeric nucleic acid sequence.

A host cell which upon cultivation expresses the chimeric nucleic acid can be selected and used in accordance with the present disclosure. Suitable host cells in this respect include, for example, microbial cells, such as bacterial cells, yeast cells, for example, and algal cells or plant cells. A variety of techniques and methodologies to manipulate host cells to introduce nucleic acid sequences in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

In some embodiments, the one or more enzymes constituting a psilocybin enzyme complement can be selected from by a nucleic acid sequence selected from the nucleic acid sequences consisting of:

(a) SEQ.ID NO: 4, SEQ.ID NO: 8, and SEQ.ID NO: 11;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ.ID NO: 5, SEQ.ID NO: 9, and SEQ.ID NO: 12;
(f) a nucleic acid sequence that encodes a functional variant of any one of the amino acid sequences set forth in SEQ.ID NO: 5, SEQ.ID NO: 9, and SEQ.ID NO: 12; and
(g) a nucleic acid sequence that hybridizes under stringent conditions to any one of the nucleic acid sequences set forth in (a), (b), (c), (d), (e) or (f).

Thus, any of the nucleic acid sequence set forth in (a), (b), (c), (d), (e), (f) or (g) may be selected and introduced into a host cell. In particular, however the nucleic acid sequence is selected in conjunction with the selected psilocybin precursor compound, as hereinafter further discussed with reference to FIG. 10.

One example host cell that conveniently may be used is *Escherichia coli*. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Suitable promoter sequences for use in *E. coli* include, for example, the T7 promoter, the T5 promoter, tryptophan (trp) promoter, lactose (lac) promoter, tryptophan/lactose (tac) promoter, lipoprotein (lpp) promoter, and λ phage PL promoter. Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kluyveromyces, Saccharomyces. Schizosaccharomyces, Pichia, Hansenula,* and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example, Yip type vectors, YEp type vectors, YRp type vectors, YCp type vectors, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE and 2 μm plasmids. Such vectors are known to the art and are, for example, described in Cregg et al., Mol Biotechnol. (2000) 16(1): 23-52. Suitable promoter sequences for use in yeast host cells are also known and described, for example, in Mattanovich et al., Methods Mol. Biol., 2012, 824:329-58, and in Romanos et al., 1992, Yeast 8: 423-488. Examples of suitable promoters for use in yeast host cells include promoters of glycolytic enzymes, like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPGI), the 3-phosphoglycerate kinase promoter (PPGK), the glycerol aldehyde phosphate dehydrogenase promoter (PGAP), translation elongation factor promoter (PTEF), *S. cerevisiae* enolase (ENO-1), *S. cerevisiae* galactokinase (GAL1), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL). Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S. Kawai et al., 2010. Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

Thus, to briefly recap, a host cell comprising a chimeric nucleic acid comprising (i) a nucleic acid sequence controlling expression in a host cell and (ii) a nucleic acid sequence encoding a psilocybin biosynthetic enzyme complement, can be prepared in accordance with the present disclosure.

In accordance herewith, host cells are grown to multiply and to express a chimeric nucleic acid. Expression of the chimeric nucleic acid results in the biosynthetic production in the host cell of a psilocybin biosynthetic enzyme complement. Growth media and growth conditions can vary depending on the host cell that is selected, as will be readily appreciated to those of ordinary skill in the art. Growth media typically contain a carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands and inducers. Example carbon sources are e.g., mono- or disaccharides. Example nitrogen sources are e.g., ammonia, urea, amino acids, yeast extract, corn steep liquor and fully or partially hydrolyzed proteins. Example trace metals are e.g., Fe, Zn, Mn, Cu, Mo and $H_3BO_3$. Example water soluble vitamins are e.g., biotin, pantothenate, niacin, thiamine, p-aminobenzoic acid, choline, pyridoxine, folic acid, riboflavin, and ascorbic acid. Further, specific example media include liquid culture media for the growth of yeast cells and bacterial cells including, Luria-Bertani (LB) broth for bacterial cell cultivation, and yeast extract peptone dextrose (YEPD or YPD), for yeast cell cultivation. Further media and growth conditions can be found in Sambrook et al., Molecular Cloning, a Laboratory Manual, Cold Spring Harbor Laboratory Press, 2012, Fourth Ed.

In order for the host cells to produce the nitrilated psilocybin compound, the cells are provided with a precursor compound. Thus, in accordance herewith, host cells may be contacted with a psilocybin precursor compound. In some embodiments, a psilocybin precursor compound can be exogenously supplied, for example, by including a psilocybin precursor compound in the growth medium of the host cells, and growing the host cells in a medium including the psilocybin precursor compound.

Figure 10:
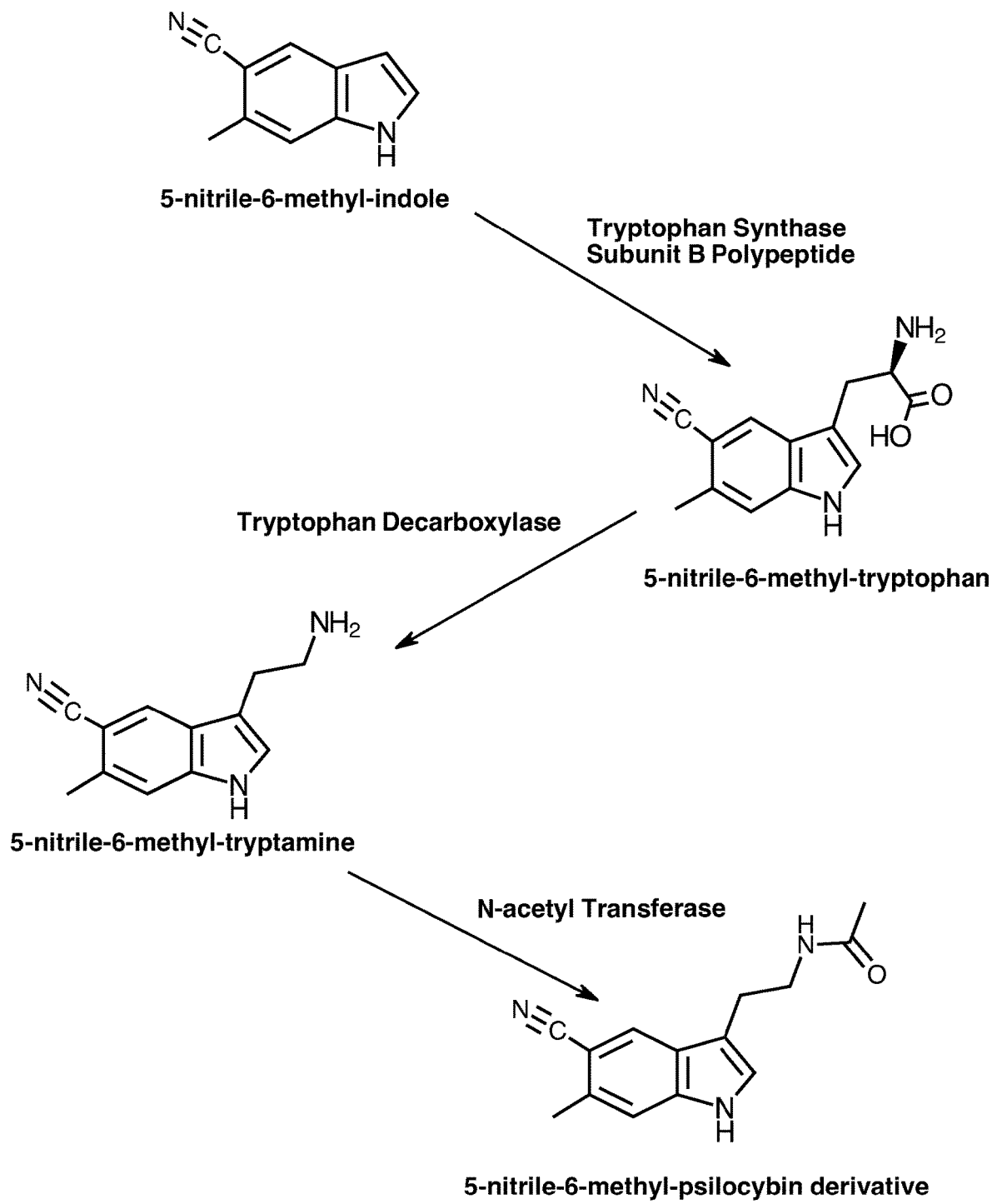
FIG. 10 depicts an example biosynthesis process for the synthesis of a nitrilated psilocybin derivative.

Referring next to FIG. 10, shown therein is an example biosynthetic pathway showing the conversion of example psilocybin precursor compounds to form a nitrilated psilocybin. Thus, as can be appreciated from FIG. 10, various psilocybin precursor compounds may be selected and prepared in nitrilated form, in conjunction with a psilocybin biosynthetic enzyme complement. Thus, by way of example, nitrilated tryptophan (e.g., 2-, 5-, 6-, or 7-nitrilated tryptophan) may be selected and contacted with a host cell comprising a psilocybin biosynthetic enzyme complement comprising tryptophan decarboxylase and optionally N-acetyl transferase, and upon growth of the cells nitrilated psilocybin derivatives can be formed. By way of further example, nitrilated indole (e.g., 2-, 5-, 6-, or 7-nitrilated indole) may be selected and contacted with a host cell comprising a psilocybin biosynthetic enzyme complement comprising tryptophan synthase subunit B polypeptide and tryptophan decarboxylase and optionally N-acetyl transferase, and upon growth of the cells nitrilated psilocybin derivatives can be formed.

In some embodiments, the psilocybin precursor compound can be a nitrilated psilocybin precursor compound which is exogenously supplied to a host cell, for example by inclusion in the host cell's growth medium. Thus, for example, referring to FIG. 10, it will be understood that in accordance herewith, for example, 7-nitrile-indole or 7-nitrile-tryptophan, may be included in the growth medium of a host cell comprising a psilocybin biosynthetic enzyme complement.

Referring to FIG. 10, in a further example embodiment, the nitrilated psilocybin precursor compound can be a nitrilated indole, having the formula (XV):

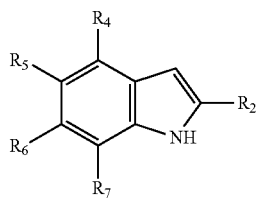

(XV)

wherein at least one of $R_2$, $R_4$, $R_5$, $R_6$ and $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom;

the psilocybin biosynthetic enzyme complement can comprise:
(i) a tryptophan synthase subunit B polypeptide encoded by a nucleic acid selected from:
  (a) SEQ.ID NO: 8;
  (b) a nucleic acid sequence that is substantially identical to the nucleic acid sequence of (a);
  (c) a nucleic acid sequence that is substantially identical to the nucleic acid sequence of (a) but for the degeneration of the genetic code;
  (d) a nucleic acid sequence that is complementary to the nucleic acid sequence of (a);
  (e) a nucleic acid sequence encoding a polypeptide having any one of the amino acid sequences set forth in SEQ.ID NO: 9;
  (f) a nucleic acid sequence that encodes a functional variant of any one of the amino acid sequences set forth in SEQ.ID NO: 9; and
  (g) a nucleic acid sequence that hybridizes under stringent conditions to any one of the nucleic acid sequences set forth in (a), (b), (c), (d), (e) or (f); and
(ii) a tryptophan decarboxylase encoded by a nucleic acid sequence selected from:
  (a) SEQ.ID NO: 11;
  (b) a nucleic acid sequence that is substantially identical to the nucleic acid sequence of (a);
  (c) a nucleic acid sequence that is substantially identical to the nucleic acid sequence of (a) but for the degeneration of the genetic code;
  (d) a nucleic acid sequence that is complementary to the nucleic acid sequence of (a);
  (e) a nucleic acid sequence encoding a polypeptide having any one of the amino acid sequences set forth in SEQ.ID NO: 12;
  (f) a nucleic acid sequence that encodes a functional variant of any one of the amino acid sequences set forth in SEQ.ID NO: 12; and
  (g) a nucleic acid sequence that hybridizes under stringent conditions to any one of the nucleic acid sequences set forth in (a), (b), (c), (d), (e) or (f); and the formed nitrilated psilocybin derivative can be a compound having formula (XIV):

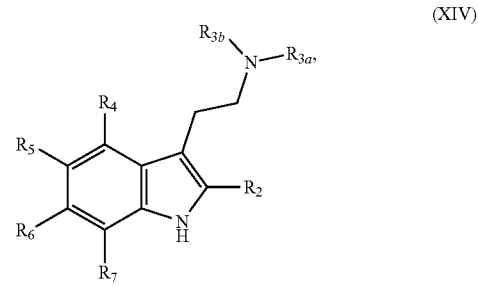

(XIV)

wherein at least one of $R_2$, $R_4$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group.

Referring further to FIG. 10, in another example embodiment, the nitrilated psilocybin precursor compound can be a compound, having the formula (XIII):

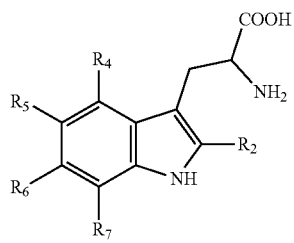

wherein at least one of $R_2$, $R_4$, $R_5$, $R_6$ and $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom;
the psilocybin biosynthetic enzyme complement can comprise:
a tryptophan decarboxylase encoded by a nucleic acid sequence selected from:
(a) SEQ.ID NO: 11;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ.ID NO: 12;
(f) a nucleic acid sequence that encodes a functional variant of any one of the amino acid sequences set forth in SEQ.ID NO: 12; and
(g) a nucleic acid sequence that hybridizes under stringent conditions to any one of the nucleic acid sequences set forth in (a), (b), (c), (d), (e) or (f); and the formed nitrilated psilocybin derivative can be a compound having formula (XIV):

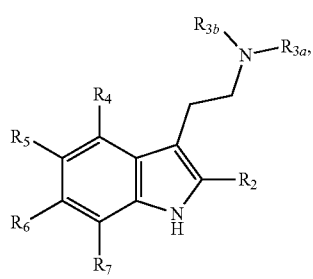

wherein at least one of $R_2$, $R_4$, $R_5$, $R_6$, or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom and wherein $R_{3A}$ and $R_{3B}$ are a hydrogen atom, an alkyl group, acyl group or an aryl group.

In some embodiments, in formula (XIV) $R_{3A}$ and $R_{3B}$ are each a hydrogen atom.

Referring again to FIG. 10, the psilocybin biosynthetic enzyme complement can, in addition to the aforementioned tryptophan decarboxylase and tryptophan synthase subunit B polypeptide, further comprise an N-acetyl transferase.

In at least one embodiment, in an aspect, the N-acetyl transferase can be an enzyme encoded by, a nucleic acid sequence selected from:
(a) SEQ.ID NO: 4;
(b) a nucleic acid sequence that is substantially identical to the nucleic acid sequence of (a);
(c) a nucleic acid sequence that is substantially identical to the nucleic acid sequence of (a) but for the degeneration of the genetic code;
(d) a nucleic acid sequence that is complementary to the nucleic acid sequence of (a);
(e) a nucleic acid sequence encoding a polypeptide having any one of the amino acid sequences set forth in SEQ.ID NO: 5;
(f) a nucleic acid sequence that encodes a functional variant of any one of the amino acid sequences set forth in SEQ.ID NO: 5; and
(g) a nucleic acid sequence that hybridizes under stringent conditions to any one of the nucleic acid sequences set forth in (a), (b), (c), (d), (e) or (f).

In at least one embodiment, in an aspect, the formed nitrilated psilocybin compound can have the formula (XVI):

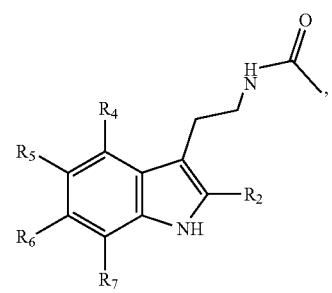

wherein, at least one of $R_2$, $R_4$, $R_5$, $R_6$ or $R_7$ is a nitrile group, and wherein each non-nitrilated $R_2$, $R_5$, $R_6$, or $R_7$ is a hydrogen atom, an alkyl group, or O-alkyl group, wherein $R_4$ is an O-alkyl group, an O-acyl group, a hydroxy group, a phosphate group, a glycosyloxy group, or a hydrogen atom.

It will be clear to those of skill in the art that a significant variety of different nitrilated psilocybin precursor compounds may be selected. FIG. 10 in this respect provides guidance and allows a person of skill in the art to select appropriate psilocybin precursor compounds and a matching a psilocybin biosynthetic enzyme complement.

Upon production by the host cells of the nitrilated psilocybin compounds in accordance with the methods of the present disclosure, the nitrilated psilocybin compounds may be extracted from the host cell suspension, and separated from other constituents within the host cell suspension, such as media constituents and cellular debris. Separation techniques will be known to those of skill in the art and include, for example, solvent extraction (e.g., butane, chloroform, ethanol), column chromatography based techniques, high-performance liquid chromatography (HPLC), for example, and/or countercurrent separation (CCS) based systems. The recovered nitrilated psilocybin compounds may be obtained in a more or less pure form, for example, a preparation of nitrilated psilocybin compounds of at least about 60% (w/w), about 70% (w/w), about 80% (w/w), about 90% (w/w), about 95% (w/w), about 96% (w/w), about 97% (w/w), about 98% (w/w) or about 99% (w/w) purity may be obtained. Thus, in this manner, nitrilated psilocybin derivatives in more or less pure form may be prepared.

Similarly, other methods of making the nitrilated psilocybin compounds that may be used in accordance herewith may yield preparations of nitrilated compounds of at least about 60% (w/w), about 70% (w/w), about 80% (w/w), about 90% (w/w), about 95% (w/w), about 96% (w/w), about 97% (w/w), about 98% (w/w), or about 99% (w/w) purity.

It will now be clear from the foregoing that novel nitrilated psilocybin derivatives are disclosed herein, as well as methods of making nitrilated psilocybin derivatives. The nitrilated psilocybin compounds may be formulated for use as a pharmaceutical drug or recreational drug.

SUMMARY OF SEQUENCES

SEQ.ID NO: 1 sets forth a nucleic acid sequence of pCDM4 vector

SEQ.ID NO: 2 sets forth a nucleic acid sequence encoding a synthetic FLAG epitope tag polypeptide SEQ.ID NO: 3 sets forth deduced amino acid sequence of a synthetic FLAG epitope tag polypeptide SEQ.ID NO: 4 sets forth a nucleic acid sequence encoding a *Streptomyces griseofuscus* PsmF N-acetyltransferase polypeptide.

SEQ.ID NO: 5 sets forth a deduced amino acid sequence of a *Streptomyces griseofuscus* PsmF N-acetyltransferase polypeptide.

SEQ.ID NO: 6 sets forth a nucleic acid sequence encoding a synthetic V5 epitope tag polypeptide SEQ.ID NO: 7 sets forth deduced amino acid sequence of a synthetic V5 epitope tag polypeptide SEQ.ID NO: 8 sets forth a nucleic acid sequence encoding a mutated *Thermotoga maritima* TmTrpB-2F3 tryptophan synthase subunit B polypeptide.

SEQ.ID NO: 9 sets forth a deduced amino acid sequence of a mutated *Thermotoga maritima* TmTrpB-2F3 tryptophan synthase subunit B polypeptide.

SEQ.ID NO: 10 sets forth a nucleic acid sequence of pETM6-H10 vector

SEQ.ID NO: 11 sets forth a nucleic acid sequence encoding a *Bacillus atrophaeus* BaTDC tryptophan decarboxylase polypeptide.

SEQ.ID NO: 12 sets forth a deduced amino acid sequence of a *Bacillus atrophaeus* BaTDC tryptophan decarboxylase polypeptide.

SEQUENCES

SEQ. ID NO: 1

```
GCTAACAGCGCGATTTGCTGGTGACCCAATGCGACCAGATGCTCCACGCCCAGTCGCGT
ACCGTCTTCATGGGAGAAAATAATACTGTTGATGGGTGTCTGGTCAGAGACATCAAGAA
ATAACGCCGGAACATTAGTGCAGGCAGCTTCCACAGCAATGGCATCCTGGTCATCCAGC
GGATAGTTAATGATCAGCCCACTGACGCGTTGCGCGAGAAGATTGTGCACCGCCGCTTT
ACAGGCTTCGACGCCGCTTCGTTCTACCATCGACACCACCACGCTGGCACCCAGTTGAT
CGGCGCGAGATTTAATCGCCGCGACAATTTGCGACGGCGCGTGCAGGGCCAGACTGGAG
GTGGCAACGCCAATCAGCAACGACTGTTTGCCCGCCAGTTGTTGTGCCACGCGGTTGGG
AATGTAATTCAGCTCCGCCATCGCCGCTTCCACTTTTTCCCGCGTTTTCGCAGAAACGT
GGCTGGCCTGGTTCACCACGCGGGAAACGGTCTGATAAGAGACACCGGCATACTCTGCG
ACATCGTATAACGTTACTGGTTTCACATTCACCACCCTGAATTGACTCTCTTCCGGGCG
CTATCATGCCATACCGCGAAAGGTTTTGCGCCATTCGATGGTGTCCGGGATCTCGACGC
TCTCCCTTATGCGACTCCTGCATTAGGAAGCAGCCCAGTAGTAGGTTGAGGCCGTTGAG
CACCGCCGCCGCAAGGAATGGTGCATGCAAGGAGATGGCGCCCAACAGTCCCCCGGCCA
CGGGGCCTGCCACCATACCCACGCCGAAACAAGCGCTCATGAGCCCGAAGTGGCGAGCC
CGATCTTCCCCATCGGTGATGTCGGCGATATAGGCGCCAGCAACCGCACCTGTGGCGCC
GGTGATGCCGGCCACGATGCGTCCGGCGTAGCCTAGGATCGAGATCGATCTCGATCCCG
CGAAATTAATACGACTCACTATAGGGAATTGTGAGCGGATAACAATTCCCCTCTAGAA
ATAATTTTGTTTAACTTTAAGAAGGAGATATACATATGGCAGATCTCAATTGGATATCG
GCCGGCCACGCGATCGCTGACGTCGGTACCCTCGAGTCTGGTAAAGAAACCGCTGCTGC
GAAATTTGAACGCCAGCACATGGACTCGTCTACTAGTCGCAGCTTAATTAACCTAAACT
GCTGCCACCGCTGAGCAATAACTAGCATAACCCCTTGGGGCCTCTAAACGGGTCTTGAG
GGGTTTTTTGCTAGCGAAAGGAGGAGTCGACACTGCTTCCGGTAGTCAATAAACCGGTA
AACCAGCAATAGACATAAGCGGCTATTTAACGACCCTGCCCTGAACCGACGACCGGGTC
```

-continued

```
ATCGTGGCCGGATCTTGCGGCCCCTCGGCTTGAACGAATTGTTAGACATTATTTGCCGA
CTACCTTGGTGATCTCGCCTTTCACGTAGTGGACAAATTCTTCCAACTGATCTGCGCGC
GAGGCCAAGCGATCTTCTTCTTGTCCAAGATAAGCCTGTCTAGCTTCAAGTATGACGGG
CTGATACTGGGCCGGCAGGCGCTCCATTGCCCAGTCGGCAGCGACATCCTTCGGCGCGA
TTTTGCCGGTTACTGCGCTGTACCAAATGCGGGACAACGTAAGCACTACATTTCGCTCA
TCGCCAGCCCAGTCGGGCGGCGAGTTCCATAGCGTTAAGGTTTCATTTAGCGCCTCAAA
TAGATCCTGTTCAGGAACCGGATCAAAGAGTTCCTCCGCCGCTGGACCTACCAAGGCAA
CGCTATGTTCTCTTGCTTTTGTCAGCAAGATAGCCAGATCAATGTCGATCGTGGCTGGC
TCGAAGATACCTGCAAGAATGTCATTGCGCTGCCATTCTCCAAATTGCAGTTCGCGCTT
AGCTGGATAACGCCACGGAATGATGTCGTCGTGCACAACAATGGTGACTTCTACAGCGC
GGAGAATCTCGCTCTCTCCAGGGGAAGCCGAAGTTTCCAAAAGGTCGTTGATCAAAGCT
CGCCGCGTTGTTTCATCAAGCCTTACGGTCACCGTAACCAGCAAATCAATATCACTGTG
TGGCTTCAGGCCGCCATCCACTGCGGAGCCGTACAAATGTACGGCCAGCAACGTCGGTT
CGAGATGGCGCTCGATGACGCCAACTACCTCTGATAGTTGAGTCGATACTTCGGCGATC
ACCGCTTCCCTCATACTCTTCCTTTTTCAATATTATTGAAGCATTTATCAGGGTTATTG
TCTCATGAGCGGATACATATTTGAATGTATTTAGAAAAATAAACAAATAGCCAGCTCAC
TCGGTCGCTACGCTCCGGGCGTGAGACTGCGGCGGGCGCTGCGGACACATACAAAGTTA
CCCACAGATTCCGTGGATAAGCAGGGGACTAACATGTGAGGCAAAACAGCAGGGCCGCG
CCGGTGGCGTTTTTCCATAGGCTCCGCCCTCCTGCCAGAGTTCACATAAACAGACGCTT
TTCCGGTGCATCTGTGGGAGCCGTGAGGCTCAACCATGAATCTGACAGTACGGGCGAAA
CCCGACAGGACTTAAAGATCCCCACCGTTTCCGGCGGGTCGCTCCCTCTTGCGCTCTCC
TGTTCCGACCCTGCCGTTTACCGGATACCTGTTCCGCCTTTCTCCCTTACGGGAAGTGT
GGCGCTTTCTCATAGCTCACACACTGGTATCTCGGCTCGGTGTAGGTCGTTCGCTCCAA
GCTGGGCTGTAAGCAAGAACTCCCCGTTCAGCCCGACTGCTGCGCCTTATCCGGTAACT
GTTCACTTGAGTCCAACCCGGAAAAGCACGGTAAAACGCCACTGGCAGCAGCCATTGGT
AACTGGGAGTTCGCAGAGGATTTGTTTAGCTAAACACGCGGTTGCTCTTGAAGTGTGCG
CCAAAGTCCGGCTACACTGGAAGGACAGATTTGGTTGCTGTGCTCTGCGAAAGCCAGTT
ACCACGGTTAAGCAGTTCCCCAACTGACTTAACCTTCGATCAAACCACCTCCCCAGGTG
GTTTTTTCGTTTACAGGGCAAAAGATTACGCGCAGAAAAAAAGGATCTCAAGAAGATCC
TTTGATCTTTTCTACTGAACCGCTCTAGATTTCAGTGCAATTTATCTCTTCAAATGTAG
CACCTGAAGTCAGCCCCATACGATATAAGTTGTAATTCTCATGTTAGTCATGCCCCGCG
CCCACCGGAAGGAGCTGACTGGGTTGAAGGCTCTCAAGGGCATCGGTCGAGATCCCGGT
GCCTAATGAGTGAGCTAACTTACATTAATTGCGTTGCGCTCACTGCCCGCTTTCCAGTC
GGGAAACCTGTCGTGCCAGCTGCATTAATGAATCGGCCAACGCGCGGGGAGAGGCGGTT
TGCGTATTGGGCGCCAGGGTGGTTTTTCTTTTCACCAGTGAGACGGGCAACAGCTGATT
GCCCTTCACCGCCTGGCCCTGAGAGAGTTGCAGCAAGCGGTCCACGCTGGTTTGCCCCA
GCAGGCGAAAATCCTGTTTGATGGTGGTTAACGGCGGGATATAACATGAGCTGTCTTCG
GTATCGTCGTATCCCACTACCGAGATGTCCGCACCAACGCGCAGCCCGGACTCGGTAAT
GGCGCGCATTGCGCCCAGCGCCATCTGATCGTTGGCAACCAGCATCGCAGTGGGAACGA
TGCCCTCATTCAGCATTTGCATGGTTTGTTGAAAACCGGACATGGCACTCCAGTCGCCT
```

-continued
TCCCGTTCCGCTATCGGCTGAATTTGATTGCGAGTGAGATATTTATGCCAGCCAGCCAG

ACGCAGACGCGCCGAGACAGAACTTAATGGGCCC

SEQ. ID NO: 2
GACTACAAGGATGACGATGACAAA

SEQ. ID NO: 3
DYKDDDDK

SEQ. ID NO: 4
ATGAACACCTTCAGAACAGCCACTGCCAGAGACATACCTGATGTAGCAGCAACTCTTAC

GGAAGCCTTCGCAACTGATCCACCCACGCAGTGGGTGTTCCCCGACGGTACTGCCGCCG

TCAGCAGGTTCTTTACACATGTTGCAGATAGGGTTCACACGGCCGGTGGTATTGTTGAG

CTACTACCAGACAGAGCCGCCATGATTGCATTGCCACCACACGTGAGGCTGCCAGGAGA

AGCTGCCGACGGAAGGCAGGCGGAAATTCAGAGAAGGCTGGCAGACAGGCACCCGCTGA

CACCTCACTACTACCTGCTGTTTTACGGAGTTAGAACGGCACACCAGGGTTCGGGATTG

GGCGGAAGAATGCTGGCCAGATTAACTAGCAGAGCTGATAGGGACAGGGTGGGTACATA

TACTGAGGCATCCACCTGGCGTGGCGCTAGACTGATGCTGAGACATGGATTCCATGCTA

CAAGGCCACTAAGATTGCCAGATGGACCCAGCATGTTTCCACTTTGGAGAGATCCAATC

CATGATCATTCTGATTAG

SEQ. ID NO: 5
MNTFRTATARDIPDVAATLTEAFATDPPTQWVFPDGTAAVSRFFTHVADRVHTAGGIVE

LLPDRAAMIALPPHVRLPGEAADGRQAEIQRRLADRHPLTPHYYLLFYGVRTAHQGSGL

GGRMLARLTSRADRDRVGTYTEASTWRGARLMLRHGFHATRPLRLPDGPSMFPLWRDPI

HDHSD

SEQ. ID NO: 6
GGTAAGCCAATTCCAAATCCTTTGTTGGGTTTGGACTCCACC

SEQ. ID NO: 7
GKPIPNPLLGLDST

SEQ. ID NO: 8
ATGAAAGGATATTTCGGACCATACGGTGGCCAGTACGTACCAGAAATATTAATGGGTGC

CTTAGAGGAGTTAGAGGCAGCATACGAGGAGATTATGAAGGATGAGAGCTTCTGGAAGG

AGTTCAACGATCTACTGAGGGATTACGCAGGCAGACCAACGCCATTGTACTTTGCCAGG

AGATTGTCTGAGAAGTACGGCGCCCGTGTTTACTTGAAGCGTGAGGATCTGCTGCACAC

TGGAGCACACAAGATAAATAACGCTATCGGACAGGTTTTATTGGCCAAATTAATGGGGA

AGACACGTATCATAGCCGAGACGGGAGCTGGGCAGCATGGAGTCGCTACTGCTACCGCT

GCTGCCCTGTTCGGAATGGAATGTGTGATCTACATGGGTGAAGAGGACACAATCAGACA

GAAGTTGAACGTGGAGCGTATGAAATTATTAGGGGCTAAAGTTGTCCCTGTTAAGTCTG

GCAGTAGGACCTTGAAGGATGCGATAGACGAGGCTTTGAGAGACTGGATTACTAATTTA

CAGACAACATATTATGTTATCGGATCTGTTGTTGGTCCCCACCCTTACCCAATTATCGT

AAGGAATTTCCAGAAGGTTATCGGTGAGGAGACCAAGAAGCAAATACCAGAAAAGGAAG

GTCGTTTGCCAGACTATATAGTTGCCTGCGTAGGCGGCGGTAGCAATGCCGCAGGTATA

TTTTACCCATTCATAGACTCTGGAGTAAAGCTGATAGGTGTTGAGGCAGGTGGCGAGGG

ATTGGAGACAGGTAAACACGCAGCCTCGTTATTAAAGGGTAAAATTGGCTATTTACATG

GATCGAAGACCTTTGTTCTACAAGATGACTGGGGTCAAGTCCAAGTGAGCCATTCGGTG

TCAGCTGGTCTTGACTATTCAGGAGTAGGACCTGAGCATGCTTATTGGAGAGAGACAGG

GAAGGTTCTGTACGACGCAGTGACTGACGAAGAGGCTTTGGACGCATTTATAGAGTTAT

-continued
CAAGACTAGAGGGCATTATACCCGCTTTAGAGTCATCGCATGCTCTAGCATATTTGAAG

AAGATAAATATAAAAGGTAAGGTTGTGGTGGTCAACCTATCAGGGAGAGGGGATAAAGA

CCTGGAGTCAGTCTTAAACCATCCATACGTGAGAGAAAGAATTAGATGA

SEQ. ID NO: 9
MKGYFGPYGGQYVPEILMGALEELEAAYEEIMKDESFWKEFNDLLRDYAGRPTPLYFAR

RLSEKYGARVYLKREDLLHTGAHKINNAIGQVLLAKLMGKTRIIAETGAGQHGVATATA

AALFGMECVIYMGEEDTIRQKLNVERMKLLGAKVVPVKSGSRTLKDAIDEALRDWITNL

QTTYYVIGSVVGPHPYPIIVRNFQKVIGEETKKQIPEKEGRLPDYIVACVGGGSNAAGI

FYPFIDSGVKLIGVEAGGEGLETGKHAASLLKGKIGYLHGSKTFVLQDDWGQVQVSHSV

SAGLDYSGVGPEHAYWRETGKVLYDAVTDEEALDAFIELSRLEGIIPALESSHALAYLK

KINIKGKVVVVNLSGRGDKDLESVLNHPYVRERIR

SEQ. ID NO: 10
GAAGAATTGTGAGCGGATAACAATTCCCCTCTAGAAATAATTTTGTTTAACTTTAAGAA

GGAGATATACATATGGCAGATCTCAATTGGATATCGGCCGGCCACGCGATCGCTGACGT

CGGTACCCTCGAGTCTGGTAAAGAAACCGCTGCTGCGAAATTTGAACGCCAGCACATGG

ACTCGTCTACTAGTCGCAGCTTAATTAACCTAAACTGCTGCCACCGCTGAGCAATAACT

AGCATAACCCCTTGGGGCCTCTAAACGGGTCTTGAGGGGTTTTTTGCTAGCGAAAGGAG

GAGTCGACTATATCCGGATTGGCGAATGGGACGCGCCCTGTAGCGGCGCATTAAGCGCG

GCGGGTGTGGTGGTTACGCGCAGCGTGACCGCTACACTTGCCAGCGCCCTAGCGCCCGC

TCCTTTCGCTTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTCGACCCCAAA

AAACTTGATTAGGGTGATGGTTCACGTAGTGGGCCATCGCCCTGATAGACGGTTTTTCG

CCCTTTGACGTTGGAGTCCACGTTCTTTAATAGTGGACTCTTGTTCCAAACTGGAACAA

CACTCAACCCTATCTCGGTCTATTCTTTTGATTTATAAGGGATTTTGCCGATTTCGGCC

TATTGGTTAAAAAATGAGCTGATTTAACAAAAATTTAACGCGAATTTTAACAAAATATT

AACGTTTACAATTTCTGGCGGCACGATGGCATGAGATTATCAAAAAGGATCTTCACCTA

GATCCTTTTAAATTAAAAATGAAGTTTTAAATCAATCTAAAGTATATATGAGTAAACTT

GGTCTGACAGTTACCAATGCTTAATCAGTGAGGCACCTATCTCAGCGATCTGTCTATTT

CGTTCATCCATAGTTGCCTGACTCCCCGTCGTGTAGATAACTACGATACGGGAGGGCTT

ACCATCTGGCCCCAGTGCTGCAATGATACCGCGAGACCCACGCTCACCGGCTCCAGATT

TATCAGCAATAAACCAGCCAGCCGGAAGGGCCGAGCGCAGAAGTGGTCCTGCAACTTTA

TCCGCCTCCATCCAGTCTATTAATTGTTGCCGGGAAGCTAGAGTAAGTAGTTCGCCAGT

TAATAGTTTGCGCAACGTTGTTGCCATTGCTACAGGCATCGTGGTGTCACGCTCGTCGT

TTGGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAGTT

GGCCGCAGTGTTATCACTCATGGTTATGGCAGCACTGCATAATTCTCTTACTGTCATGC

CATCCGTAAGATGCTTTTCTGTGACTGGTGAGTACTCAACCAAGTCATTCTGAGAATAG

TGTATGCGGCGACCGAGTTGCTCTTGCCCGGCGTCAATACGGGATAATACCGCGCCACA

TAGCAGAACTTTAAAAGTGCTCATCATTGGAAAACGTTCTTCGGGGCGAAAACTCTCAA

GGATCTTACCGCTGTTGAGATCCAGTTCGATGTAACCCACTCGTGCACCCAACTGATCT

TCAGCATCTTTTACTTTCACCAGCGTTTCTGGGTGAGCAAAAACAGGAAGGCAAAATGC

CGCAAAAAAGGGAATAAGGGCGACACGGAAATGTTGAATACTCATACTCTTCCTTTTTC

-continued

AATCATGATTGAAGCATTTATCAGGGTTATTGTCTCATGAGCGGATACATATTTGAATG
TATTTAGAAAAATAAACAAATAGGTCATGACCAAAATCCCTTAACGTGAGTTTTCGTTC
CACTGAGCGTCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGGTTTGTTTGC
CGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGC
ACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGGCCT
TTTTACGGTTCCTGGCCTTTTGCTGGCCTTTTGCTCACATGTTCTTTCCTGCGTTATCC
CCTGATTCTGTGGATAACCGTATTACCGCCTTTGAGTGAGCTGATACCGCTCGCCGCAG
CCGAACGACCGAGCGCAGCGAGTCAGTGAGCGAGGAAGCGGAAGAGCGCCTGATGCGGT
ATTTTCTCCTTACGCATCTGTGCGGTATTTCACACCGCATATATGGTGCACTCTCAGTA
CAATCTGCTCTGATGCCGCATAGTTAAGCCAGTATACACTCCGCTATCGCTACGTGACT
GGGTCATGGCTGCGCCCCGACACCCGCCAACACCCGCTGACGCGCCCTGACGGGCTTGT
CTGCTCCCGGCATCCGCTTACAGACAAGCTGTGACCGTCTCCGGGAGCTGCATGTGTCA
GAGGTTTTCACCGTCATCACCGAAACGCGCGAGGCAGCTGCGGTAAAGCTCATCAGCGT
GGTCGTGAAGCGATTCACAGATGTCTGCCTGTTCATCCGCGTCCAGCTCGTTGAGTTTC
TCCAGAAGCGTTAATGTCTGGCTTCTGATAAAGCGGGCCATGTTAAGGGCGGTTTTTTC
CTGTTTGGTCACTGATGCCTCCGTGTAAGGGGGATTTCTGTTCATGGGGGTAATGATAC
CGATGAAACGAGAGAGGATGCTCACGATACGGGTTACTGATGATGAACATGCCCGGTTA
CTGGAACGTTGTGAGGGTAAACAACTGGCGGTATGGATGCGGCGGGACCAGAGAAAAAT
CACTCAGGGTCAATGCCAGCGCTTCGTTAATACAGATGTAGGTGTTCCACAGGGTAGCC
AGCAGCATCCTGCGATGCAGATCCGGAACATAATGGTGCAGGGCGCTGACTTCCGCGTT
TCCAGACTTTACGAAACACGGAAACCGAAGACCATTCATGTTGTTGCTCAGGTCGCAGA
CGTTTTGCAGCAGCAGTCGCTTCACGTTCGCTCGCGTATCGGTGATTCATTCTGCTAAC
CAGTAAGGCAACCCCGCCAGCCTAGCCGGGTCCTCAACGACAGGAGCACGATCATGCTA
GTCATGCCCCGCGCCCACCGGAAGGAGCTGACTGGGTTGAAGGCTCTCAAGGGCATCGG
TCGAGATCCCGGTGCCTAATGAGTGAGCTAACTTACATTAATTGCGTTGCGCTCACTGC
CCGCTTTCCAGTCGGGAAACCTGTCGTGCCAGCTGCATTAATGAATCGGCCAACGCGCG
GGGAGAGGCGGTTTGCGTATTGGGCGCCAGGGTGGTTTTTCTTTTCACCAGTGAGACGG
GCAACAGCTGATTGCCCTTCACCGCCTGGCCCTGAGAGAGTTGCAGCAAGCGGTCCACG
CTGGTTTGCCCCAGCAGGCGAAAATCCTGTTTGATGGTGGTTAACGGCGGGATATAACA
TGAGCTGTCTTCGGTATCGTCGTATCCCACTACCGAGATGTCCGCACCAACGCGCAGCC
CGGACTCGGTAATGGCGCGCATTGCGCCCAGCGCCATCTGATCGTTGGCAACCAGCATC
GCAGTGGGAACGATGCCCTCATTCAGCATTTGCATGGTTTGTTGAAAACCGGACATGGC

-continued
ACTCCAGTCGCCTTCCCGTTCCGCTATCGGCTGAATTTGATTGCGAGTGAGATATTTAT

GCCAGCCAGCCAGACGCAGACGCGCCGAGACAGAACTTAATGGGCCCGCTAACAGCGCG

ATTTGCTGGTGACCCAATGCGACCAGATGCTCCACGCCCAGTCGCGTACCGTCTTCATG

GGAGAAAATAATACTGTTGATGGGTGTCTGGTCAGAGACATCAAGAAATAACGCCGGAA

CATTAGTGCAGGCAGCTTCCACAGCAATGGCATCCTGGTCATCCAGCGGATAGTTAATG

ATCAGCCCACTGACGCGTTGCGCGAGAAGATTGTGCACCGCCGCTTTACAGGCTTCGAC

GCCGCTTCGTTCTACCATCGACACCACCACGCTGGCACCCAGTTGATCGGCGCGAGATT

TAATCGCCGCGACAATTTGCGACGGCGCGTGCAGGGCCAGACTGGAGGTGGCAACGCCA

ATCAGCAACGACTGTTTGCCCGCCAGTTGTTGTGCCACGCGGTTGGGAATGTAATTCAG

CTCCGCCATCGCCGCTTCCACTTTTTCCCGCGTTTTCGCAGAAACGTGGCTGGCCTGGT

TCACCACGCGGGAAACGGTCTGATAAGAGACACCGGCATACTCTGCGACATCGTATAAC

GTTACTGGTTTCACATTCACCACCCTGAATTGACTCTCTTCCGGGCGCTATCATGCCAT

ACCGCGAAAGGTTTTGCGCCATTCGATGGTGTCCGGGATCTCGACGCTCTCCCTTATGC

GACTCCTGCATTAGGAAGCAGCCCAGTAGTAGGTTGAGGCCGTTGAGCACCGCCGCCGC

AAGGAATGGTGCATGCAAGGAGATGGCGCCCAACAGTCCCCCGGCCACGGGGCCTGCCA

CCATACCCACGCCGAAACAAGCGCTCATGAGCCCGAAGTGGCGAGCCCGATCTTCCCCA

TCGGTGATGTCGGCGATATAGGCGCCAGCAACCGCACCTGTGGCGCCGGTGATGCCGGC

CACGATGCGTCCGGCGTAGCCTAGGATCGAGATCGATCTCGATCCCGCGAAATTAATAC

GACTCACTACG

SEQ. ID NO: 11
ATGATGTCTGAAAATTTGCAATTGTCAGCTGAAGAAATGAGACAATTGGGTTACCAAGC

AGTTGATTTGATCATCGATCACATGAACCATTTGAAGTCTAAGCCAGTTTCAGAAACAA

TCGATTCTGATATCTTGAGAAATAAGTTGACTGAATCTATCCCAGAAATGGTTCAGAT

CCAAAGGAATTGTTGCATTTCTTGAACAGAAACGTTTTTAATCAAATTACACATGTTGA

TCATCCACATTTCTTGGCTTTTGTTCCAGGTCCAAATAATTACGTTGGTGTTGTTGCAG

ATTTCTTGGCTTCTGGTTTTAATGTTTTTCCAACTGCATGGATTGCTGGTGCAGGTGCT

GAACAAATCGAATTGACTACAATTAATTGGTTGAAATCTATGTTGGGTTTTCCAGATTC

AGCTGAAGGTTTATTTGTTTCTGGTGGTTCAATGGCAAATTTGACAGCTTTGACTGTTG

CAAGACAGGCTAAGTTGAACAACGATATCGAAAATGCTGTTGTTTACTTCTCTGATCAA

ACACATTTCTCAGTTGATAGAGCATTGAAGGTTTTAGGTTTTAAACATCATCAAATCTG

TAGAATCGAAACAGATGAACATTTGAGAATCTCTGTTTCAGCTTTGAAGAAACAAATTA

AAGAAGATAGAACTAAGGGTAAAAAGCCATTCTGTGTTATTGCAAATGCTGGTACTACA

AATTGTGGTGCTGTTGATTCTTTGAACGAATTAGCAGATTTGTGTAACGATGAAGATGT

TTGGTTGCATGCTGATGGTTCTTATGGTGCTCCAGCTATCTTGTCTGAAAAGGGTTCAG

CTATGTTGCAAGGTATTCATAGAGCAGATTCTTTGACTTTAGATCCACATAAGTGGTTG

TTCCAACCATACGATGTTGGTTGTGTTTTGATCAGAAACTCTCAATATTTGTCAAAGAC

TTTTAGAATGATGCCAGAATACATCAAGGATTCAGAAACTAACGTTGAAGGTGAAATTA

ATTTCGGTGAATGTGGTATCGAATTGTCAAGAAGATTCAGAGCTTTGAAGGTTTGGTTG

TCTTTTAAAGTTTTCGGTGTTGCTGCTTTTAGACAAGCAATCGATCATGGTATCATGTT

AGCAGAACAAGTTGAAGCATTTTTGGGTAAAGCAAAAGATTGGGAAGTTGTTACACCAG

CTCAATTGGGTATCGTTACTTTTAGATACATTCCATCTGAATTGGCATCAACAGATACT

```
                               -continued
ATTAATGAAATTAATAAGAAATTGGTTAAGGAAATCACACATAGAGGTTTCGCTATGTT

ATCTACTACAGAATTGAAGGAAAAGGTTGTTATTAGATTGTGTTCAATTAATCCAAGAA

CTACAACTGAAGAAATGTTGCAAATCATGATGAAGATTAAAGCATTGGCTGAAGAAGTT

TCTATTTCATACCCATGTGTTGCTGAATAA
                                                        SEQ. ID NO: 12
MMSENLQLSAEEMRQLGYQAVDLIIDHMNHLKSKPVSETIDSDILRNKLTESIPENGSD

PKELLHFLNRNVFNQITHVDHPHFLAFVPGPNNYVGVVADFLASGFNVFPTAWIAGAGA

EQIELTTINWLKSMLGFPDSAEGLFVSGGSMANLTALTVARQAKLNNDIENAVVYFSDQ

THFSVDRALKVLGFKHHQICRIETDEHLRISVSALKKQIKEDRTKGKKPFCVIANAGTT

NCGAVDSLNELADLCNDEDVWLHADGSYGAPAILSEKGSAMLQGIHRADSLTLDPHKWL

FQPYDVGCVLIRNSQYLSKTFRMMPEYIKDSETNVEGEINFGECGIELSRRFRALKVWL

SFKVFGVAAFRQAIDHGIMLAEQVEAFLGKAKDWEVVTPAQLGIVTFRYIPSELASTDT

INEINKKLVKEITHRGFAMLSTTELKEKVVIRLCSINPRTTTEEMLQIMMKIKALAEEV

SISYPCVAE
```

EXAMPLES

Example 1—Synthesis of a First Nitrilated Psilocybin Compound

E. coli strain Ec-1 was constructed as follows. For plasmid cloning, Top10 or XL1-blue strains were used depending on antibiotic markers. Standard LB media was used for culturing. For gene expression and feeding experiments, the parent host strain employed was BL21 (DE3). From plasmid pCDM4 (SEQ.ID NO: 1), the plasmid pCDM4-PsmF-FLAG was created by inserting an in-frame, C-terminally FLAG-tagged (SEQ.ID NO: 2, SEQ.ID NO: 3) PsmF gene (SEQ.ID NO: 4, SEQ.ID NO: 5) into the NdeI/XhoI site of pCDM4. The plasmid pETM6-H10-TmTrpB-2F3-V5-BaTDC-FLAG was created by first cloning the in-frame, C-terminally V5-tagged (SEQ.ID NO: 6, SEQ.ID NO: 7) TmTrpB-2F3 (SEQ.ID NO: 8, SEQ.ID NO: 9) into the NdeI/Xho site of pETM6-H10 (SEQ.ID NO: 10) to create pETM6-H10-TmTrpB-2F3-V5. This intermediate plasmid was digested with SpeI and SalI, and in-frame, C-terminally FLAG tagged (SEQ.ID NO: 2, SEQ.ID NO: 3) BaTDC (SEQ.ID NO: 11, SEQ.ID NO: 12) was cloned into the site with XbaI and SalI, nullifying the SpeI restriction site. In this setup, the T7 polymerase was able to drive the expression of the polycistronic DNA containing both TmTrpB-2F3 and BaTDC. The two target plasmids pCDM4-PsmF-FLAG and pETM6-H10-TmTrpB-2F3-V5-BaTDC-FLAG were transformed into BL21 (DE3) cells, and antibiotics ampicillin plus streptomycin were used to select for the correct clones containing both plasmids. Scaled-up culturing of engineered E. coli was conducted as follows: seed cultures were inoculated in AMM (Jones et al., 2015, Sci Rep. 5: 11301) medium overnight. The overnight culture was then divided into two flasks containing 500 mL each of AMM medium additionally containing 0.5% (w/v) serine, 1M IPTG, 50 ug/L ampicillin and Streptomyces, and 100 mg/L 7-methyl-1H-indole-5-carbonitrile (Advanced Chemblocks Inc, achemblock.com) for conversion by Ec-1. Cultures were grown for 24 h. Cultures were then centrifuged (10,000 g×5 minutes) to remove cellular content, and culture broth containing secreted derivative was stored at −80° C. until further processing. Analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific) equipped with a Poroshell 120 SB-C18 column (Agilent Technologies) instead of an Accela HPLC system (Thermo Fisher Scientific) equipped with a Zorbax C18 column (Agilent Technologies). Briefly, 10 microliters of culture media was injected at a flow rate of 0.5 mL/min and a gradient of solvent A (water with 0.1% of formic acid) and solvent B (ACN with 0.1% formic acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C.; source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-500 m/z. Ion injection time was 300 ms with scan time of 1 s. External and internal calibration procedures ensured <2 ppm error to facilitate elemental formulae predictions. Singly protonated product with exact n/z and expected elemental formula matching the singly protonated form of N-[2-(5-cyano-7-methyl-1H-indol-3-yl)ethyl]acetamide having chemical formula (VIII):

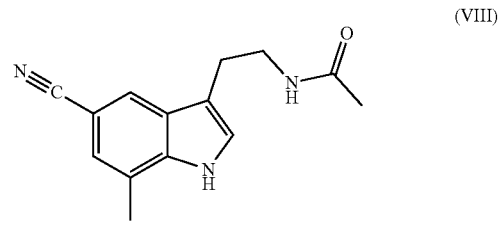 [SMILES: CC(=O)NCCc1c[nH]c2c(C)cc(C#N)cc12]

Figure 11:
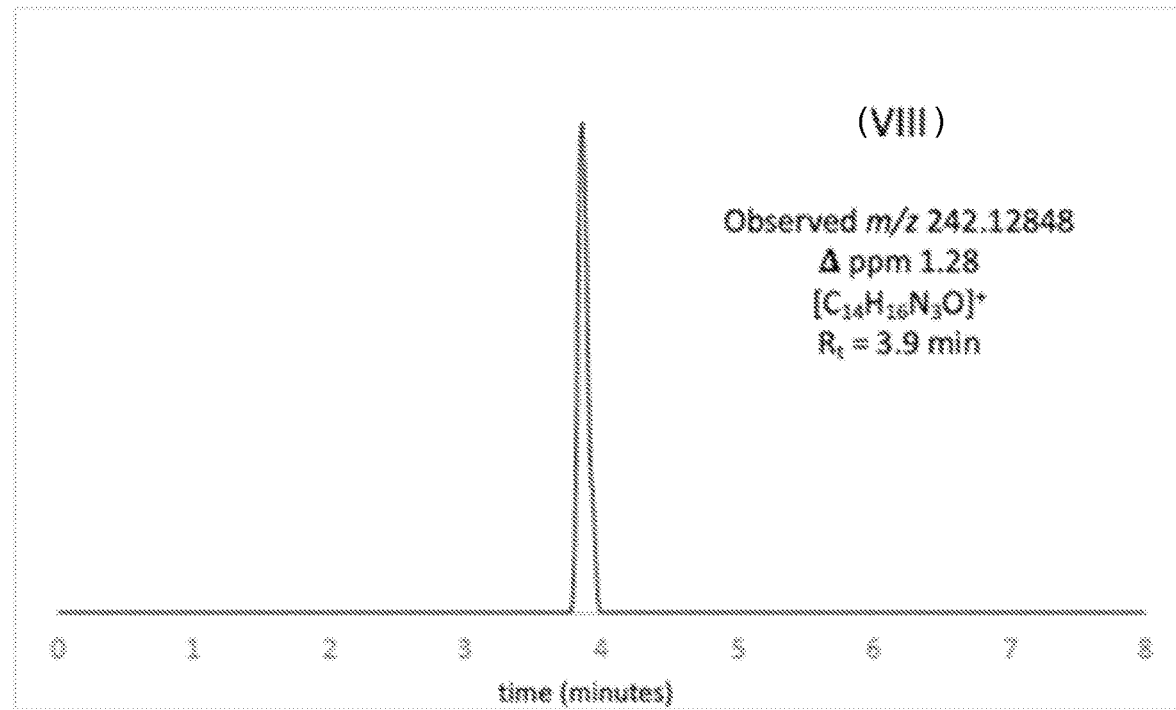
FIG. 11 depicts a representation of mass spectrometry data in the form of a chromatogram, notably a chromatogram obtained in the performance of an experiment to synthesize an example nitrilated psilocybin derivative compound having the chemical formula (VIII) set forth herein.

(VIII)

eluted at 3.9 minutes (EIC, see: FIG. 11). It is noted that the acetyl group of the compound having chemical formula (VIII) is included therein by virtue of the acetyl transferase having SEQ.ID NO: 5 in Escherichia coli strain Ec-1.

Figure 12:
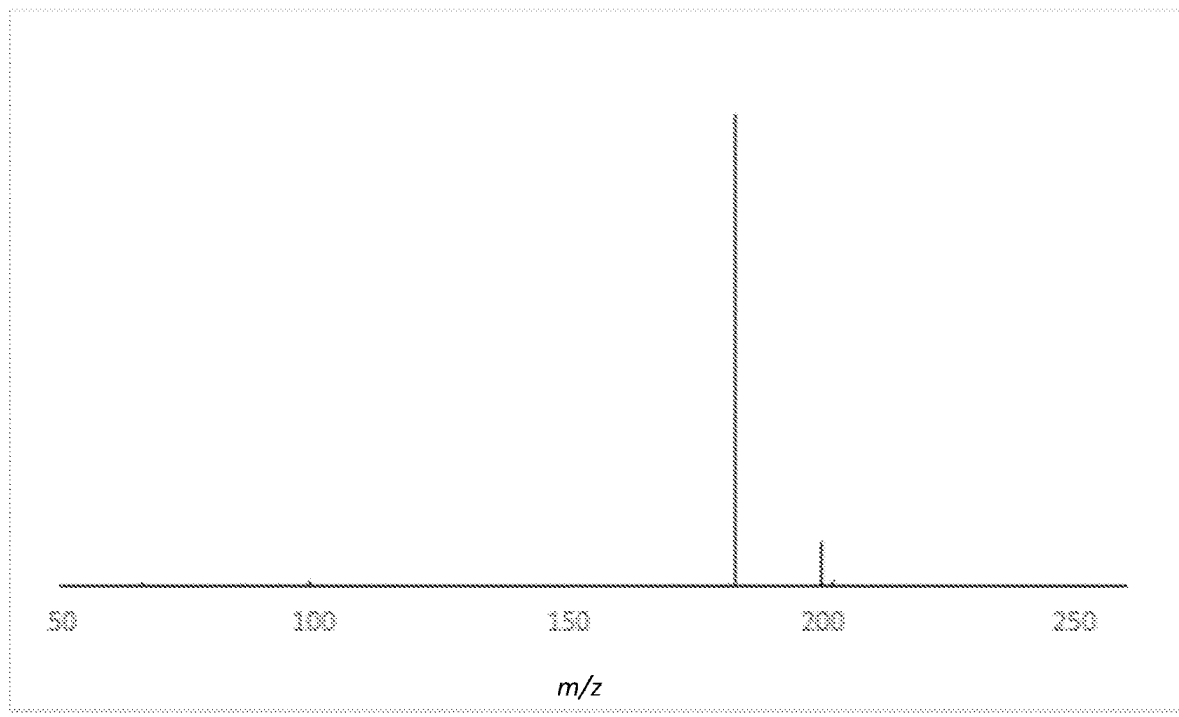
FIG. 12 depicts a representation of mass spectrometry data in the form of a mass spectrometry spectrum obtained in the performance of an experiment to identify a nitrilated psilocybin derivative compound having the chemical formula (VIII) set forth herein.

As per standard procedures (Menéndez-Perdomo et al., 2021, Mass Spectrom 56: 34683) high energy collision dissociation spectra (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (VIII), as follows (FIG. 12, Table 1):

TABLE 1

| m/z | % Relative abundance | Ionic fragment | Δ ppm |
|---|---|---|---|
| 183.09151 | 100 | $[M + H - NH_2C_2H_3O]^+$ | 0.87 |
| 200.11813 | 9 | $[M + H - C_2H_2O]^+$ | 0.45 |
| 202.35147 | 1 | | |
| 99.07905 | 1 | | |
| 66.12417 | 0.6 | | |
| 85.94969 | 0.4 | | |
| 181.73395 | 0.3 | | |
| 242.12839 | 0.2 | $[M + H]^+$ | 1.6 |

Product having the formula (VIII) was purified as follows: to 1 L of E. coli culture, 10M NaOH solution was added until the pH reached ~7. The culture was then extracted by ethyl acetate (4×600 ml). The organic layer was washed with brine and dried over $Na_2SO_4$, followed by concentration under reduced pressure. The residue was purified by flash chromatography on silica gel (1% methanol in dichloromethane), to give the compound as a white solid (25 mg). Following purification, high-resolution MS (HRMS), $^1$H NMR, and selective $^{13}$C NMR were performed to assess purity, estimate total quantity, and confirm molecular structure. $^1$H NMR (400 MHz, $CD_3OD$): δ=1.93 (s, 3H), 2.52 (s, 3H), 2.96 (t, J=7.2 Hz, 2H), 3.47 (m, 2H), 7.19 (s, 1H), 7.27 (s, 1H), 7.89 (s, 1H). $^{13}$C NMR (100 MHz, $CD_3OD$): δ=15.2, 21.2, 24.6, 40.0, 110.9, 113.7, 120.7, 121.9, 122.3, 123.7, 124.6, 127.0, 138.1, 171.9. HRMS (ESI) m/z: calcd. for $C_{14}H_{15}N_3O$ $[M+H]^+$ 242.1288, found 242.1284. Purity was assessed at 95%.

Assessment of Cell Viability Upon Treatment of Nitrilated Psilocybin Derivative

Figure 13A:
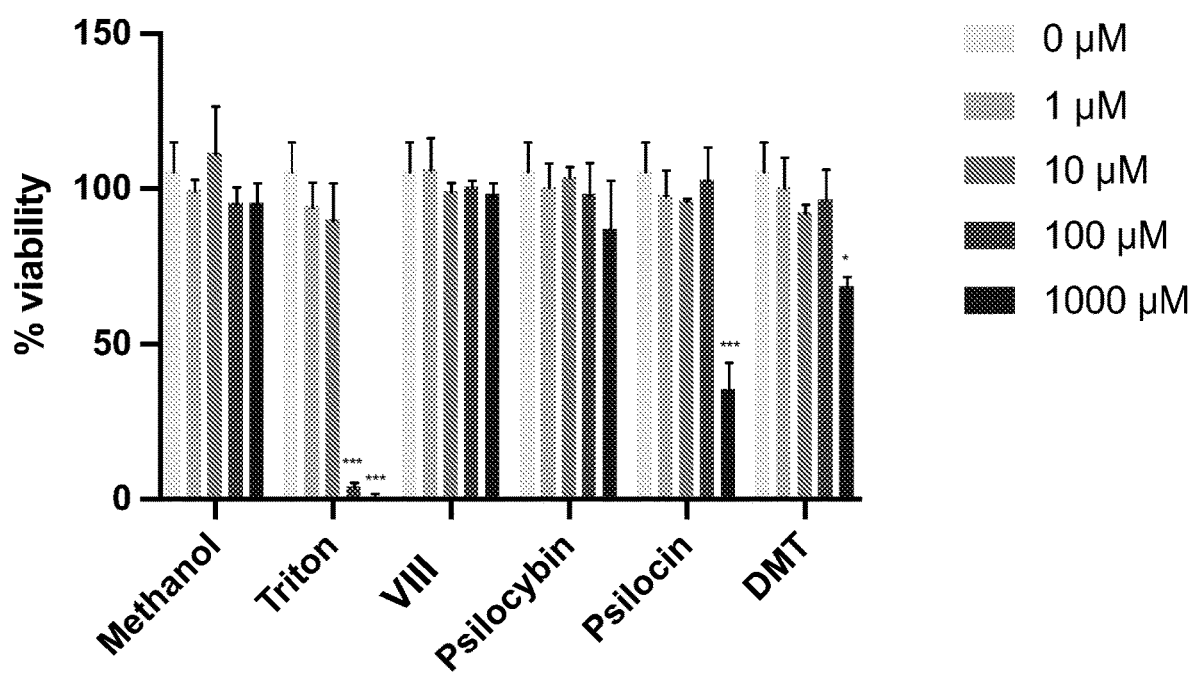
FIGS. 13A, 13B, 13C, 13D and 13E depict various graphs obtained in the performance of experimental assays to evaluate the efficacy of an example nitrilated psilocybin derivative having the chemical formula (VIII) set forth herein, notably a cell viability assay (FIG. 13A), a saturation binding assay for [$^3$H]ketansern at the 5-HT$_{2A}$ receptor (FIG. 13B), a competition assay for psilocin as a positive control (binding) (FIG. 13C), a competition assay for tryptophan as a negative control (no binding) (FIG. 13D), a competition assay for a nitrilated psilocybin compound with formula (VIII), designated "VIII".

To establish suitable ligand concentrations for competitive binding assays, PrestoBlue assays were first performed. The PrestoBlue assay measures cell metabolic activity based on tetrazolium salt formation, and is a preferred method for routine cell viability assays (Terrasso et al., 2017, J Pharmacol Toxicol Methods 83: 72). Results of these assays were conducted using both control ligands (e.g., psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Drug-induced changes in cell health within simple in vitro systems such as the HepG2 cell line are commonly adopted as first-line screening approaches in the pharmaceutical industry (Weaver et al., 2017, Expert Opin Drug Metab Toxicol 13: 767). HepG2 is a human hepatoma that is most commonly used in drug metabolism and hepatotoxicity studies (Donato et al., 2015, Methods Mol Biol 1250: 77). Herein, HepG2 cells were cultured using standard procedures using the manufacture's protocols (ATCC, HB-8065). Briefly, cells were cultured in Eagle's minimum essential medium supplemented with 10% fetal bovine serum and grown at 37° C. in the presence of 5% $CO_2$. To test the various compounds with the cell line, cells were seeded in a clear 96-well culture plate at 20,000 cells per well. After allowing cells to attach and grow for 24 hours, compounds were added at 1 μM, 10 μM, 100 μM, and 1 mM. Methanol was used as vehicle, at concentrations 0.001, 0.01, 0.1, and 1%. As a positive control for toxicity, TritonX concentrations used were 0.0001, 0.001, 0.01 and 0.1%. Cells were incubated with compounds for 48 hours before accessing cell viability with the PrestoBlue assay following the manufacture's protocol (ThermoFisher Scientific, P50200). PrestoBlue reagent was added to cells and allowed to incubate for 1 hour before reading. Absorbance readings were performed at 570 nm with the reference at 600 nm on a SpectraMax iD3 plate reader. Non-treated cells were assigned 100% viability. Bar graphs show the mean+/−SD, n=3. Significance was determined by 2-way ANOVA followed by Dunnett's multiple comparison test and is indicated by * ($P<0.0001$), ($P<0.001$), *($P<0.005$) (FIG. 13A).

Radioligand Receptor Binding Assays.

Figure 13B:
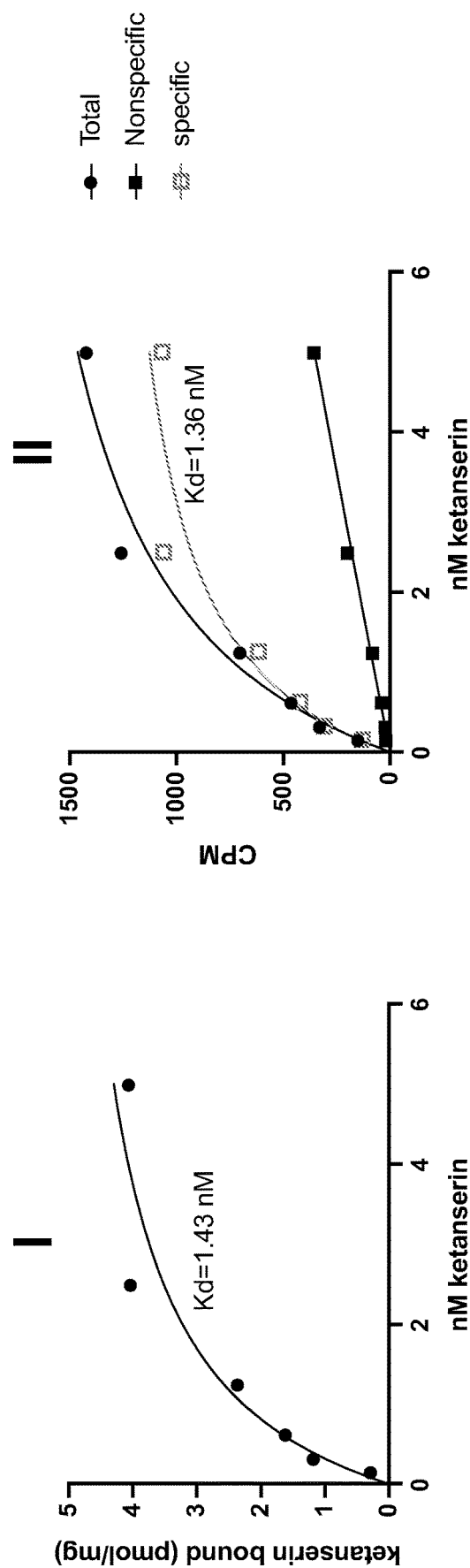
Figure 13C:
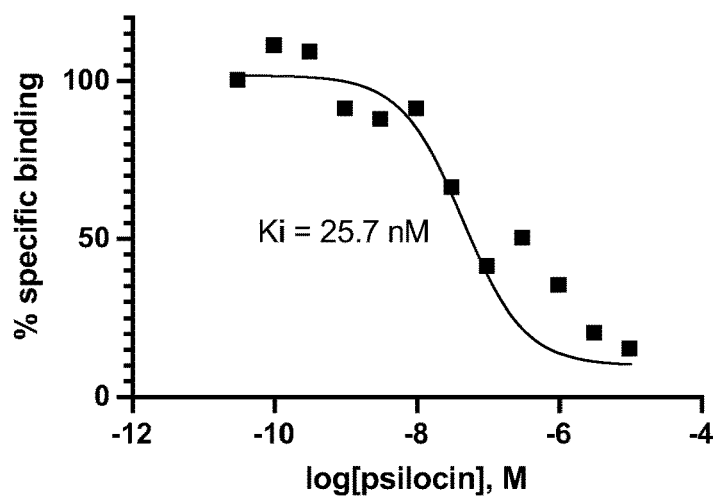
Figure 13D:
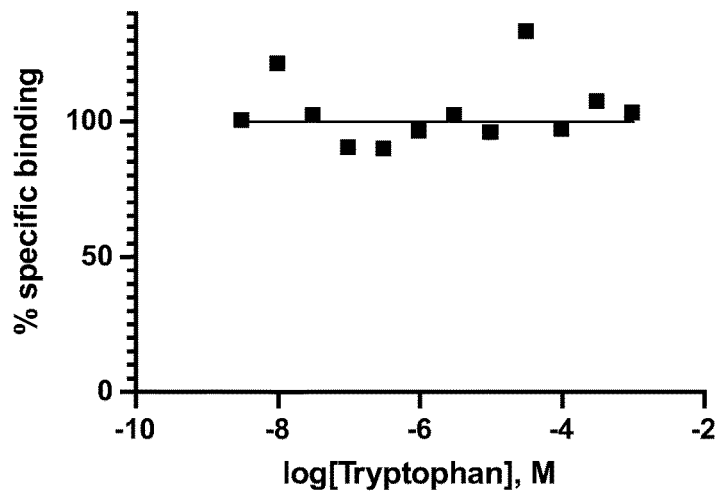
Figure 13E:
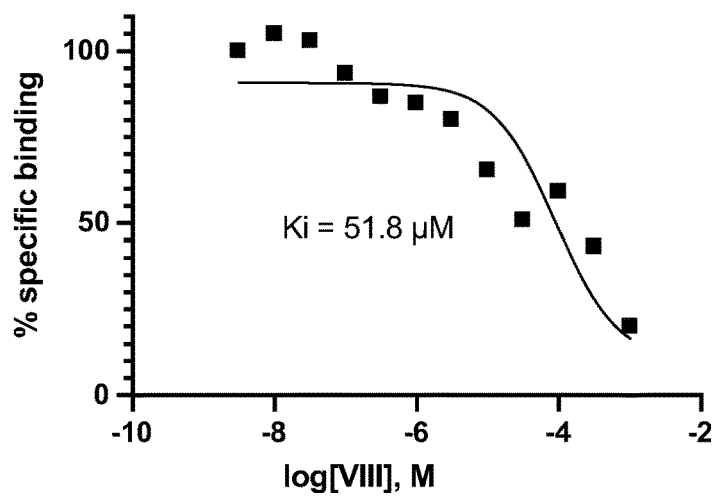

Evaluation of drug binding is an essential step to characterization of all drug-target interactions (Fang 2012, Exp Opin Drug Discov 7:969). The binding affinity of a drug to a target is traditionally viewed as an acceptable surrogate of its in vivo efficacy (Núñez et al., 2012, Drug Disc Today 17: 10). Competition assays, also called displacement or modulation binding assays, are a common approach to measure activity of a ligand at a target receptor (Flanagan 2016, Methods Cell Biol 132: 191). In these assays, standard radioligands acting either as agonists or antagonists are ascribed to specific receptors. In the case of G protein-coupled receptor 5-$HT_{2A}$, [$^3$H]ketanserin is a well-established antagonist used routinely in competition assays to evaluate competitive activity of novel drug candidates at the 5-$HT_{2A}$ receptor (Maguire et al., 2012, Methods Mol Biol 897: 31). Thus, to evaluate activity of novel nitrilated psilocybin derivatives at the 5-$HT_{2A}$ receptor, competition assays using [$^3$H]ketansern were employed as follows. SPA beads (RPNQ0010), [$^3$H] ketanserin (NET1233025UC), membranes containing 5-$HT_{2A}$ (ES-313-M400UA), and isoplate-96 microplate (6005040) were all purchased from PerkinElmer. Radioactive binding assays were carried out using Scintillation Proximity Assay (SPA). For saturation binding assays, mixtures of 10 ug of membrane containing 5-$HT_{2A}$ receptor was pre-coupled to 1 mg of SPA beads at room temperature in a tube rotator for 1 hour in binding buffer (50 mM Tris-HCl pH7.4, 4 mM $CaCl_2$, 1 mM ascorbic acid, 10 μM pargyline HCl). After pre-coupling, the beads and membrane were aliquoted in an isoplate-96 microplate with increasing amounts of [$^3$H]ketanserin (0.1525 nM to 5 nM) and incubated for two hours at room temperature in the dark with shaking. After incubation, the samples were read on a MicroBeta 2 Microplate Counter (Perkin Elmer). Determination of non-specific binding was carried out in the presence of 20 μM of spiperone (S7395-250MG, Sigma). Equilibrium binding constants for ketanserin ($K_d$) were determined from saturation binding curves using the 'one-site saturation binding analysis' method of GraphPad PRISM software (Version 9.2.0). Competition binding assays were performed using fixed (1 nM) [$^3$H] ketanserin and different concentrations of tryptophan (3 nM to 1 mM), psilocin (30 μM to 10 μM) or unlabelled test compounds (3 nM to 1 mM) similar to the saturation binding assay. $K_i$ values were calculated from the competition displacement data using the competitive binding analysis from GraphPad PRISM software. Tryptophan was included as a negative control as it has no activity at the 5-$HT_{2A}$ receptor. In contrast, psilocin was used as a positive control since it has established binding activity at the 5-$HT_{2A}$ receptor (Kim et al., 2020, Cell 182: 1574). FIG. 13B depicts the saturation binding curves for [$^3$H]ketanserin at the 5-HT$_{2A}$ receptor. Panel I shows the specific saturation ligand binding of [$^3$H]ketanserin (from 0.1525 nM to 5 nM) to membranes containing 5-HT$_{2A}$ receptor, which was obtained after subtracting non-specific binding values (shown in Panel II). Specific binding in counts per minute (cpm) was calculated by subtracting non-specific binding from total binding. Specific binding (pmol/mg) was calculated from pmol of [$^3$H]ketanserin bound per mg of protein in the assay. The K$_d$ was calculated by fitting the data with the one-site binding model of PRISM software (version 9.2.0). FIG. 13C shows the competition binding curve for psilocin as a positive control (binding). FIG. 13D shows the competition binding curve for tryptophan as a negative control (no binding). FIG. 13E shows competition binding curve for compound with formula (VIII), designated simply "VIII" in the figure.

Cell Lines and Control Ligands Used to Assess Activity at 5-HT$_{1A}$

CHO-K1/Gα$_{15}$ (GenScript, M00257) (−5-HT$_{1A}$) and CHO-K1/5-HT$_{1A}$/Gα$_{15}$ (GenScript, M00330) (+5-HT$_{1A}$) cells lines were used. Briefly, CHO-K$_1$/Gα$_{15}$ is a control cell line that constitutively expresses Gα$_{15}$ which is a promiscuous G$_q$ protein. This control cell line lacks any transgene encoding 5-HT$_{1A}$ receptors, but still respond to forskolin; thus, cAMP response to forskolin should be the same regardless of whether or not 5-HT$_{1A}$ agonists are present. Conversely, CHO-K1/5-HT$_{1A}$/Gα$_{15}$ cells stably express 5-HT$_{1A}$ receptor in the CHO-K1 host background. Notably, Gα$_{15}$ is a promiscuous G protein known to induce calcium flux response, present in both control and 5-HT$_{1A}$ cell lines. In +5-HT$_{1A}$ cells, Gα$_{15}$ may be recruited in place of G$_{αi/o}$, which could theoretically dampen cAMP response (Rojas and Fiedler 2016, Front Cell Neurosci 10: 272). Thus, we included two known 5-HT$_{1A}$ agonists, DMT (Cameron and Olson 2018, ACS Chem Neurosci 9: 2344) and serotonin (Rojas and Fiedler 2016, Front Cell Neurosci 10: 272) as positive controls to ensure sufficient cAMP response was observed, thereby indicating measurable recruitment of G$_{αi/o}$ protein to activated 5-HT$_{1A}$ receptors. In contrast, tryptophan is not known to activate 5-HT$_{1A}$ receptors, and was thus used as a negative control. Cells were maintained in complete growth media as recommended by supplier (GenScript) which is constituted as follows: Ham's F12 Nutrient mix (HAM's F12, GIBCO #11765-047) with 10% fetal bovine serum (FBS) (Thermo Scientific #12483020), 200 μg/ml zeocin (Thermo Scientific #R25005) and/or 100 μg/ml hygromycin (Thermo Scientific #10687010). The cells were cultured in a humidified incubator with 37° C. and 5% CO$_2$. Cells maintenance was carried out as recommended by the cell supplier. Briefly, vials with cells were removed from the liquid nitrogen and thawed quickly in 37° C. water bath. Just before the cells were completely thawed the vial's outside was decontaminated by 70% ethanol spray. The cells suspension was then retrieved from the vial and added to warm (37° C.) complete growth media, and centrifuged at 1,000 rpm for 5 minutes. The supernatant was discarded and the cell pellet was then resuspended in another 10 ml of complete growth media, and added to the 10 cm cell culture dish (Greiner Bio-One #664160). The media was changed every third day until the cells were about 90% confluent. The ~90% confluent cells were then split 10:1 for maintenance or used for experiment. As 5-HT1AR activation inhibits cAMP formation, the agonist activity of test molecules on 5-HT1AR was measured via the reduction in the levels of cAMP produced due to application of 4 μM forskolin. The change in intracellular cAMP levels due to the treatment of novel molecules was measured using cAMP-Glo Assay kit (Promega #V1501). Briefly, +5-HT$_{1A}$ cells were seeded on 1-6 columns and base −5-HT$_{1A}$ cells were seeded on columns 7-12 of the white walled clear bottom 96-well plate (Corning, #3903). Both cells were seeded at the density of 30,000 cells/well in 100 μl complete growth media and cultured 24 hrs in humidified incubator at 37° C. and 5% CO$_2$. On the experiment day, the media of cells was replaced with serum/antibiotic free culture media. Then the cells were treated for 20 minutes with test molecules dissolved in induction medium (serum/antibiotic free culture media containing 4 μM forskolin, 500 μM IBMX (isobutyl-1-methylxanthine, Sigma-Aldrich, Cat. #17018) and 100 μM (RO 20-1724, Sigma-Aldrich, Cat. #B8279)). Forskolin induced cAMP formation whereas IBMX and RO 20-1724 inhibited the degradation of cAMP. PKA was added to the lysate, mixed, and subsequently the substrate of the PKA was added. PKA was activated by cAMP, and the amount of ATP consumed due to PKA phosphorylation directly corresponded to cAMP levels in the lysate. Reduced ATP caused reduced conversion of luciferin to oxyluciferin, conferring diminished luminescence as the result of 5-HT$_{1A}$ activation.

Figure 14A:
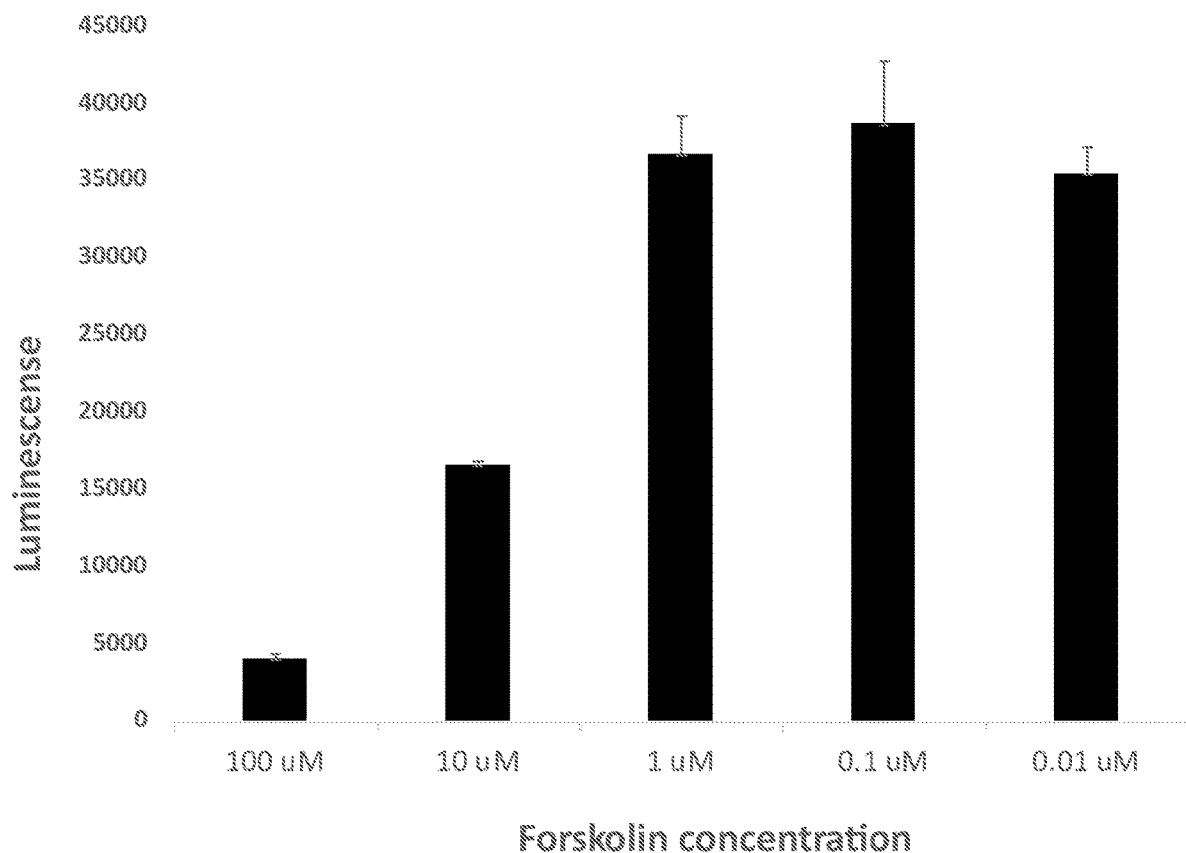
FIGS. 14A, 14B, 14C, 14D, 14E, 14F and 14G depict various further graphs, obtained in the performance of experimental assays to evaluate the efficacy of an example nitrilated psilocybin derivative having the chemical formula (VIII) set forth herein, notably a luminescence assay in +5HT$_{1A}$ cell cultures at various forskolin concentrations (FIG. 14A), a luminescence assay in +5HT$_{1A}$ cell cultures at various DMT concentrations (FIG. 14B), a luminescence assay in +5HT$_{1A}$ cell cultures at various concentrations of a nitrilated psilocybin compound having formula (VIII) designated "VIII" (FIG. 14C), a luminescence assay in +5HT$_{1A}$ cell cultures at various tryptophan concentrations (FIG. 14D), a cAMP assay upon treatment with increasing concentrations of forskolin in +5HT$_{1A}$ cells ("5-HT1AR") and −5HT$_{1A}$ cells ("CHO-K1") cells (FIG. 14E), a cAMP assay in the presence of constant (4 μM) forskolin but with increasing serotonin concentration in +5HT$_{1A}$ cells ("5-HT1AR") and −5HT$_{1A}$ cells ("CHO-K1") cells (FIG. 14F), and a cAMP assay in the presence of constant (4 μM) forskolin but with increasing concentration of a nitrilated psilocybin compound having formula (VIII), designated "VIII" in +5HT$_{1A}$ cells ("5-HT1AR") and −5HT$_{1A}$ cells ("CHO-K1") cells (FIG. 14G).
Figure 14B:
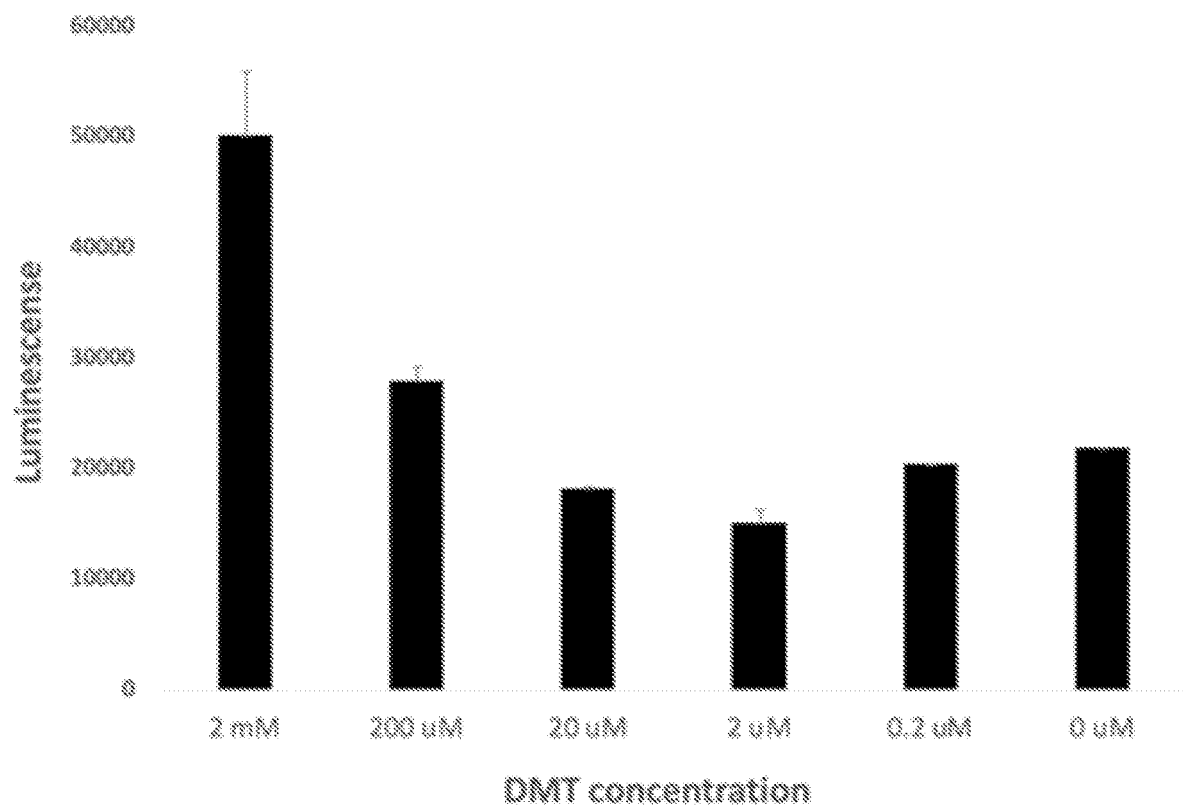
Figure 14C:
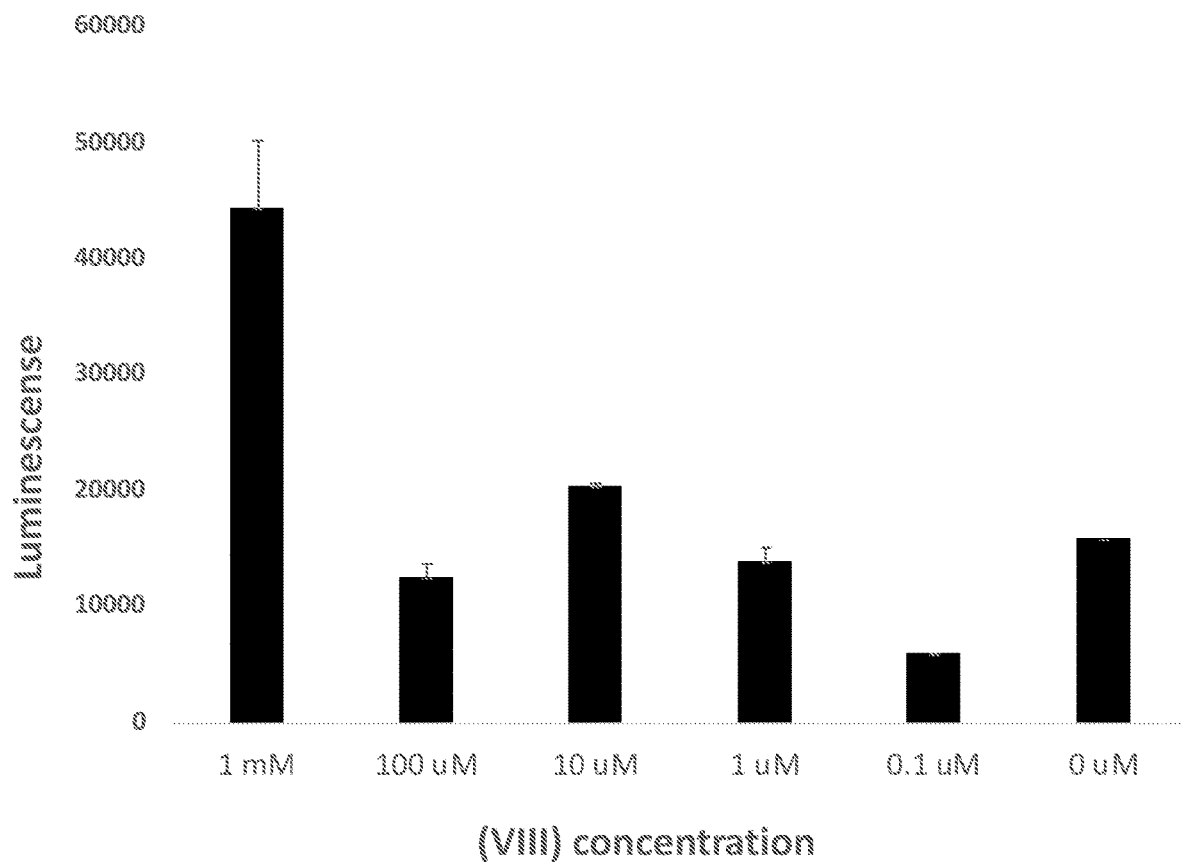
Figure 14D:
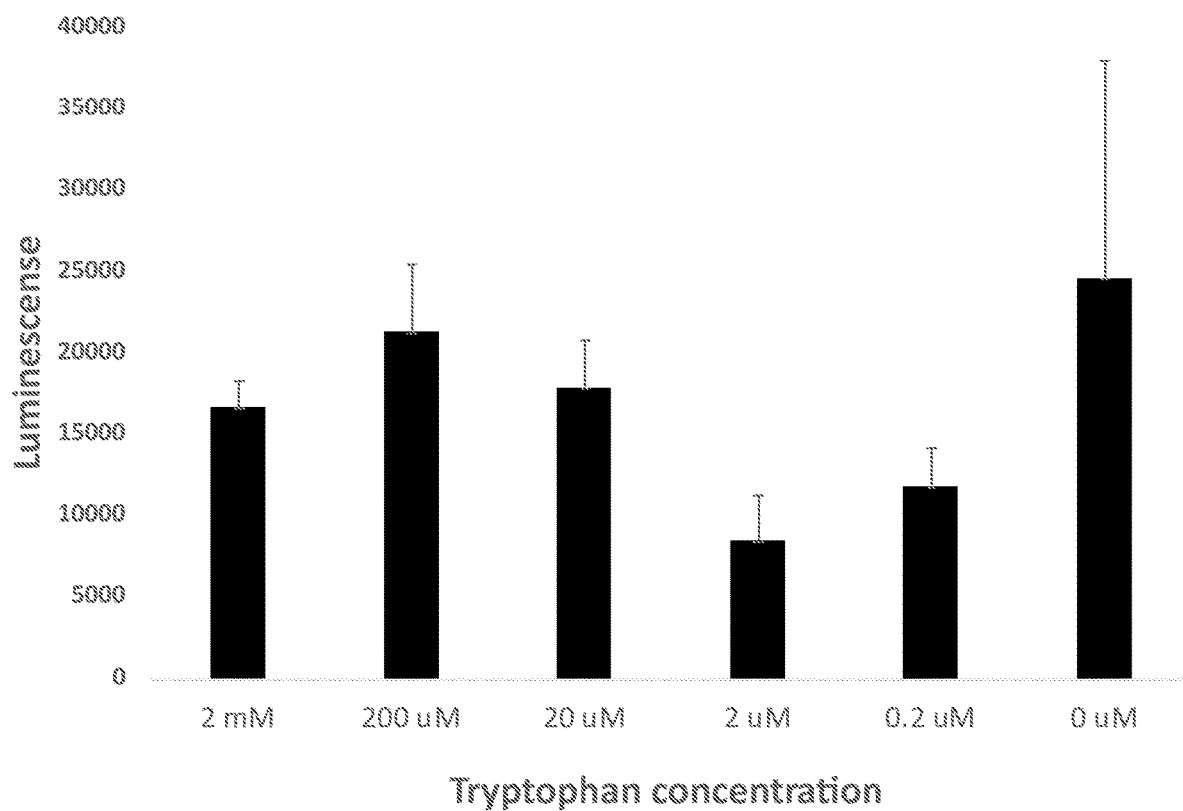
Figure 14E:
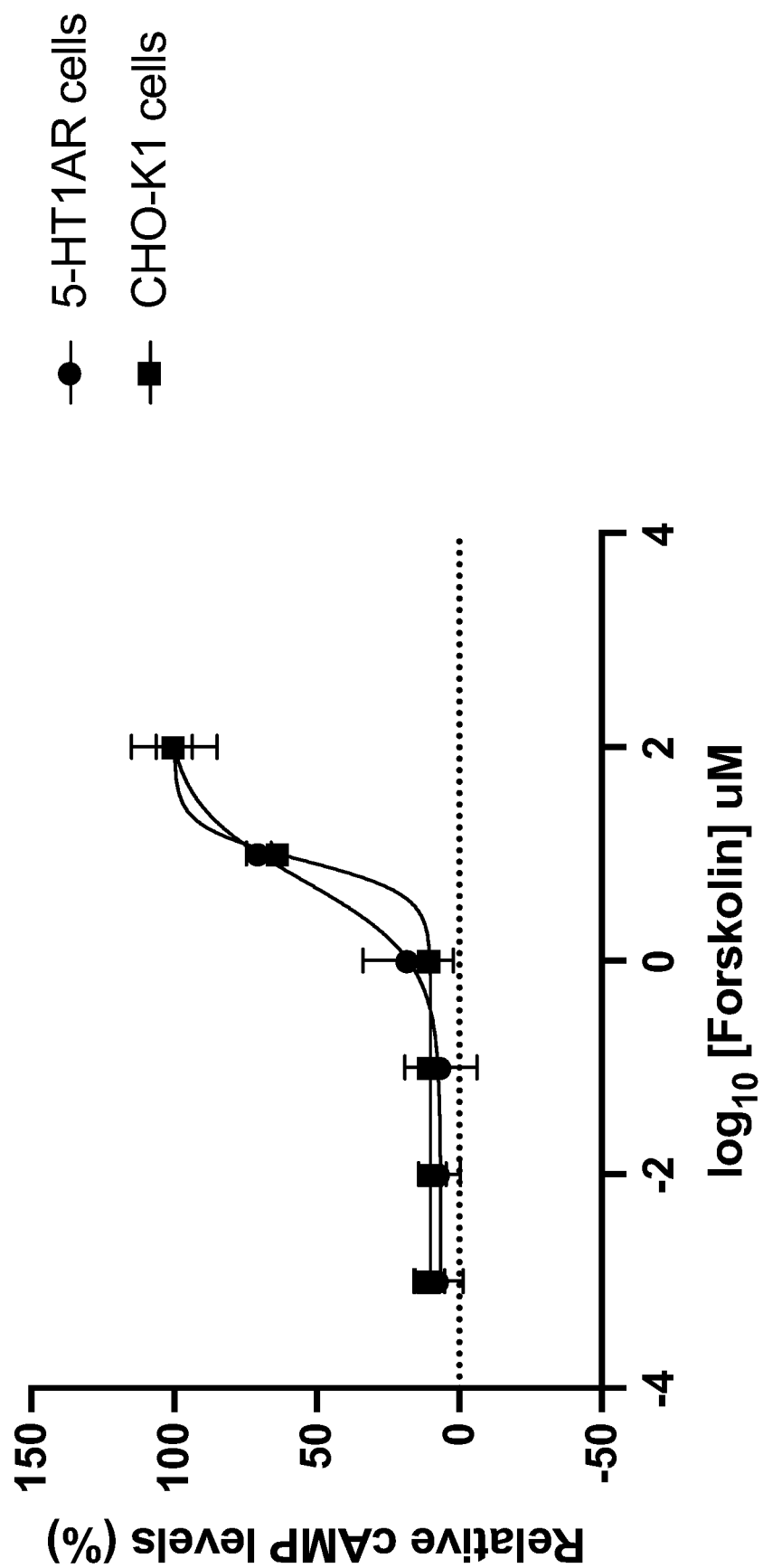
Figure 14F:
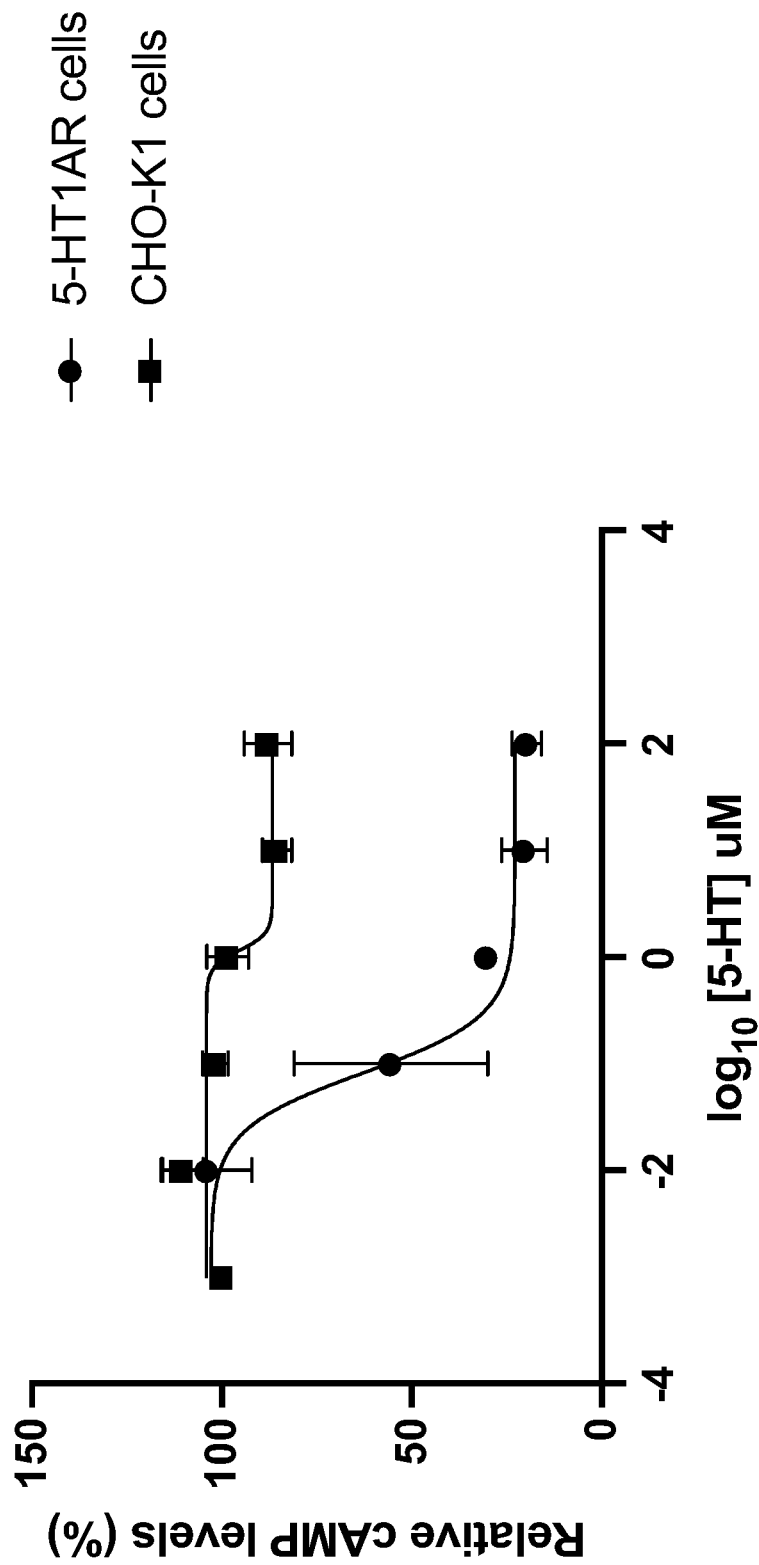
Figure 14G:
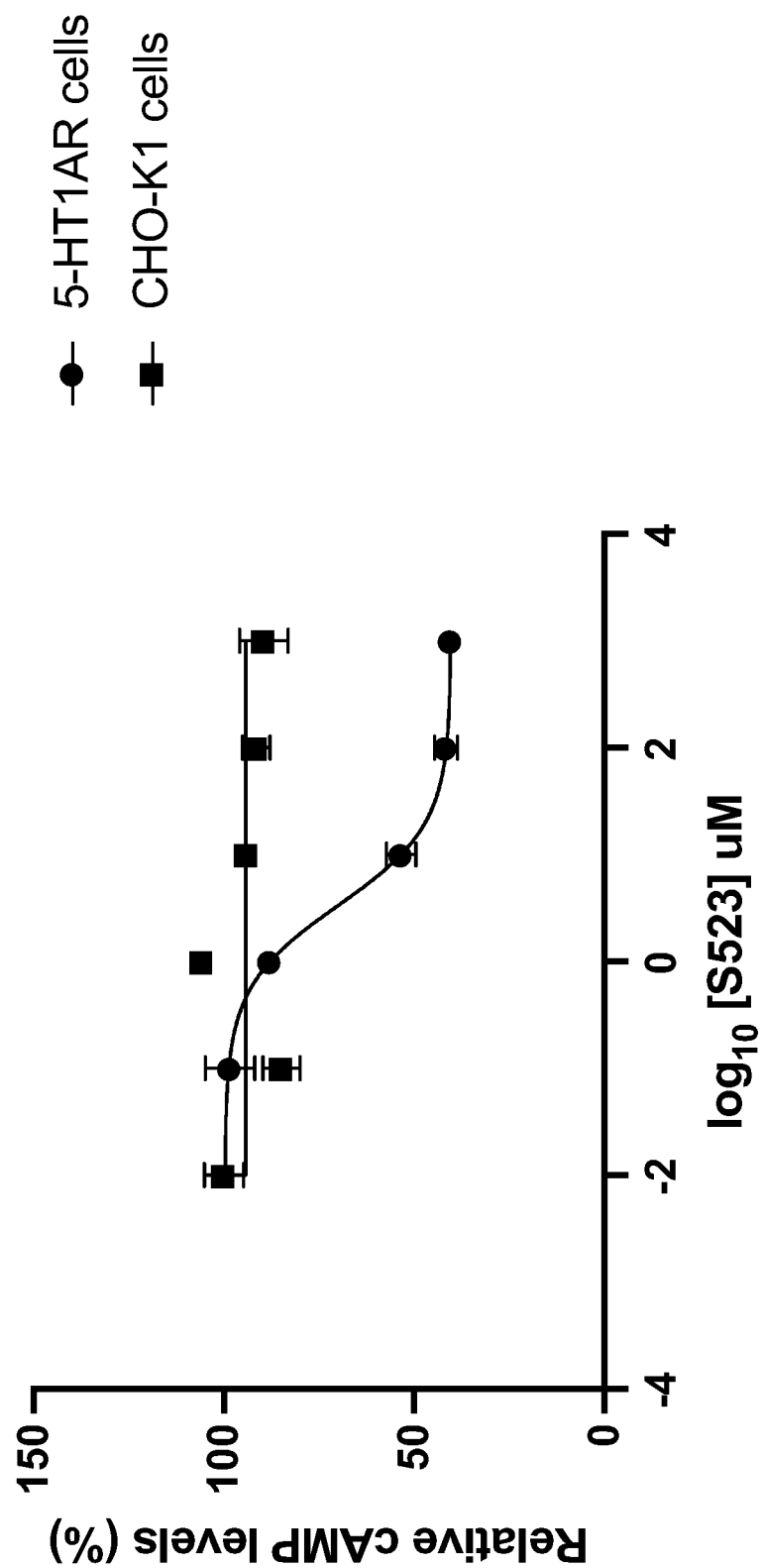

FIG. 14A shows increased luminescence resulting from decreased dosages of forskolin (and decreased cAMP) in +5HT$_{1A}$ cell culture. FIG. 14B illustrates reduced luminescence (i.e. increased cAMP) in the presence of fixed (4 μM) forskolin as dosages of DMT decrease, revealing 5-HT$_{1A}$ activity of DMT. FIG. 14C illustrates reduced luminescence (i.e. increased cAMP) in the presence of fixed (4 μM) forskolin as dosages of compound (VIII) decrease, revealing 5-HT$_{1A}$ activity of compound (VIII). FIG. 14D illustrates no trend in luminescence (i.e. no trend in cAMP levels) in the presence of fixed (4 μM) forskolin, as dosages of tryptophan decrease, revealing a lack of 5-HT$_{1A}$ activity for tryptophan. FIG. 14E illustrates relative cAMP levels upon treatment with increasing concentrations of forskolin. Note that since forskolin alters cAMP formation independently of 5-HT$_{1A}$ activity (it does not bind 5-H1A), the same trend is observed in +5HT$_{1A}$ and −5HT$_{1A}$ cells. This decrease in cAMP is observed only in +5HT$_{1A}$ cells, supporting serotonin's role as an agonist of 5HT$_{1A}$. FIG. 14F illustrates relative decrease in cAMP levels in the presence of constant (4 μM) forskolin but with increasing serotonin concentration. This decrease in cAMP is observed only in +5HT$_{1A}$ cells, supporting serotonin's role as an agonist of 5HT$_{1A}$. FIG. 14G illustrates relative decrease in cAMP levels in the presence of constant (4 μM) forskolin but with increasing concentration of nitrilated derivative (designated "VIII"). This decrease in cAMP is observed only in +5HT$_{1A}$ cells, supporting this derivative's role as an agonist of 5HT$_{1A}$. Note that for FIGS. 14E-14G, "5-HT1AR cells" refers to +5-HT$_{1A}$ culture, "CHO-K1 cells" refers to −5-HT$_{1A}$ culture, "5-HT" refers to serotonin, and "VIII" refers to nitrilated derivative with formula (VIII). Error bars represent results of three experiments (n=3) and curve fitting was performed using Graph-Pad Prism (Version 9.2.0).

Example 2—Synthesis of a Second Nitrilated Psilocybin Compound

*Escherichia coli* strain Ec-1 was used to biosynthesize nitrilated tryptamine derivative having chemical formula (VI) from nitrilated indole feedstock. The construction of Ec-1 is described in Example 1. Scaled-up culturing and material storage of engineered *E. coli* was conducted as described in Example 1, except that 6-cyanoindole (Combi-Blocks, www.combi-blocks.com) was used in place of 7-methyl-1H-indole-5-carbonitrile. To assess product, high-resolution LC-HESI-LTQ-Orbitrap-XL MS analysis was conducted as described in Example 1. Singly protonated product with exact m/z and expected elemental formula matching the singly protonated form of N-[2-(6-cyano-1H-indol-3-yl)ethyl]acetamide having chemical formula (VI):

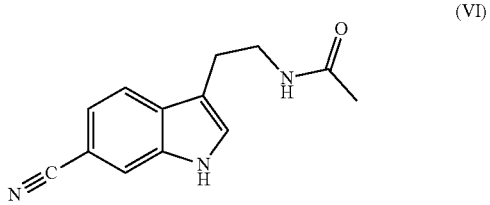 [SMILES: CC(=O)NCCc1c[nH]c2cc(C#N)ccc12]

Figure 15:
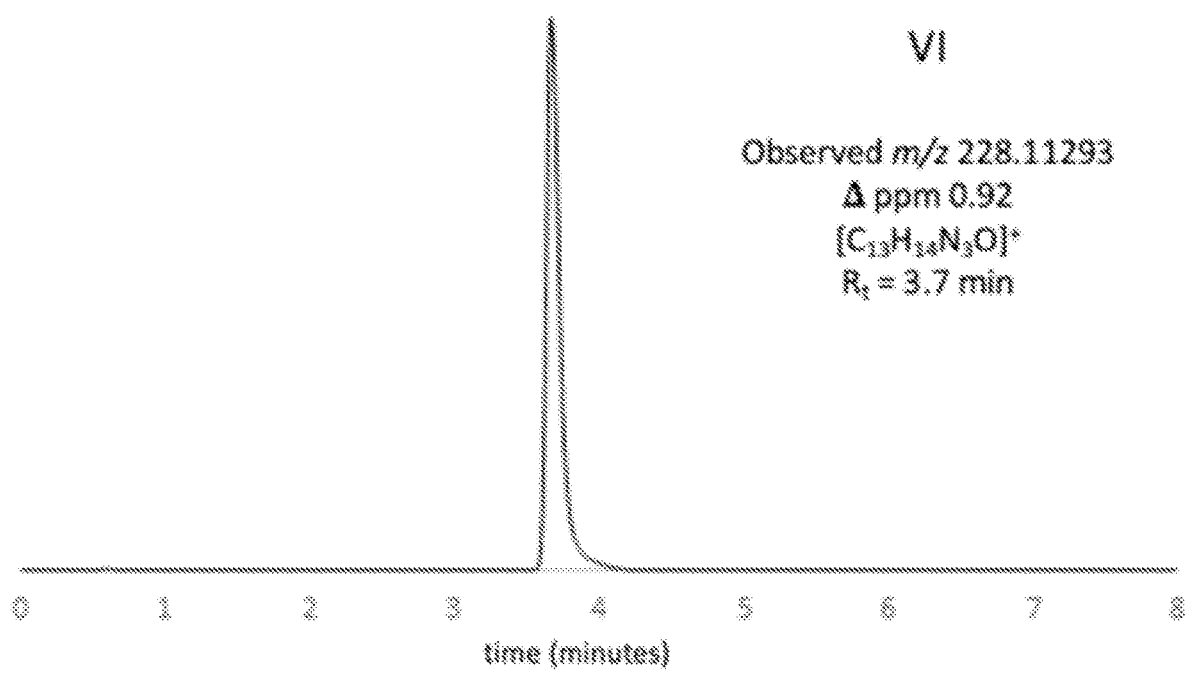
FIG. 15 depicts a representation of mass spectrometry data in the form of a chromatogram, notably a chromatogram obtained in the performance of an experiment to synthesize an example nitrilated psilocybin derivative compound having the chemical formula (VI) set forth herein.

(VI)

eluted at 3.7 minutes (EIC, see: FIG. 15). It is noted that the acetyl group of the compound having chemical formula (VI) is included therein by virtue of the acetyl transferase having SEQ.ID NO: 5 in *Escherichia coli* strain Ec-1.

Figure 16:
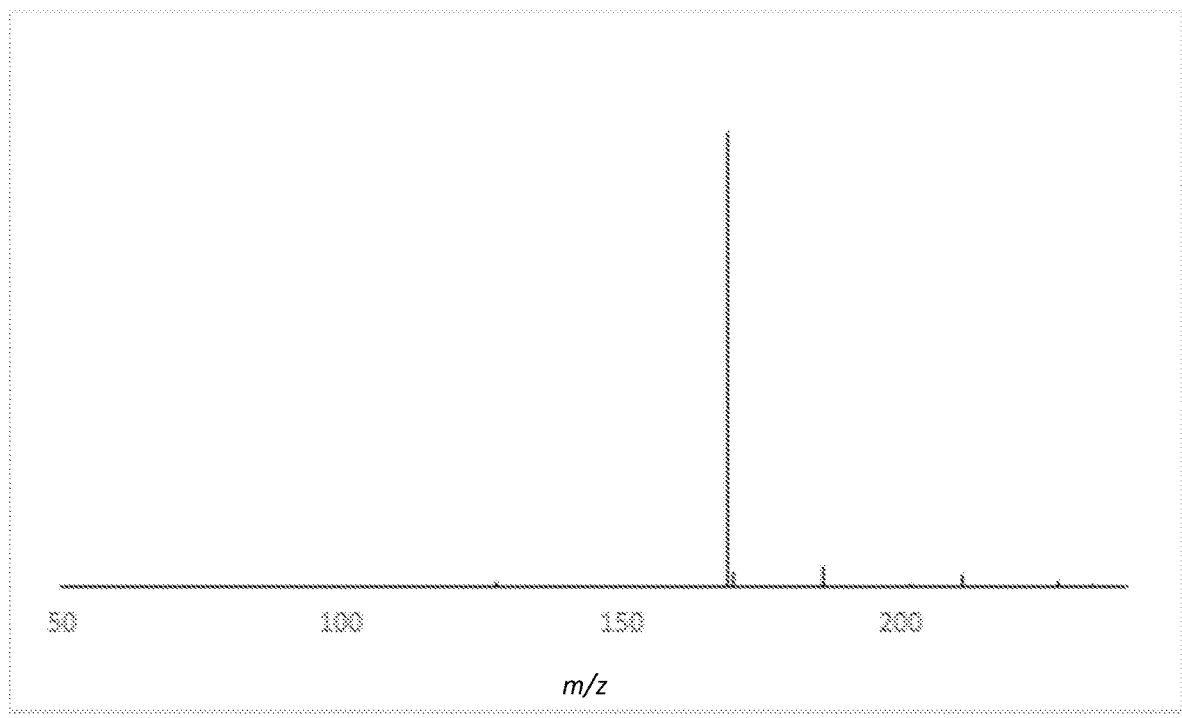
FIG. 16 depicts a representation of mass spectrometry data in the form of a mass spectrometry spectrum obtained in the performance of an experiment to identify a nitrilated psilocybin derivative compound having the chemical formula (VI) set forth herein.

As per standard procedures (Menéndez-Perdomo et al., 2021, Mass Spectrom 56: 34683) high energy collision dissociation spectra (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (VI), as follows (FIG. 16, Table 2):

TABLE 2

| m/z | % Relative abundance | Ionic fragment | Δ ppm |
|---|---|---|---|
| 169.07580 | 100 | $[M + H - NH_3C_2H_2O]^+$ | 1.30 |
| 186.10239 | 4 | $[M + H - C_2H_2O]^+$ | 0.97 |
| 170.07908 | 3 | | |
| 211.08646 | 3 | | |
| 228.11293 | 1 | $[M + H]^+$ | 0.92 |
| 127.80703 | 1 | | |

Example 3—Synthesis of a Third Nitrilated Psilocybin Compound

*Escherichia coli* strain E-1 was used to biosynthesize nitrilated tryptamine derivative having chemical formula (V) from nitrilated indole feedstock. The construction of Ec-1 is described in Example 1. Scaled-up culturing and material storage of engineered *E. coli* was conducted as described in Example 1, except that 5-cyanoindole (Combi-Blocks, www.combi-blocks.com) was used in place of 7-methyl-1H-indole-5-carbonitrile. To assess product, high-resolution LC-HESI-LTQ-Orbitrap-XL MS analysis was conducted as described in Example 1. Singly protonated product with exact m/z and expected elemental formula matching the singly protonated form of N-[2-(5-cyano-1H-indol-3-yl)ethyl]acetamide having chemical formula (V):

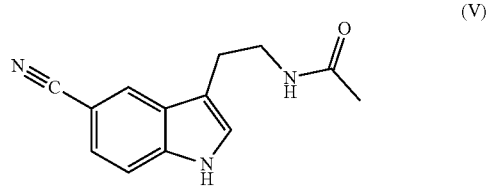 [SMILES: CC(=O)NCCc1c[nH]c2ccc(C#N)cc12]

Figure 17:
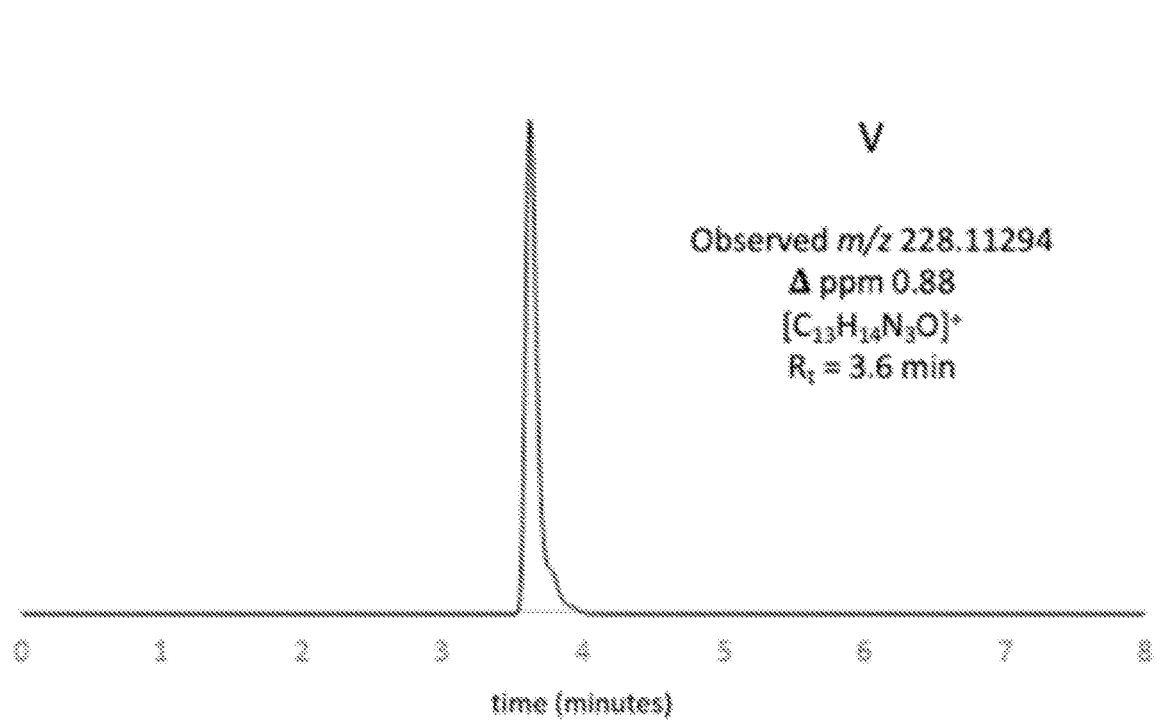
FIG. 17 depicts a representation of mass spectrometry data in the form of a chromatogram, notably a chromatogram obtained in the performance of an experiment to synthesize an example nitrilated psilocybin derivative compound having the chemical formula (V) set forth herein.

(V)

eluted at 3.6 minutes (EIC, see: FIG. 17). It is noted that the acetyl group of the compound having chemical formula (V) is included therein by virtue of the acetyl transferase having SEQ.ID NO: 5 in *Escherichia coli* strain Ec-1.

Figure 18:
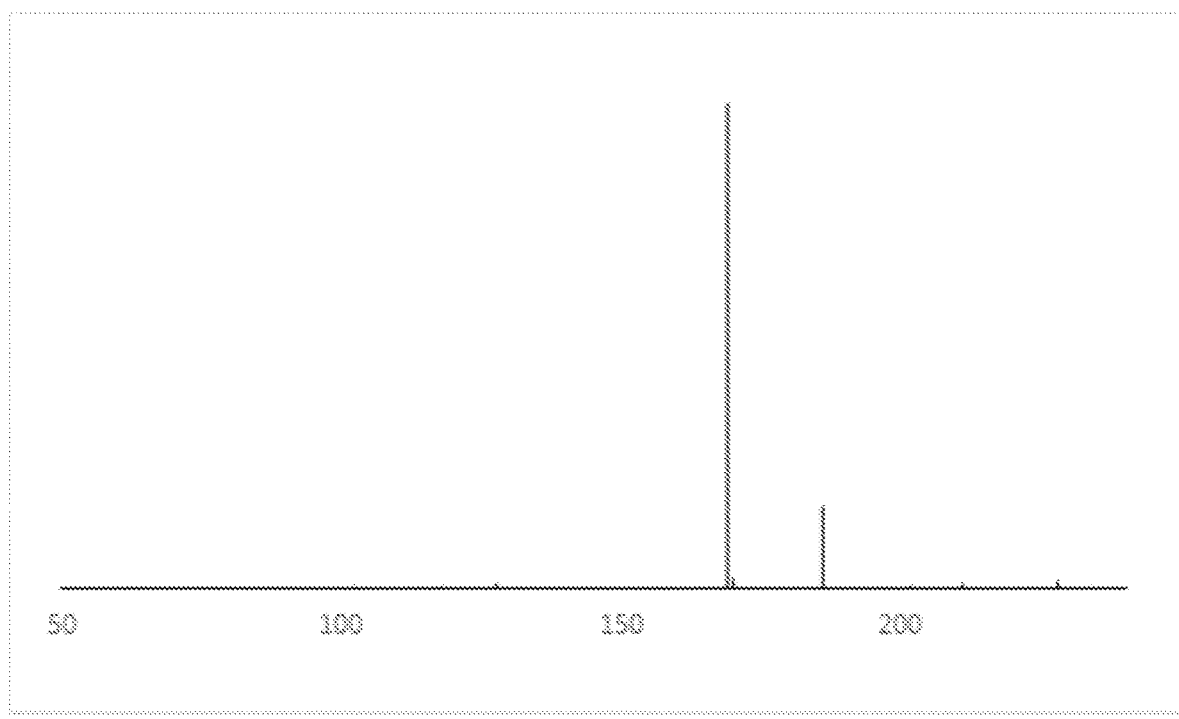
FIG. 18 depicts a representation of mass spectrometry data in the form of a mass spectrometry spectrum obtained in the performance of an experiment to identify a nitrilated psilocybin derivative compound having the chemical formula (V) set forth herein.

As per standard procedures (Menéndez-Perdomo et al., 2021, Mass Spectrom 56: 34683) high energy collision dissociation spectra (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (V), as follows (FIG. 18, Table 3):

TABLE 3

| m/z | % Relative abundance | Ionic fragment | Δ ppm |
|---|---|---|---|
| 169.07581 | 100 | $[M + H - NH_3C_2H_2O]^+$ | 1.24 |
| 186.10236 | 17 | $[M + H - C_2H_2O]^+$ | 1.12 |
| 170.07903 | 2 | | |
| 228.11294 | 2 | $[M + H]^+$ | 0.88 |
| 211.08635 | 0.9 | | |
| 127.80707 | 0.9 | | |
| 201.84565 | 0.6 | | |

Example 4—Synthesis of a Fourth Nitrilated Psilocybin Compound

*Escherichia coli* strain Ec-1 was used to biosynthesize nitrilated tryptamine derivative having chemical formula (VII) from nitrilated indole feedstock. The construction of Ec-1 is described in Example 1. Scaled-up culturing and material storage of engineered *E. coli* was conducted as described in Example 1, except that 6-methyl-1H-indole-5-carbonitrile (BLDpharm, www.bldpharm.com) was used in place of 7-methyl-1H-indole-5-carbonitrile. To assess product, high-resolution LC-HESI-LTQ-Orbitrap-XL MS analysis was conducted as described in Example 1. Singly protonated product with exact m/z and expected elemental formula matching the singly protonated form of N-[2-(5-cyano-6-methyl-1H-indol-3-yl)ethyl]acetamide having chemical formula (VII):

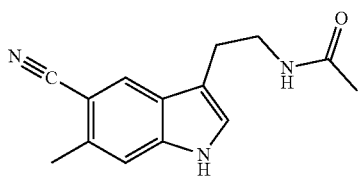

Figure 19:
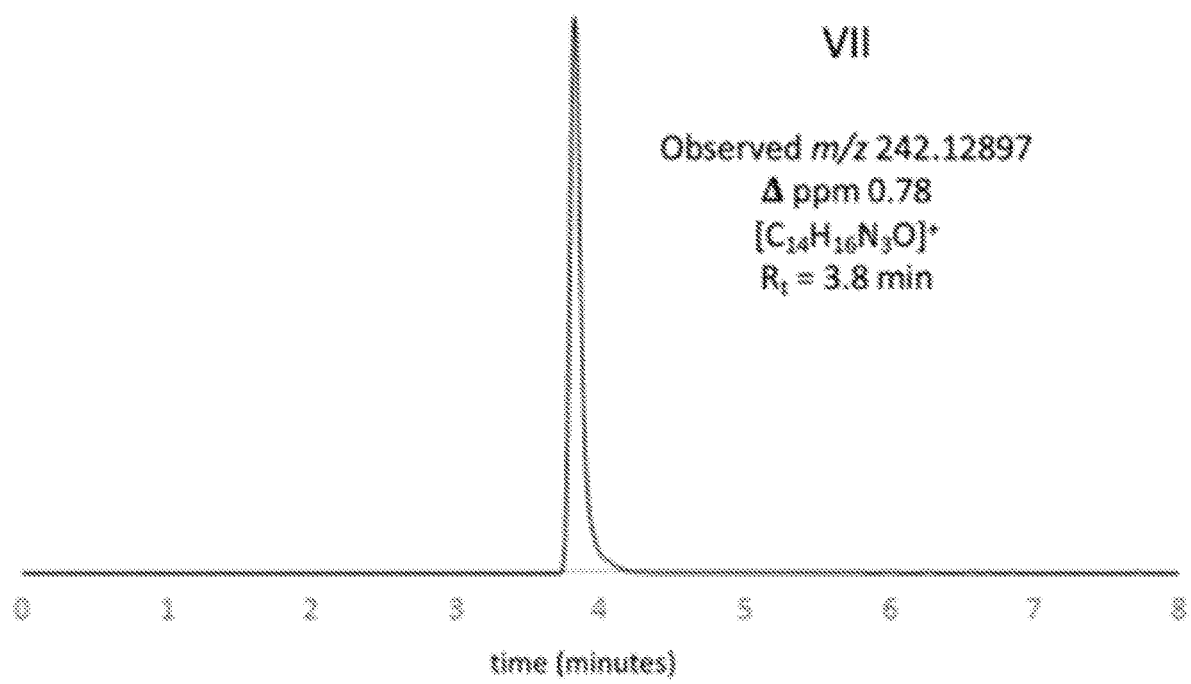
FIG. 19 depicts a representation of mass spectrometry data in the form of a chromatogram, notably a chromatogram obtained in the performance of an experiment to synthesize an example nitrilated psilocybin derivative compound having the chemical formula (VII) set forth herein.

(VII)

eluted at 3.8 minutes (EIC, see: FIG. 19). It is noted that the acetyl group of the compound having chemical formula (VII) is included therein by virtue of the acetyl transferase having SEQ.ID NO: 5 in *Escherichia coli* strain Ec-1.

Figure 20:
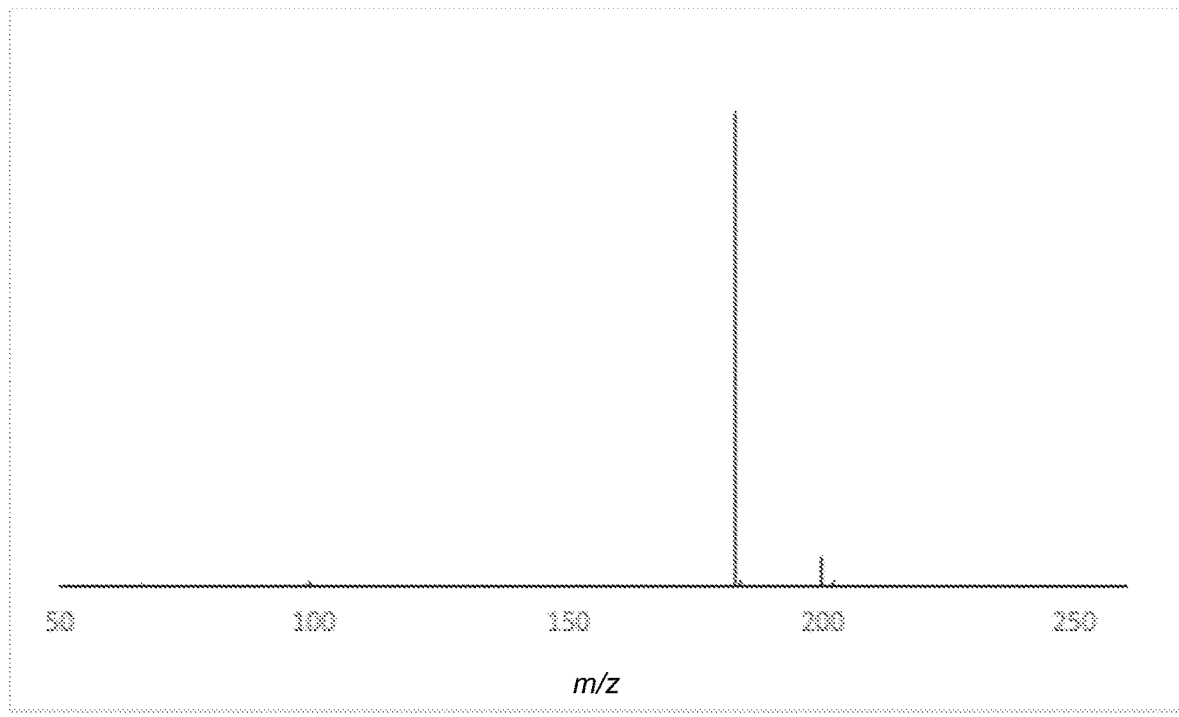
FIG. 20 depicts a representation of mass spectrometry data in the form of a mass spectrometry spectrum obtained in the performance of an experiment to identify a nitrilated psilocybin derivative compound having the chemical formula (VII) set forth herein.

As per standard procedures (Menéndez-Perdomo et al., 2021, Mass Spectrom 56: 34683) high energy collision dissociation spectra (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (VII), as follows (FIG. 20, Table 4):

TABLE 4

| m/z | % Relative abundance | Ionic fragment | Δ ppm |
|---|---|---|---|
| 183.09149 | 100 | $[M + H - NH_2C_2H_3O]^+$ | 0.98 |
| 200.11810 | 6 | $[M + H - C_2H_2O]^+$ | 0.60 |
| 99.07963 | 1 | | |
| 202.41332 | 1 | | |
| 66.12428 | 0.4 | | |
| 171.09153 | 0.3 | | |
| 181.73407 | 0.2 | | |
| 242.12897 | 0.1 | $[M + H]^+$ | 0.78 |

Product having the formula VII was purified as follows: To 1 L of *E. coli* culture, 10M NaOH solution was added until the pH reached ~7. The culture was then extracted by ethyl acetate (4×800 ml). The organic layer was washed with brine and dried over $Na_2SO_4$, followed by concentration under reduced pressure. The residue was purified by flash chromatography on silica gel (1% methanol in dichloromethane), to give the compound as a white solid (3 mg). Following purification, high-resolution MS (HRMS) and $^1H$ NMR were performed to estimate total quantity and confirm molecular structure. $^1H$ NMR (400 MHz, $CD_3OD$): δ=1.93 (s, 3H), 2.59 (s, 3H), 2.95 (t, J=7.4 Hz, 2H), 3.47 (t, J=7.6 Hz, 2H), 7.19 (s, 1H), 7.33 (s, 1H), 7.97 (s, 1H). HRMS (ESI) m/z: calcd. for $C_{14}H_{15}N_3O$ $[M+H]^+$ 242.1288, found 242.1284.

Example 5—Synthesis of a Fifth Nitrilated Psilocybin Compound

*E. coli* strain Ec-2 was constructed as follows. For plasmid cloning, Top10 or XL1-blue strains were used depending on antibiotic markers. Standard LB media was used for culturing. For gene expression and feeding experiments, the parent host strain employed was BL21 (DE3). The plasmid pETM6-H10-TmTrpB-2F3-V5-BaTDC-FLAG was created as described in Example 1. This plasmid was transformed into BL21 (DE3) cells followed by ampicillin selection. Scaled-up culturing and material storage of engineered *E. coli* was conducted as described in Example 1, except that only one antibiotic was needed for selection. To assess product, high-resolution LC-HESI-LTQ-Orbitrap-XL MS analysis was conducted as described in Example 1. Singly protonated product with exact n/z and expected elemental formula matching the singly protonated form of 3-(2-aminoethyl)-7-methyl-1H-indole-5-carbonitrile having chemical formula (III):

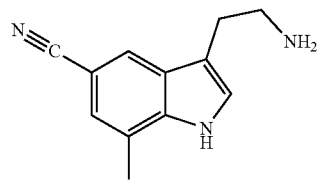

Figure 21:
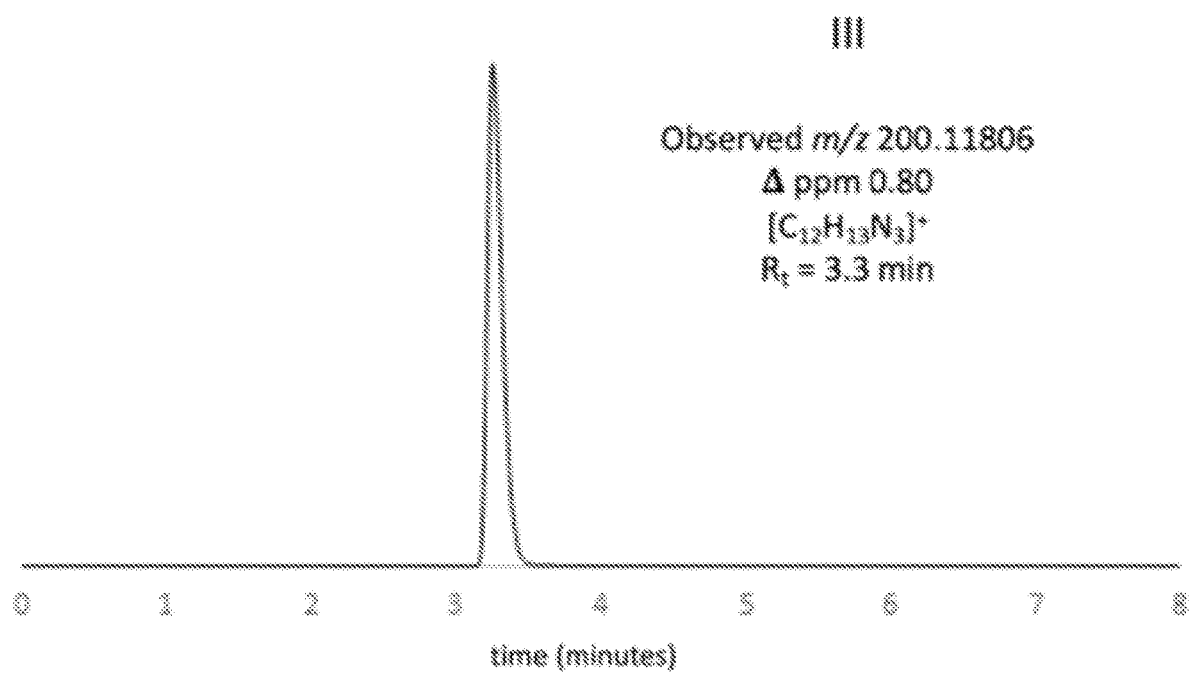
FIG. 21 depicts a representation of mass spectrometry data in the form of a chromatogram, notably a chromatogram obtained in the performance of an experiment to synthesize an example nitrilated psilocybin derivative compound having the chemical formula (III) set forth herein.

(III)

eluted at 3.3 minutes (EIC, see: FIG. 21).

Figure 22:
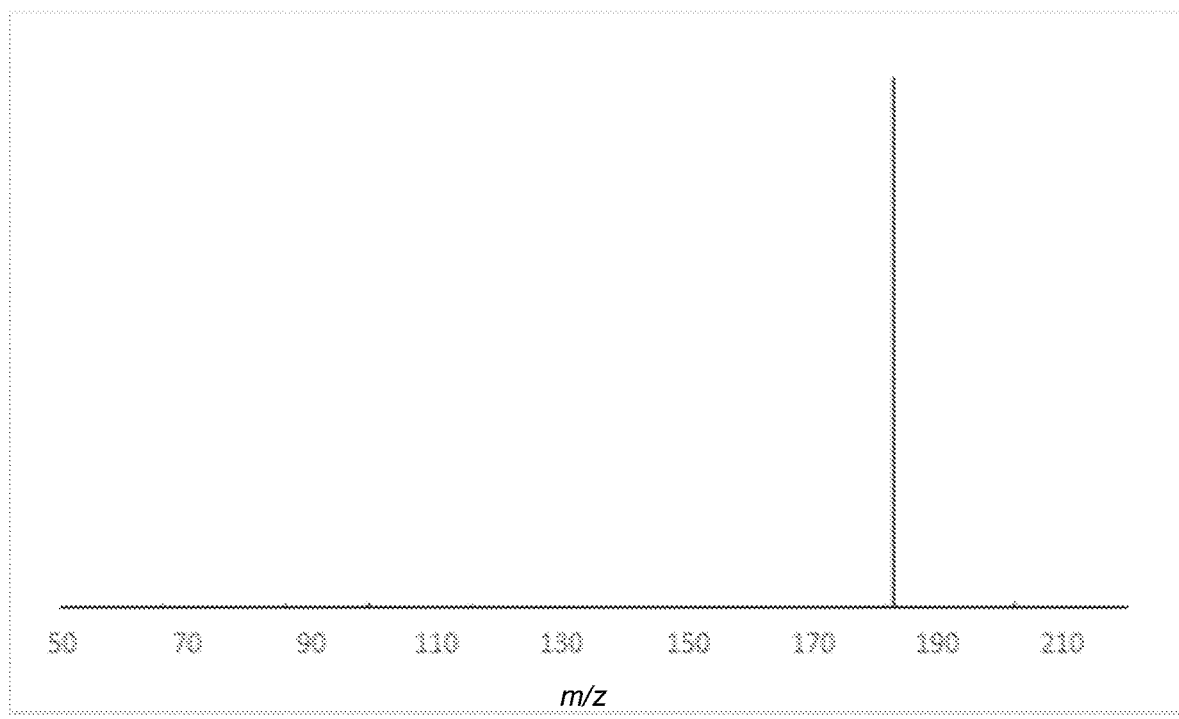
FIG. 22 depicts a representation of mass spectrometry data in the form of a mass spectrometry spectrum obtained in the performance of an experiment to identify a nitrilated psilocybin derivative compound having the chemical formula (III) set forth herein.

As per standard procedures (Menéndez-Perdomo et al., 2021, Mass Spectrom 56: 34683) high energy collision dissociation spectra (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (III), as follows (FIG. 22, Table 5):

TABLE 5

| m/z | % Relative abundance | Ionic fragment | Δ ppm |
|---|---|---|---|
| 183.09151 | 100 | $[M + H - NH_3]^+$ | 0.87 |
| 202.34942 | 1 | | |
| 99.07922 | 0.8 | | |
| 66.12423 | 0.5 | | |
| 85.94982 | 0.5 | | |
| 115.46394 | 0.4 | | |

Example 6—Synthesis of a Sixth Nitrilated Psilocybin Compound

*Escherichia coli* strain Ec-2 was used to biosynthesize nitrilated tryptamine derivative having chemical formula (IV) from nitrilated indole feedstock. The construction of Ec-2 is described in Example 5. Scaled-up culturing and material storage of engineered *E. coli* was conducted as described in Example 5, except that 6-methyl-1H-indole-5-carbonitrile (BLDpharm, www.bldpharm.com) was used in place of 7-methyl-1H-indole-5-carbonitrile. To assess product, high-resolution LC-HESI-LTQ-Orbitrap-XL MS analysis was conducted as described in Example 1. Singly protonated product with exact m/z and expected elemental formula matching the singly protonated form of 3-(2-aminoethyl)-6-methyl-1H-indole-5-carbonitrile having chemical formula (IV):

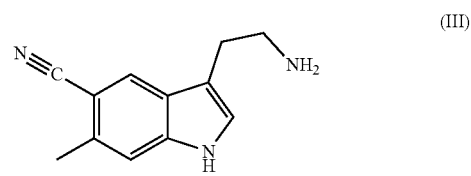

Figure 23:
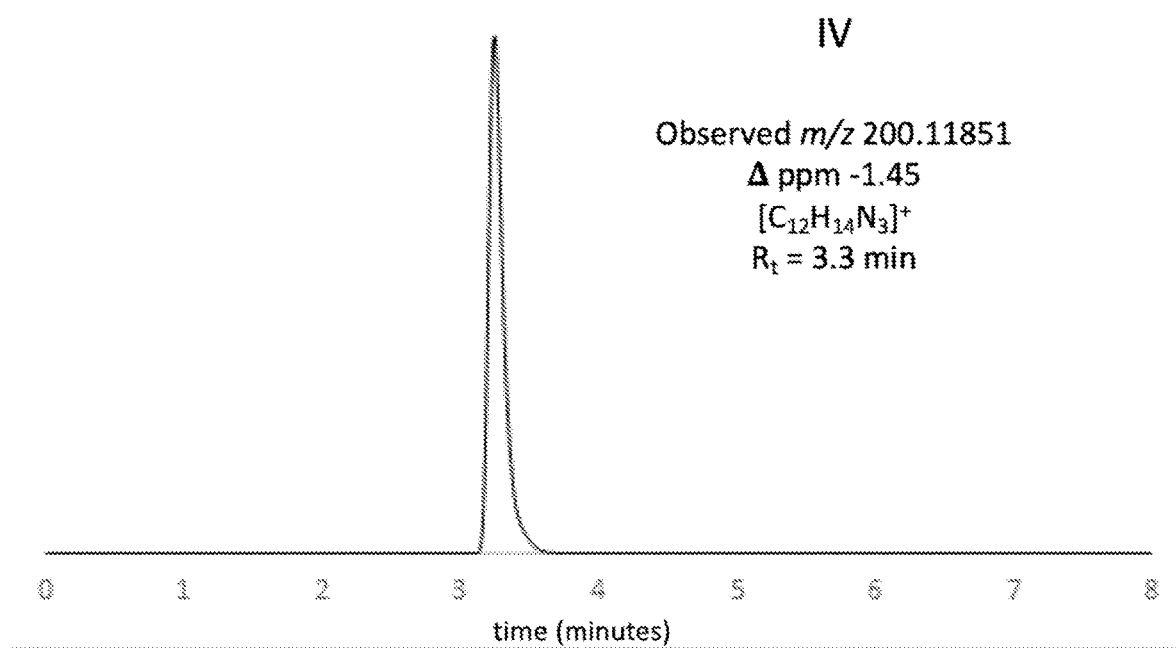
FIG. 23 depicts a representation of mass spectrometry data in the form of a chromatogram, notably a chromatogram obtained in the performance of an experiment to synthesize an example nitrilated psilocybin derivative compound having the chemical formula (IV) set forth herein.

(III)

eluted at 3.3 minutes (EIC, see: FIG. 23).

Figure 24:
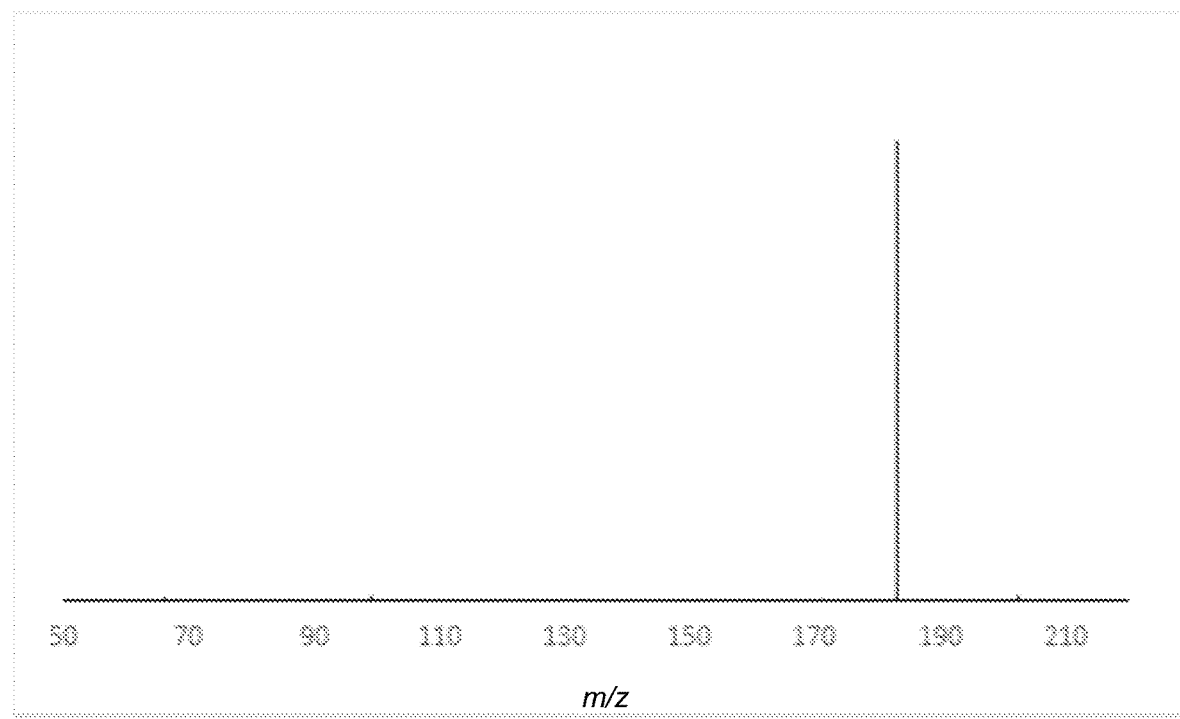
FIG. 24 depicts a representation of mass spectrometry data in the form of a mass spectrometry spectrum obtained in the performance of an experiment to identify a nitrilated psilocybin derivative compound having the chemical formula (IV) set forth herein.

As per standard procedures (Menéndez-Perdomo et al., 2021, Mass Spectrom 56: 34683) high energy collision dissociation spectra (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (IV), as follows (FIG. 24, Table 6):

TABLE 6

| m/z | % Relative abundance | Ionic fragment | Δ ppm |
|---|---|---|---|
| 183.09150 | 100 | $[M + H - NH_3]^+$ | 0.93 |
| 202.40089 | 1 | | |
| 99.07963 | 1 | | |
| 66.12427 | 0.5 | | |
| 85.95016 | 0.4 | | |
| 171.09146 | 0.3 | | |
| 199.98333 | 0.2 | | |

Example 7—Synthesis of a Seventh Nitrilated Psilocybin Compound

A seventh nitrilated psilocybin compound was synthesized in three steps as follows. The first step involved the preparation of a 7-formyl derivative (2) of psilocin:

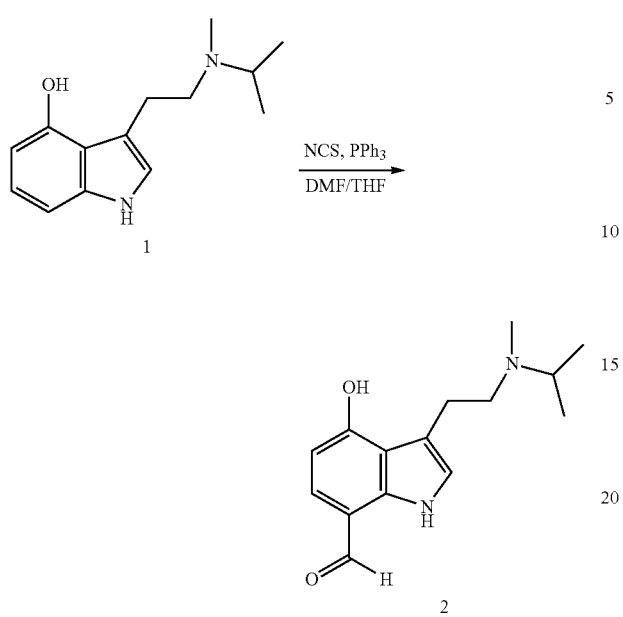

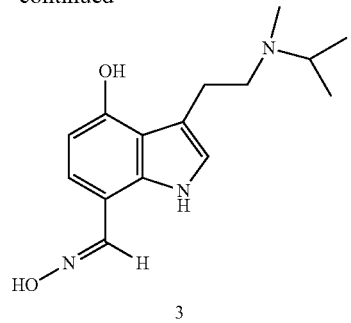

To a solution of triphenylphosphine (0.68 g, 2.59 mmol) in anhydrous THF (6.0 mL) was added N-chlorosuccinimide (0.34 g, 2.55 mmol), and the reaction mixture was stirred at room temperature for 30 minutes then cooled in an ice-water bath. Anhydrous DMF (0.4 mL) was added, and the reaction mixture was stirred for another 10 minutes. To the reaction mixture, was added 4-hydroxy-N-methyl-N-isopropyltryptamine (1, 0.20 g, 0.86 mmol), and the reaction mixture was heated at 60° C. for 23 hours. A solution of 10% NaOH was added until pH ~9-10 and the reaction mixture was stirred at room temperature for an hour before being neutralized with concentrated hydrochloric acid to pH 7-8. The reaction mixture was extracted with dichloromethane (2×20 mL), and the combined organic solutions was washed with brine (10 mL), dried over anhydrous $Na_2SO_4$, and concentrated in vacuo. The crude product was purified by flash chromatography on silica gel using a gradient of dichloromethane-MeOH (100:0 á 90:10) to afford compound 2 as a brown oil. $^1$H NMR (400 MHz, $CD_3OD$) δ 9.55 (s, 1H), 7.42 (d, J=8.3 Hz, 1H), 6.99 (s, 1H), 6.36 (d, J=8.3 Hz, 1H), 3.21-3.14 (m, 4H), 2.70 (s, 3H), 1.19 (d, J=6.7 Hz, 6H). HRMS (ESI, positive) m/z for $C_{15}H_{21}N_2O_2$ [M+H]$^+$ calc'd: 261.1598; found 261.1594.

The second step involved the preparation of a 7-oxime derivative (3) of psilocin:

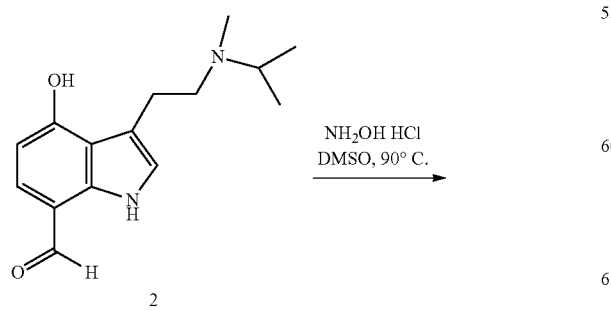

To a solution of aldehyde derivative 2 (1.0 eq.) in anhydrous DMSO, was added 1.5 eq. of $NH_2OH.HCl$, and the reaction mixture was stirred at 90° C. for 5 hours. The reaction was monitored by TLC (10% MeOH in dichloromethane). The mixture was then purified on silica gel column by combi-flash chromatography system using a gradient of dichloromethane/methanol (100:0 to 100 to 10) to provide the pure desired product 3 as a pale-yellow solid. $^1$H NMR (400 MHz, $CDCl_3$): δ 8.19 (s, 1H, —CH=N), 7.18 (s, 1H, =CH), 6.99 (d, 1H, J=8.2 Hz, Ar—H6), 6.46 (d, 1H, J=8.2 Hz, Ar—H5), 3.60-3.70 (m, 2H, —$CH_2$—), 3.25-3.35 (m, 3H), 2.86 (s, 3H, $NCH_3$), 1.36 (d, 3H, J=6.7 Hz, i-propyl $CH_3$), 1.32 (d, 3H, J=6.7 Hz, i-propyl $CH_3$). $^{13}$C NMR (400 MHz, $CDCl_3$): δ 152.99, 149.50, 125.68, 122.36, 116.0, 109.32, 109.14, 103.27, 57.39, 53.95, 35.58, 22.15, 15.57, 14.91. HRMS (ESI, positive) m/z for $C_{15}H_{22}N_3O_2$ [M+H]$^+$ calc'd: 276.1707; found 276.1703.

The third step involved the preparation of a nitrilated derivative (4) of psilocin:

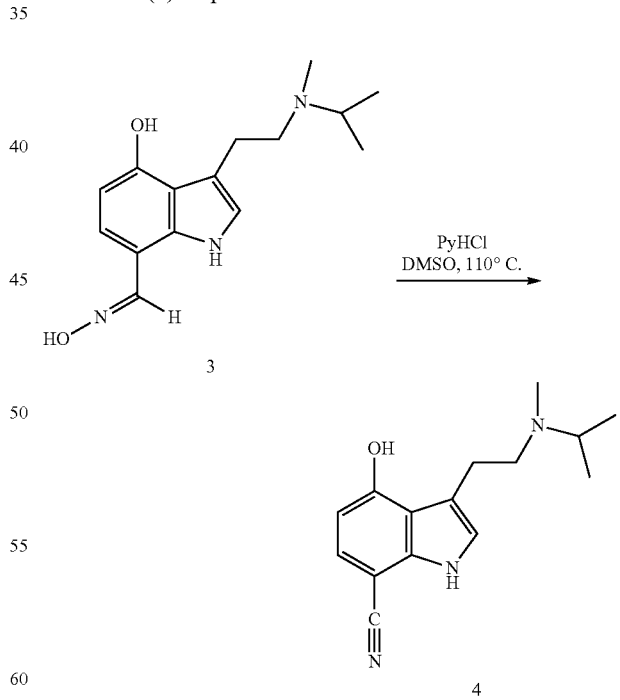

To a solution of aldehyde derivative 3 (1 eq.) in anhydrous DMSO, was added 5 eq. of pyridine-HCl, and the reaction mixture was stirred at 110° C. for 3 hours. The reaction was monitored by TLC (10% MeOH in DCM). The mixture was then purified on silica gel column by combi-flash chromatography system using a gradient of dichloromethane-methanol (100:0 to 100 to 10) to provide the desired product 4 as a pale-yellow solid. $^1$H NMR (400 MHz, CD$_3$OD): δ 7.37 (d, 1H, J=8.2 Hz, Ar—H6), 7.24 (bs, 1H, =CH), 6.55 (d, 1H, J=8.2 Hz, Ar—H5), 2.91 (bs, 5H, 2×CH and CH), 2.75 (s, 3H), 1.3-1.40 (d, 3H, J=6.7 Hz, CH$_3$_Ispropyl), 1.36 (d, 3H, J=6.7 Hz, CH$_3$_Isopropyl). HRMS (ESI, positive) m/z for C$_{15}$H$_{20}$N$_3$O [M+H]$^+$ calc'd: 258.1601; found: 258.1604. It is noted that product 4 corresponds with the chemical compound having formula (XI) set forth herein.

SEQUENCE LISTING

```
Sequence total quantity: 12
SEQ ID NO: 1              moltype = DNA  length = 3810
FEATURE                   Location/Qualifiers
misc_feature              1..3810
                          note = Nucleic acid sequence of pCDM4 vector
source                    1..3810
                          mol_type = other DNA
                          organism = synthetic construct
SEQUENCE: 1
gctaacagcg cgatttgctg gtgacccaat gcgaccagat gctccacgcc cagtcgcgta   60
ccgtcttcat gggagaaaat aatactgttg atgggtgtct ggtcagagac atcaagaaat  120
aacgccggaa cattagtgca ggcagcttcc acagcaatgg catcctggtc atccagcgga  180
tagttaatga tcagcccact gacgcgttgc gcgagaagat tgtgcaccgc cgctttacag  240
gcttcgacgc cgcttcgttc taccatcgac accaccacgc tggcacccag ttgatcggcg  300
cgagatttaa tcgccgcgac aatttgcgac ggcgcgtgca gggccagact ggaggtggca  360
acgccaatca gcaacgactg tttgcccgcc agttgttgtg ccacgcggtt gggaatgtaa  420
ttcagctccg ccatcgccgc ttccactttt tcccgcgttt tcgcagaaac gtggctggcc  480
tggttcacca cgcgggaaac ggtctgataa gagacaccgg catactctgc gacatcgtat  540
aacgttactg gtttcacatt caccaccctg aattgactct cttccgggcg ctatcatgcc  600
ataccgcgaa aggttttgcg ccattcgatg gtgtccggga tctcgacgct ctcccttatg  660
cgactcctgc attaggaagc agcccagtag taggttgagg ccgttgagca ccgccgccgc  720
aaggaatggt gcatgcaagg agatggcgcc caacagtccc ccggccacgg ggcctgccac  780
catacccacg ccgaaacaag cgctcatgag cccgaagtgg cgagcccgat cttcccatc   840
ggtgatgtcg gcgatataag cgccagcaac cgcacctgtg gcgccggtga tgccggccaa  900
gatgcgtccg gcgtagccta ggatcgagat cgatctcgat cccgcgaaat taatacgact  960
cactataggg gaattgtgag cggataacaa ttcccctcta gaaataattt tgtttaactt 1020
taagaaggag atatacatat ggcagatctc aattggatat cggccggcca cgcgatcgct 1080
gacgtcggta ccctcgagtc tggtaaagaa accgctgctg cgaaatttga acgccagcac 1140
atggactcgt ctactagtcg cagcttaatt aacctaaact gctgccaccg ctgagcaata 1200
actagcataa ccccttgggg cctctaaacg ggtcttgagg ggtttttgc tagcgaaagg  1260
aggagtcgac actgcttccg gtagtcaata aaccggtaaa ccagcaatag acataagcgg 1320
ctatttaacg accctgccct gaaccgacga ccgggtcatc gtggccggat cttgcggccc 1380
ctcggcttga acgaattgtt agacattatt tgccgactac cttggtgatc tcgcctttca 1440
cgtagtggac aaattcttcc aactgatctg cgcgcgaggc caagcgatct tcttcttgtc 1500
caagataagc ctgtctagct tcaagtatga cgggctgata ctgggccggc aggcgctcca 1560
ttgcccagtc ggcagcgaca tccttcggcg cgattttgcc ggttactgcg ctgtaccaaa 1620
tgcgggacaa cgtaagcact acatttcgct catcgccagc ccagtcgggc ggcgagttcc 1680
atagcgttaa ggtttcattt agcgcctcaa atagatcctg ttcaggaacc ggatcaaaga 1740
gttcctccgc cgctggacct accaaggcaa cgctatgttc tcttgctttt gtcagcaaga 1800
tagccagatc aatgtcgatc gtggctggct cgaagatacc tgcaagaatg tcattgcgct 1860
gccattctcc aaattgcagt tcgcgcttag ctggataacg ccacgaagtg atgtcgtcgt 1920
gcacaacaat ggtgacttct acagcgcgga gaatctcgct ctctccaggg gaagccgaag 1980
tttccaaaag gtcgttgatc aaagctcgcc gcgttgtttc atcaagcctt acggtcaccg 2040
taaccagcaa atcaatatca ctgtgtggct tcaggccgcc atccactgcg gagccgtaca 2100
aatgtacggc cagcaacgtc ggttcgagat ggcgctcgat gacgccaact acctctgata 2160
gttgagtcga tacttcggcg atcaccgctt ccctcatact cttcctttt caatattatt 2220
gaagcattta tcagggttat tgtctcatga gcggatacat atttgaatgt atttagaaaa 2280
ataaacaaat agccagctca ctcggtcgct acgctccggg cgtgagactg cggcgggcgc 2340
tgcggacaca tacaaagtta cccacagatt ccgtggataa gcaggggact aacatgtgag 2400
gcaaaacagc agggccgcgc cggtggcgtt tttccatagg ctccgccctc ctgccagagt 2460
tcacataaac agacgctttt ccggtgcatc tgtgggagcc gtgaggctca accatgaatc 2520
tgacagtacg ggcgaaaccc gacaggactt aaagatcccc accgtttccg gcgggtcgct 2580
ccctcttgcg ctctcctgtt ccgaccctgc cgtttaccgg atacctgttc cgcctttcct 2640
ccttacggga agtgtggcgc tttctcatag ctcacacact ggtatctcgg ctcggtgtag 2700
gtcgttcgct ccaagctggg ctgtaagcaa gaactccccg ttcagcccga ctgctgcgcc 2760
ttatccggta actgttcact tgagtccaac ccggaaaagc acgtaaaac gccactggca  2820
gcagccattg gtaactggga gttcgcagag gatttgttta gctaaacacg cggttgctct 2880
tgaagtgtgc gccaaagtcc ggctacactg gaaggacaga tttggttgct gtgctctgca 2940
aaagccagtt accacggtta agcagttccc caactgactt aaccttcgat caaaccacct 3000
ccccaggtgg ttttttcgtt tacagggcaa aagattacgc gcagaaaaaa aggatctcaa 3060
gaagatcctt tgatcttttc tactgaaccg ctctagattt cagtgcaatt tatctcttca 3120
aatgtagcac ctgaagtcag ccccatacga taaagttgt aattctcatg ttagtcatgt 3180
cccgcgccca ccggaaggag ctgactgggt tgaaggctct caagggcatc ggtcgagatc 3240
ccggtgccta atgagtgagc taacttacat taattgcgtt gcgctcactg cccgctttcc 3300
agtcgggaaa cctgtcgtgc cagctgcatt aatgaatcgg ccaacgcgcg gggagaggcg 3360
gtttgcgtat tgggcgccaa ggtggttttt cttttcacca gtgagacgga caacagctga 3420
ttgcccttca ccgcctggcc ctgagagagt tgcagcaagc ggtccacgct ggtttgcccc 3480
agcaggcgaa aatcctgttt gatggtggtt aacggcggga tataacatga gctgtcttcg 3540
gtatcgtcgt atcccactac cgagatgtcc gcaccaacgc gcagcccgga ctcggtaatg 3600
gcgcgcattg cgcccagcgc catctgatcg ttggcaacca gcatcgcagt gggaacgatg 3660
ccctcattca gcatttgcat ggtttgttga aaacggacga tggcactcca gtcgccttcc 3720
```

-continued

```
cgttccgcta tcggctgaat ttgattgcga gtgagatatt tatgccagcc agccagacgc  3780
agacgcgccg agacagaact taatgggccc                                   3810

SEQ ID NO: 2              moltype = DNA   length = 24
FEATURE                   Location/Qualifiers
misc_feature              1..24
                          note = Nucleic acid sequence encoding a synthetic FLAG
                          epitope tagpolypeptide
source                    1..24
                          mol_type = other DNA
                          organism = synthetic construct
SEQUENCE: 2
gactacaagg atgacgatga caaa                                         24

SEQ ID NO: 3              moltype = AA   length = 8
FEATURE                   Location/Qualifiers
REGION                    1..8
                          note = Deduced amino acid sequence of a synthetic FLAG
                          epitope tagpolypeptide
source                    1..8
                          mol_type = protein
                          organism = synthetic construct
SEQUENCE: 3
DYKDDDDK                                                           8

SEQ ID NO: 4              moltype = DNA   length = 549
FEATURE                   Location/Qualifiers
source                    1..549
                          mol_type = other DNA
                          organism = Streptomyces griseofuscus
SEQUENCE: 4
atgaacacct tcagaacagc cactgccaga gacatacctg atgtagcagc aactcttacg  60
gaagccttcg caactgatcc acccacgcag tgggtgttcc ccgacggtac tgccgccgtc  120
agcaggttct ttacacatgt tgcagatagg gttcacacgg ccggtggtat tgttgagcta  180
ctaccagaca gagccgccat gattgcattg ccaccacacg tgaggctgcc aggagaagct  240
gccgacggaa ggcaggcgga aattcagaga aggctggcag acaggcaccc gctgacacct  300
cactactacc tgctgtttta cggagttaga acggcacacc agggttcggg attgggcgga  360
agaatgctgg ccagattaac tagcagagct gataaggaca gggtgggtac atatactgag  420
gcatccacct ggcgtggcgc tagactgatg ctgagacatg gattccatgc tacaaggcca  480
ctaagattgc cagatggacc cagcatgttt ccactttgga gagatccaat ccatgatcat  540
tctgattag                                                         549

SEQ ID NO: 5              moltype = AA   length = 182
FEATURE                   Location/Qualifiers
source                    1..182
                          mol_type = protein
                          organism = Streptomyces griseofuscus
SEQUENCE: 5
MNTFRTATAR DIPDVAATLT EAFATDPPTQ WVFPDGTAAV SRFFTHVADR VHTAGGIVEL  60
LPDRAAMIAL PPHVRLPGEA ADGRQAEIQR RLADRHPLTP HYYLLFYGVR TAHQGSGLGG  120
RMLARLTSRA DRDRVGTYTE ASTWRGARLM LRHGFHATRP LRLPDGPSMF PLWRDPIHDH  180
SD                                                                182

SEQ ID NO: 6              moltype = DNA   length = 42
FEATURE                   Location/Qualifiers
misc_feature              1..42
                          note = Nucleic acid sequence encoding a synthetic V5
                          epitope tagpolypeptide
source                    1..42
                          mol_type = other DNA
                          organism = synthetic construct
SEQUENCE: 6
ggtaagccaa ttccaaatcc tttgttgggt ttggactcca cc                     42

SEQ ID NO: 7              moltype = AA   length = 14
FEATURE                   Location/Qualifiers
REGION                    1..14
                          note = Deduced amino acid sequence of a synthetic V5
                          epitope tagpolypeptide
source                    1..14
                          mol_type = protein
                          organism = synthetic construct
SEQUENCE: 7
GKPIPNPLLG LDST                                                    14

SEQ ID NO: 8              moltype = DNA   length = 1170
FEATURE                   Location/Qualifiers
source                    1..1170
                          mol_type = other DNA
```

```
                        organism = Thermotoga maritima
SEQUENCE: 8
atgaaaggat atttcggacc atacggtggc cagtacgtac cagaaatatt aatgggtgcc   60
ttagaggagt tagaggcagc atacgaggag attatgaagg atgagagctt ctggaaggag  120
ttcaacgatc tactgaggga ttacgcaggc agaccaacgc cattgtactt tgccaggaga  180
ttgtctgaga agtacggcgc ccgtgtttac ttgaagcgtg aggatctgct gcacactgga  240
gcacacaaga taaataacgc tatcggacag gttttattgg ccaaattaat ggggaagaca  300
cgtatcatag ccgagacggg agctgggcag catggagtcg ctactgctac cgctgctgcc  360
ctgttcggaa tggaatgtgt gatctacatg ggtgaagagg acacaatcag acagaagtta  420
aacgtggagc gtatgaaatt attagggggct aaagttgtcc ctgttaagtc tggcagtagg  480
accttgaagg atgcgataga cgaggctttg agagactgga ttactaattt acagacaaca  540
tattatgtta tcgatctgt tgttggtccc caccctacc caattatcgt aaggaatttc   600
cagaaggtta tcggtgagga gaccaagaag caaataccag aaaaggaagg tcgtttgcca  660
gactatatag ttgcctgcgt aggcggcggt agcaatgccg caggtatatt ttacccattc  720
atagactctg gagtaaagct gataggtgtt gaggcaggtg gcgagggatt ggagacaggt  780
aaaacacgcag cctcgttatt aaagggtaaa attggctatt acatggatc gaagaccttt  840
gttctacaag atgactgggg tcaagtccaa gtgagccatt cggtgtcagc tggtcttgac  900
tattcaggag taggacctga gcatgcttat tggagagaga agggaaggt tctgtacgac  960
gcagtgactg acgaagaggc tttggacgca tttatagagt tatcaagact agagggcatt 1020
ataccgctt tagagtcatc gcatgctcta gcatatttga agaagataaa tataaaaggt 1080
aaggttgtgg tggtcaacct atcagggaga gggataaag acctggagtc agtcttaaac 1140
catccatacg tgagagaaag aattagatga                                   1170

SEQ ID NO: 9          moltype = AA  length = 389
FEATURE               Location/Qualifiers
source                1..389
                      mol_type = protein
                      organism = Thermotoga maritima
SEQUENCE: 9
MKGYFGPYGG QYVPEILMGA LEELEAAYEE IMKDESFWKE FNDLLRDYAG RPTPLYFARR   60
LSEKYGARVY LKREDLLHTG AHKINNAIGQ VLLAKLMGKT RIIAETGAGQ HGVATATAAA  120
LFGMECVIYM GEEDTIRQKL NVERMKLLGA KVVPVKSGSR TLKDAIDEAL RDWITNLQTT  180
YYVIGSVVGP HPYPIIVRNF QKVIGEETKK QIPEKEGRLP DYIVACVGGG SNAAGIFYPF  240
IDSGVKLIGV EAGGEGLETG KHAASLLKGK IGYLHGSKTF VLQDDWGVQ VSHSVSAGLD   300
YSGVGPEHAY WRETGKVLYD AVTDEEALDA FIELSRLEGI IPALESSHAL AYLKKINIKG  360
KVVVVNLSGR GDKDLESVLN HPYVRERIR                                    389

SEQ ID NO: 10         moltype = DNA  length = 5203
FEATURE               Location/Qualifiers
misc_feature          1..5203
                      note = Nucleic acid sequence of pETM6-H10 vector
source                1..5203
                      mol_type = other DNA
                      organism = synthetic construct
SEQUENCE: 10
gaagaattgt gagcggataa caattcccct ctagaaataa ttttgtttaa ctttaagaag   60
gagatataca tatggcagat ctcaattgga tatcggccgg ccacgcgatc gctgacgtcg  120
gtaccctcga gtctggtaaa gaaaccgctg ctgcgaaatt tgaacgccag cacatggact  180
cgtctactag tcgcagctta attaacctaa actgctgcca ccgctgagca ataactagca  240
taaccccttg gggcctctaa acgggtcttg aggggttttt tgctagcgaa aggaggagtc  300
gactatatcc ggattggcga atgggacgcg ccctgtagcg gcgcattaag cgcggcgggt  360
gtggtggtta cgcgcagcgt gaccgctaca cttgccagcg ccctagcgcc cgctcctttc  420
gctttcttcc cttcctttct cgccacgttc gccggctttc ccgtcaagc tctaaatcgg  480
gggctccctt tagggttccg atttagtgct ttacggcacc tcgaccccaa aaaacttgat  540
tagggtgatg gttcacgtag tgggccatcg ccctgataga cggtttttcg ccctttgacg  600
ttggagtcca cgttctttaa tagtggactc ttgttccaaa ctggaacaac actcaaccct  660
atctcggtct attcttttga tttataaggg attttgccga tttcggccta ttggttaaaa  720
aatgagctga tttaacaaaa atttaacgcg aattttaaca aaatattaac gtttacaatt  780
tctggcggca cgatggcatg agattatcaa aaaggatctt cacctagatc cttttaaatt  840
aaaaatgaag ttttaaatca tatatgagta aacttggtct gacagttacc                900
aatgcttaat cagtgaggca cctatctcag cgatctgtct atttcgttca tccatagttg   960
cctgactccc cgtcgtgtag ataactacga tacgggaggg cttaccatct ggccccagtg  1020
ctgcaatgat accgcgagac ccacgctcac cggctccaga tttatcagca ataaaccagc  1080
cagccggaag ggccgagcgc agaagtggtc ctgcaacttt atccgcctcc atccagtcta  1140
ttaattgttg ccgggaagct agagtaagta gttcgccagt taatagtttg cgcaacgttg  1200
ttgccattgc tacaggcatc gtggtgtcac gctcgtcgtt tggtatggct tcattcagct  1260
ccggttccca acgatcaagg cgagttacat gatccccat gttgtgcaaa aaagcggtta  1320
gctccttcgg tcctccgatc gttgtcagaa gtaagttggc cgcagtgtta tcactcatgg  1380
ttatggcagc actgcataat tctcttactg tcatgccatc cgtaagatgc ttttctgtga  1440
ctggtgagta ctcaaccaag tcattctgag aatagtgtat gcggcgaccg agttgctctt  1500
gcccggcgtc aatacgggat aataccgcgc cacatagcag aactttaaaa gtgctcatca  1560
ttggaaaacg ttcttcgggg cgaaaactct caaggatctt accgctgttg atccagttcg  1620
atgtaacc cactcgtgca cccaactgat cttcagcatc ttttactttc accagcgttt  1680
ctgggtgagc aaaaacagga aggcaaaatg ccgcaaaaaa gggaataagg gcgacacgga  1740
aatgttgaat actcatactc ttcctttttc aatcatgatt gaagcattta tcagggttat  1800
tgtctcatga gcggatacat atttgaatgt atttagaaaa ataaacaaat aggtcatgac  1860
caaaatccct taacgtgagt tttcgttcca ctgagcgtca gaccccgtag aaaagatcaa  1920
aggatcttct tgagatcctt tttttctgcg cgtaatctgc tgcttgcaaa caaaaaaacc  1980
accgctacca gcggtggttt gtttgccgga tcaagagcta ccaactcttt ttccgaaggt  2040
```

```
aactggcttc agcagagcgc agataccaaa tactgtcctt ctagtgtagc cgtagttagg   2100
ccaccactcc aagaactctg tagcaccgcc tacataccte gctctgctaa tcctgttacc   2160
agtggctgct gccagtggcg ataagtcgtg tcttaccggg ttggactcaa gacgatagtt   2220
accggataag gcgcagcggt cgggctgaac gggggggttcg tgcacacagc ccagcttgga   2280
gcgaacgacc tacaccgaac tgagatacct acagcgtgag ctatgagaaa gcgccacgct   2340
tcccgaaggg agaaaggcgg acaggtatcc ggtaagcggc agggtcggaa caggagagcg   2400
cacgagggag cttccagggg gaaacgcctg gtatctttat agtcctgtcg ggtttcgcca   2460
cctctgactt gagcgtcgat ttttgtgatg ctcgtcaggg gggcggagcc tatggaaaaa   2520
cgccagcaac gcggccttttt tacggttcct ggccttttgc tggcctttttg ctcacatgtt   2580
ctttcctgcg ttatcccctg attctgtgga taaccgtatt accgcctttg agtgagctga   2640
taccgctcgc cgcagccgaa cgaccgagcg cagcgagtca gtgagcgagg aagcggaaga   2700
gcgcctgatg cggtattttc tccttacgca tctgtgcggt atttcacacc gcatatatgg   2760
tgcactctca gtacaatctg ctctgatgcc gcatagttaa gccagtatac actccgctat   2820
cgctacgtga ctgggtcatg gctgcgcccc gacaccgcc aacaccgct gacgcgccct   2880
gacgggcttg tctgctcccg gcatccgctt acagacaagc tgtgaccgtc tccgggagct   2940
gcatgtgtca gaggttttca ccgtcatcac cgaaacgcgc gaggcagctg cggtaaagct   3000
catcagcgtg gtcgtgaagc gattcacaga tgtctgcctg ttcatccgcg tccagctcgt   3060
tgagtttctc cagaagcgtt aatgtctggc ttctgataaa gcgggccatg ttaagggcgg   3120
ttttttcctg tttggtcact gatgcctccg tgtaagggg atttctgttc atggggggtaa   3180
tgataccgat gaaacgagag aggatgctca cgatacgggt tactgatgat gaacatgccc   3240
ggttactgga acgttgtgag ggtaaacaac tggcggtatg gatgcggcgg gaccagagaa   3300
aaatcactca gggtcaatgc cagcgcttcg ttaatacaga tgtaggtgtt ccacaggta   3360
gccagcagca tcctgcgatg cagatccgga acataatggt gcagggcgct gacttccgcg   3420
tttcagact ttacgaaaca cggaaaccga agaccattca tgttgttgct caggtcgcag   3480
acgttttgca gcagcagtcg cttcacgttc gctcgcgtat cggtgattca ttctgctaac   3540
cagtaaggca accccgccag cctagccggg tcctcaacga caggagccgg atcatgcag   3600
tcatgccccg cgcccaccgg aaggagctga ctgggttgaa ggctctcaag gcatcggtc   3660
gagatccccgg tgcctaatga gtgagctaac ttacattaat tgcgttgcgc tcactgcccg   3720
ctttccagtc gggaaacctg tcgtgccagc tgcattaatg aatcggccaa cgcgcgggga   3780
gaggcggttt gcgtattggg cgccagggtg gtttttcttt tcaccagtga cgggggcaac   3840
agctgattgc ccttcaccgc ctggccctga gagagttgca gcaagcggtc cacgctggtt   3900
tgccccagca ggcgaaaatc ctgtttgatg gtggttaacg gcgggatata acatgagctg   3960
tcttcggtat cgtcgtatcc cactaccgag atgtccgcac caacgcgcag cccggactcg   4020
gtaatggcgc gcattgcgcc cagcgccatc tgatcgttgg caaccagcat cgcagtggga   4080
acgatgccct cattcagcat ttgcatggtt tgttgaaaac cggacatggc actccagtcg   4140
ccttcccgtt ccgctatcgg ctgaatttga ttgcgagtga gatatttatg ccagccagcc   4200
agacgcagac gcgccgagac agaacttaat gggcccgcta acagcgcgat ttgctggtga   4260
cccaatgcga ccagatgctc cacgcccagt cgcgtaccgt cttcatggga gaaaataata   4320
ctgttgatgg gtgtctggtc agagacatca agaaataacg ccggaacatt agtgcaggca   4380
gcttccacag caatggcatc ctggtcatcc agcggatagt taatgatcag cccactgacg   4440
cgttgcgcga agattgtg caccgccgct tacaggctt cgacgccgct tcgttctacc   4500
atcgacacca ccacgctggc acccagtga tcggcgcgag atttaatcgc cgcgacaatt   4560
tgcgacggcg cgtgcagggc cagactggag gtggcaacgc caatcagcaa cgactgtttg   4620
cccgccagtt gttgtgccac gcggttggga atgtaattca gctccgccat cgccgcttcc   4680
actttttccc gcgttttcgc agaaacgtgg ctggcctggt tcaccacgcg ggaaacggtc   4740
tgataagaga caccggcata ctctgcgaca tcgtataacg ttactggttt cacattcacc   4800
accctgaatt gactctcttc cgggcgctat catgccatac cgcgaaaggt tttgcgccat   4860
tcgatggtgt ccgggatctc gacgctctcc cttatgcgac tcctgcatta ggaagcagcc   4920
cagtagtagg ttgaggccgt tgagcaccgc cgccgcaagg aatggtgcat gcaaggagat   4980
ggcgcccaac agtcccccgg ccacgggcc tgccaccata cccacgccga acaagcgct   5040
catgaccccg aagtggcgag cccgatcttc cccatcgtg atgtcggcga tataggcgcc   5100
agcaaccgca cctgtggcgc cggtgatgcc ggccacgatg cgtccggcgt agcctaggat   5160
cgagatcgat ctcgatcccg cgaaattaat acgactcact acg              5203

SEQ ID NO: 11         moltype = DNA   length = 1446
FEATURE               Location/Qualifiers
source                1..1446
                      mol_type = other DNA
                      organism = Bacillus atrophaeus
SEQUENCE: 11
atgatgtctg aaaatttgca attgtcagct gaagaaatga gacaattggg ttaccaagca     60
gttgatttga tcatcgatca catgaaccat ttgaagtcta agccagtttc agaaacaatc    120
gattctgata tcttgagaaa taagttgact gaatctatcc cagaaaatgg ttcagatcca    180
aaggaattgt tgcatttctt gaacagaaac gtttttaatc aaattacaca tgttgatcat    240
ccacatttct tggcttttgt tccaggtcca aataattacg ttggtgttgt tgcagatttc    300
ttggcttctg gtttaatgt ttttccaact gcatggattg ctggtgcagg tgctgaacaa    360
atcgaattga ctacaattaa ttggttgaaa tctatgttgg ttttccaga ttcagctgaa    420
ggtttatttg tttctggtgg ttcaatggca aattgacag ctttgactgt tgcaagacag    480
gctaagttga acaacgatat cgaaaatgct gttgttact tctctgatca aacacatttc    540
tcagttgata gagcattgaa ggttttaggt tttaaacatc atcaaatctg tagaatcgaa    600
acagatgaac atttgagaat ctctgtttca gcttttgaaga aacaaattaa agaagataga    660
actaagggta aaaagccatt ctgtgttatt gcaaatgctg gtactacaaa ttgtggtgct    720
gttgattctt tgaacgaatt agcagatttg tgtaacgatg aagatgtttg gttgcatgct    780
gatgctgctt atggtgctcc agctatcttg tctgaaaagt ttcagctat gttgcaaggt    840
attcatagag cagattcttt gactttagat ccacataagt ggttgttcca accatacgat    900
gttggtgtg ttttgatcag aaactctcaa tatttgtcaa agacttttag aatgatgcca    960
gaatacatca aggattcaga aactaacgtt gaaggtgaaa ttaatttcgg tgaatgtggt   1020
atcgaattgt caagaagatt cagagctttg aaggtttggt tgtctttaa agttttcggt   1080
gttgctgctt ttagacaagc aatcgatcat ggtatcatgt tagcagaaca agttgaagca   1140
```

```
                                        -continued
ttttttgggta  aagcaaaaga  ttgggaagtt  gttacaccag  ctcaattggg  tatcgttact  1200
tttagataca   ttccatctga  attggcatca  acagatacta  ttaatgaaat  taataagaaa  1260
ttggttaagg   aaatcacaca  tagaggtttc  gctatgttat  ctactacaga  attgaaggaa  1320
aaggttgtta   ttagattgtg  ttcaattaat  ccaagaacta  caactgaaga  aatgttgcaa  1380
atcatgatga   agattaaagc  attggctgaa  gaagtttcta  tttcataccc  atgtgttgct  1440
gaataa                                                                   1446

SEQ ID NO: 12          moltype = AA  length = 481
FEATURE                Location/Qualifiers
source                 1..481
                       mol_type = protein
                       organism = Bacillus atrophaeus
SEQUENCE: 12
MMSENLQLSA  EEMRQLGYQA  VDLIIDHMNH  LKSKPVSETI  DSDILRNKLT  ESIPENGSDP   60
KELLHFLNRN  VFNQITHVDH  PHFLAFVPGP  NNYVGVVADF  LASGFNVFPT  AWIAGAGAEQ  120
IELTTINWLK  SMLGFPDSAE  GLFVSGGSMA  NLTALTVARQ  AKLNNDIENA  VVYFSDQTHF  180
SVDRALKVLG  FKHHQICRIE  TDEHLRISVS  ALKKQIKEDR  TKGKKPFCVI  ANAGTTNCGA  240
VDSLNELADL  CNDEDVWLHA  DGSYGAPAIL  SEKGSAMLQG  IHRADSLTLD  PHKWLFQPYD  300
VGCVLIRNSQ  YLSKTFRMMP  EYIKDSETNV  EGEINFGECG  IELSRRFRAL  KVWLSFKVFG  360
VAAFRQAIDH  GIMLAEQVEA  FLGKAKDWEV  VTPAQLGIVT  FRYIPSELAS  TDTINEINKK  420
LVKEITHRGF  AMLSTTELKE  KVVIRLCSIN  PRTTTEEMLQ  IMMKIKALAE  EVSISYPCVA  480
E                                                                       481
```

The invention claimed is:

1. A chemical compound having the formula (I):

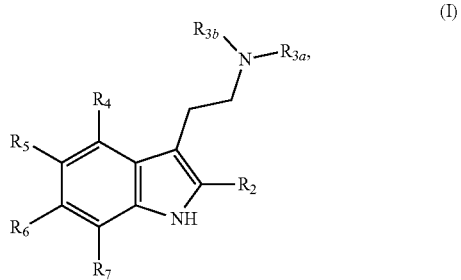

wherein, at least $R_5$, and optionally $R_6$ and/or $R_7$ is a nitrile group, and wherein each non-nitrilated $R_6$ or $R_7$ is a hydrogen atom, an alkyl group, or O-alkyl group, wherein $R_2$ is a hydrogen atom or an O-alkyl group, wherein $R_4$ is an O-alkyl group, an O-acyl group, a hydroxy group, or a hydrogen atom and wherein $R_{3a}$ and $R_{3b}$ are independently a hydrogen atom, an alkyl group, acyl group or an aryl group, wherein when each of $R_2$, $R_4$, and $R_6$ are a hydrogen atom, and simultaneously $R_{3a}$ and $R_{3b}$ are each a hydrogen atom or each an alkyl group, $R_7$ is an alkyl group or O-alkyl group.

2. A chemical compound according to claim 1, wherein each non-nitrilated $R_6$ or $R_7$ is a hydrogen atom, an alkyl group, or O-alkyl group, $R_2$ is a hydrogen atom or an O-alkyl group, and $R_4$ is a hydrogen atom, a hydroxy group, or O-alkyl group.

3. A chemical compound according to claim 1, wherein each non-nitrilated $R_6$ or $R_7$ is a hydrogen atom, an alkyl group, or O-alkyl group, $R_2$ is a hydrogen atom, and $R_4$ is a hydrogen atom, a hydroxy group, or O-alkyl group.

4. A chemical compound according to claim 1, wherein each non-nitrilated $R_6$ or $R_7$ is a hydrogen atom, an alkyl group, or O-alkyl group, $R_2$ is a hydrogen atom, and $R_4$ is a hydrogen atom or O-alkyl group.

5. A chemical compound according to claim 1, wherein each non-nitrilated $R_6$ or $R_7$ is a hydrogen atom, a $(C_1-C_6)$-alkyl group, or $(C_1-C_6)$-O-alkyl group, $R_2$ is a hydrogen atom, and $R_4$ is a hydrogen atom, a hydroxy group, or $(C_1-C_6)$-O-alkyl group.

6. A chemical compound according to claim 1, wherein each non-nitrilated $R_6$ or $R_7$ is a hydrogen atom, a methyl ($-CH_3$) group, or methoxy ($-OCH_3$) group, $R_2$ is a hydrogen atom, and $R_4$ is a hydrogen atom, a hydroxy group, or methoxy ($-OCH_3$) group.

7. A chemical compound according to claim 1, wherein $R_6$ and $R_7$ are a hydrogen atom, an alkyl group, or O-alkyl group, $R_2$ is a hydrogen atom, and $R_4$ is a hydroxy group or O-alkyl group.

8. A chemical compound according to claim 1, wherein $R_6$ and $R_7$ are a hydrogen atom or an alkyl group, $R_2$ is a hydrogen atom, and $R_4$ is a hydrogen atom or O-alkyl group.

9. A chemical compound according to claim 1, $R_6$ is a hydrogen atom and $R_7$ is an alkyl group, $R_2$ is a hydrogen atom, and $R_4$ is a hydrogen atom or O-alkyl group.

10. A chemical compound according to claim 1, wherein $R_7$ is a hydrogen atom and $R_6$ is an alkyl group, $R_2$ is a hydrogen atom, and $R_4$ is a hydrogen atom or O-alkyl group.

11. A chemical compound according to claim 1, wherein $R_6$ is a hydrogen atom and $R_7$ is an alkyl group, $R_2$ is a hydrogen atom, and $R_4$ is a hydrogen atom.

12. A chemical compound according to claim 1, wherein $R_6$ is a hydrogen atom and $R_7$ is a $(C_1-C_6)$-alkyl group, $R_2$ is a hydrogen atom, and $R_4$ is a hydrogen atom.

13. A chemical compound according to claim 1, wherein $R_6$ is a hydrogen atom and $R_7$ is a $(C_1-C_3)$-alkyl group, $R_2$ is a hydrogen atom, and $R_4$ is a hydrogen atom.

14. A chemical compound according to claim 1, wherein $R_6$ is a hydrogen atom and $R_7$ is a methyl ($-CH_3$) group, $R_2$ is a hydrogen atom, and $R_4$ is a hydrogen atom.

15. A chemical compound according to claim 12, wherein $R_{3a}$ and $R_{3b}$ are each a hydrogen atom, or $R_{3a}$ and $R_{3b}$ are an acyl group and a hydrogen atom.

16. A chemical compound according to claim 13, wherein $R_{3a}$ and $R_{3b}$ are each a hydrogen atom, or $R_{3a}$ and $R_{3b}$ are an acyl group and a hydrogen atom.

17. A chemical compound according to claim 14, wherein $R_{3a}$ and $R_{3b}$ are each a hydrogen atom, or $R_{3a}$ and $R_{3b}$ are an acyl group and a hydrogen atom.

18. A chemical compound according to claim 1, wherein each of $R_{3a}$ and $R_{3b}$ are a hydrogen atom.

19. A chemical compound according to claim 1, wherein each of $R_{3a}$ and $R_{3b}$ are an alkyl group.

20. A chemical compound according to claim 1, wherein one of $R_{3a}$ and $R_{3b}$ is an acyl group, and one of $R_{3a}$ and $R_{3b}$ is a hydrogen atom.

21. A chemical compound according to claim 1, wherein the chemical compound is selected from the group of compounds having formulas (III), (IV), (V), (VII), (VIII), and (IX):

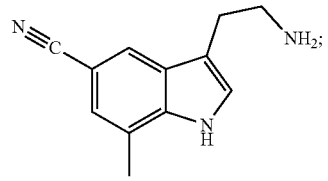
(III)

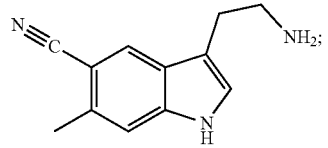
(IV)

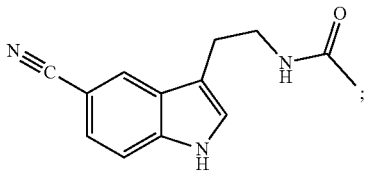
(V)

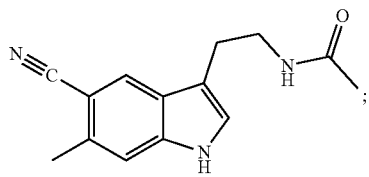
(VII)

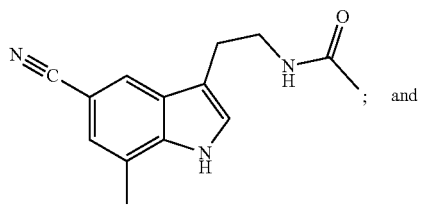
(VIII); and

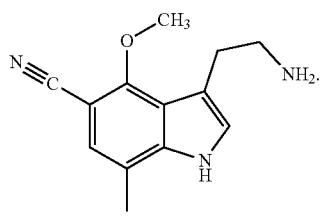
(IX)

22. A chemical compound according to claim 1, wherein the compound is at least about 95% (w/w) pure.

23. A pharmaceutical or recreational drug formulation comprising an effective amount of a chemical compound according to claim 1, together with a pharmaceutically acceptable excipient, diluent, or carrier.

* * * * *